United States Patent
Šikšnys et al.

(10) Patent No.: US 9,637,739 B2
(45) Date of Patent: May 2, 2017

(54) RNA-DIRECTED DNA CLEAVAGE BY THE CAS9-CRRNA COMPLEX

(71) Applicant: VILNIUS UNIVERSITY, Vilnius (LT)

(72) Inventors: Virginijus Šikšnys, Vilnius (LT); Giedrius Gasiunas, Biržu r. (LT); Tautvydas Karvelis, Vilniaus r. (LT)

(73) Assignee: VILNIUS UNIVERSITY, Vilnius (LT)

( * ) Notice: Subject to any disclaimer, the term of this patent is extended or adjusted under 35 U.S.C. 154(b) by 0 days.

(21) Appl. No.: 14/385,241

(22) PCT Filed: Mar. 15, 2013

(86) PCT No.: PCT/LT2013/000006
§ 371 (c)(1),
(2) Date: Sep. 15, 2014

(87) PCT Pub. No.: WO2013/141680
PCT Pub. Date: Sep. 26, 2013

(65) Prior Publication Data
US 2015/0045546 A1   Feb. 12, 2015

Related U.S. Application Data

(60) Provisional application No. 61/625,420, filed on Apr. 17, 2012, provisional application No. 61/613,373, filed on Mar. 20, 2012.

(51) Int. Cl.
| | |
|---|---|
| A61K 38/44 | (2006.01) |
| A61K 38/46 | (2006.01) |
| C12Q 1/68 | (2006.01) |
| C12N 9/16 | (2006.01) |
| C12N 9/22 | (2006.01) |
| C12N 15/74 | (2006.01) |
| C12N 15/113 | (2010.01) |
| C12N 15/10 | (2006.01) |
| C12P 19/34 | (2006.01) |
| C12N 15/90 | (2006.01) |

(52) U.S. Cl.
CPC .............. *C12N 15/113* (2013.01); *C12N 9/22* (2013.01); *C12N 15/102* (2013.01); *C12N 15/902* (2013.01); *C12N 15/907* (2013.01); *C12P 19/34* (2013.01); *C12Q 1/6811* (2013.01); *C12N 2310/10* (2013.01); *C12N 2310/12* (2013.01); *C12N 2310/14* (2013.01); *C12N 2310/3513* (2013.01); *C12N 2310/531* (2013.01); *C12N 2320/00* (2013.01); *C12N 2800/80* (2013.01)

(58) Field of Classification Search
None
See application file for complete search history.

(56) References Cited

U.S. PATENT DOCUMENTS

| | | |
|---|---|---|
| 8,697,359 B1 | 4/2014 | Zhang |
| 2010/0076057 A1 | 3/2010 | Sontheimer |
| 2014/0068797 A1 | 3/2014 | Doudna et al. |

FOREIGN PATENT DOCUMENTS

| | | |
|---|---|---|
| WO | 2007/025097 A2 | 3/2007 |
| WO | 2008/108989 A2 | 9/2008 |
| WO | 2013/176772 A1 | 11/2013 |
| WO | 2014/065596 A1 | 5/2014 |
| WO | 2014/089290 A1 | 6/2014 |
| WO | 2014/093622 A2 | 6/2014 |
| WO | 2014/099750 A2 | 6/2014 |

OTHER PUBLICATIONS

Deltcheva et al., Nature, Mar. 30, 2011; 471:602-607.*
Shapiro et al., Gene, 2005; 345(1)91-100.*
International Search Report PCT/LT2013/000006, mailed Jul. 24, 2013, 5 pages.
Third Party Observation PCT/LT2013/000006, submitted Jul. 18, 2014, 7 pages.
Sapranauskas et al. The *Streptococcus* lhermophiles CRISPR/Cas system provides immunity in *Escherichia coli* (Supplementary data), Nucleic Acids Research, 39 (2011) 9275-9282, Supplementary Figures, 8 pages.
Deltcheva et al. CRISPR RNA maturation by trans-encoded small RNA and host factor RNase III. Nature 471 (2011), 602-607, Methods, 2 pages.
Jinek et al. A Programmable Dual-RNA-Guided DNA Endonuclease in Adaptive Bacterial Immunity Science 337 (2012), 816-821, Supplementary Materials and Methods, 36 pages.
Gasiunas et al. Cas9-crRNA ribonucleoprotein complex mediates specific DNA cleavage for adaptive immunity in bacteria, Proc. Nat. Acad. Sci. vol. 109 (2012), E2579-E2586, Supporting Information, 8 pages.
Cong et al. Multiplex Genome Engineering Using CRISPR/Cas Systems, Science 339 (2013) 819-823, Supplementary Material, 25 pages.

(Continued)

*Primary Examiner* — Doug Schultz
(74) *Attorney, Agent, or Firm* — Thompson Hine LLP

(57) ABSTRACT

Isolation or in vitro assembly of the Cas9-crRNA complex of the *Streptococcus thermophilus* CRISPR3/Cas system and use for cleavage of DNA bearing a nucleotide sequence complementary to the crRNA and a proto-spacer adjacent motif. Methods for site-specific modification of a target DNA molecule using an RNA-guided DNA endonuclease comprising at least one RNA sequence and at least one of an RuvC active site motif and an HNH active site motif; for conversion of Cas9 polypeptide into a nickase cleaving one strand of double-stranded DNA by inactivating one of the active sites (RuvC or HNH) in the polypeptide by at least one point mutation; for assembly of active polypeptide-polyribonucleotides complex in vivo or in vitro; and for re-programming a Cas9-crRNA complex specificity in vitro or using a cassette containing a single repeat-spacer-repeat unit.

23 Claims, 14 Drawing Sheets

(56) References Cited

OTHER PUBLICATIONS

Qi et al. Repurposing CRISPR as an RNA-Guided Platform for Sequence-Specific Control of Gene Expression. Cell 152 (2013) 1173-1183, Supplemental Information, 7 pages.
Jiang et al. RNA-guided editing of bacterial genomes using CRISPR-Cas systems, Nature Biotechnology 31 (2013) 233-239, Online Methods, 2 pages, Supplementary Materials, 21 pages.
Cho et al. Targeted genome engineering in human cells with the Cas9 RNA-guided endonuclease. Nature Biotechnology 31 (2013) 230-232, Supplementary Information, 11 pages.
Jinek et al. RNA-programmed genome editing in human cells. eLife 2 (2013), e00471, 9 pages.
van der Oost et al. CRISPR-based adaptive and heritable immunity in prokaryotes. Trends in Biochemical Sciences 34 (2009) 401-408.
Garneau et al. The CRISPR/Cas bacterial immune system cleaves bacteriophage and plasmid DNA. Nature 468 (2010) 67-71.
Third Party Observation PCT/US2013/033106, Jul. 18, 2014, 7 pages.
Third Party Observation PCT/US2013/033106, EPO, Jul. 18, 2014, 7 pages.
Written Opinion PCT/LT2013/000006, Jul. 24, 2013, 10 pages.
International Preliminary Report n Patentability PCT/LT2013/000006, Sep. 23, 2014, 11 pages.
International Search Report PCT/US2013/033106, Jul. 24, 2013, 7 pages.
Written Opinion PCT/US2013/033106, Jul. 24, 2013, 10 pages.
International Preliminary Report on Patentability PCT/US2013/033106, Sep. 23, 2014, 11 pages.
Republic of China, Office Action of Application No. 201380023255.3, dated Jan. 26, 2016, 8 pages.
EP Communication of Application No. 13715080.1, dated Feb. 16, 2016, 13 pages.
Deveau et al., CRISPR/Cas system and Its Role in Phage-Bacteria Interactions, 2010, The Annual Review of Microbiology, 64, pp. 475-493.
Deltcheva et al., CRISPR RNA maturation by trans-encoded small RNA and host factor RNase III, Supplementary Tables, 2011, Nature, vol. 471. Total 22 pages.
Deltcheva et al., CRISPR RNA maturation by trans-encoded small RNA and host factor RNase III, Supplementary Figures, 2011, Nature, vol. 471. Total 35 pages.
Makarova et al., Evolution and classification of the CRISPR-Cas system, 2011, Nature Reviews Microbiology, vol. 9, pp. 467-477.
Communication pursuant to Article 94(3) EPC issued in European Patent Application No. 13715080.1 dated Nov. 8, 2016 (9 pages).
Notification of the Second Office Action issued in Chinese Patent Application No. 201380023255.3 dated Nov. 29, 2016 (15 pages, including translation and original).
Office Action issued in U.S. Appl. No. 14/385,857 dated Dec. 6, 2016 (12 pages).

\* cited by examiner

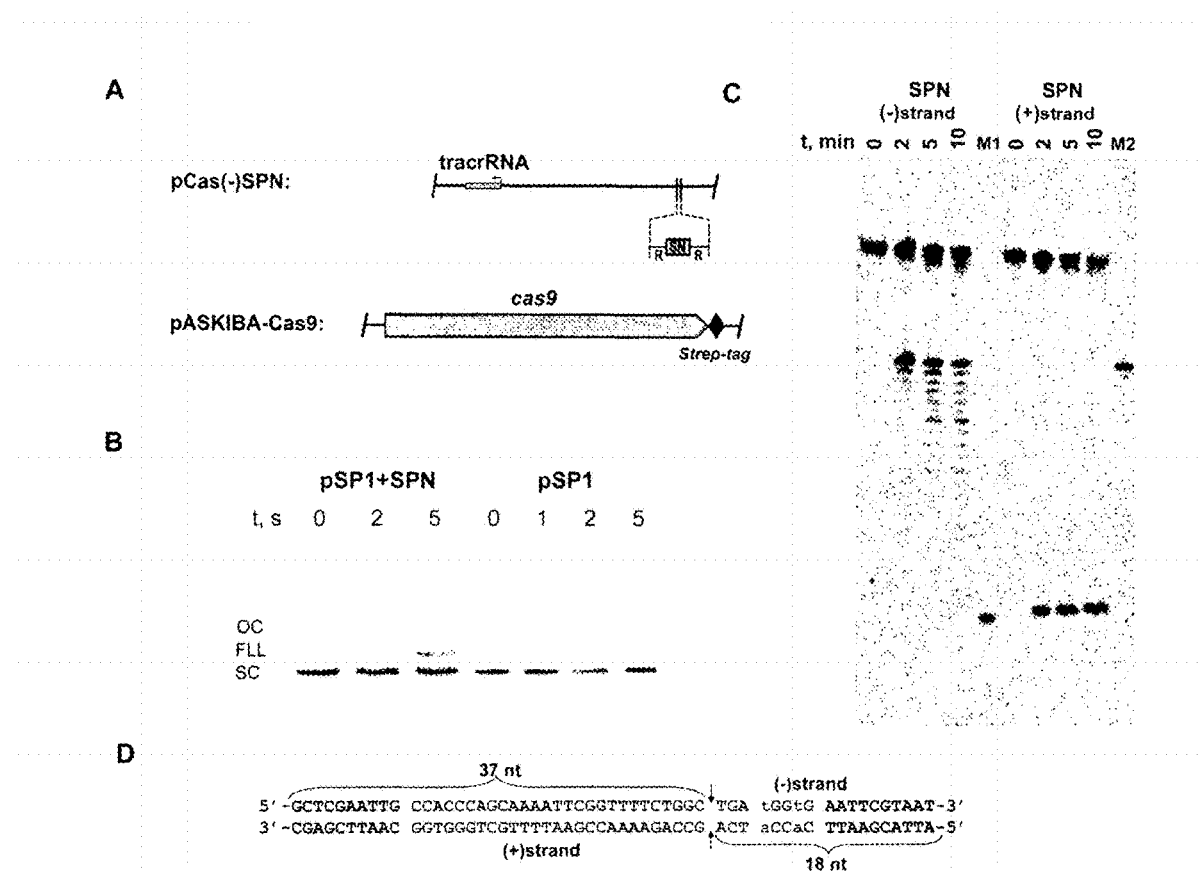
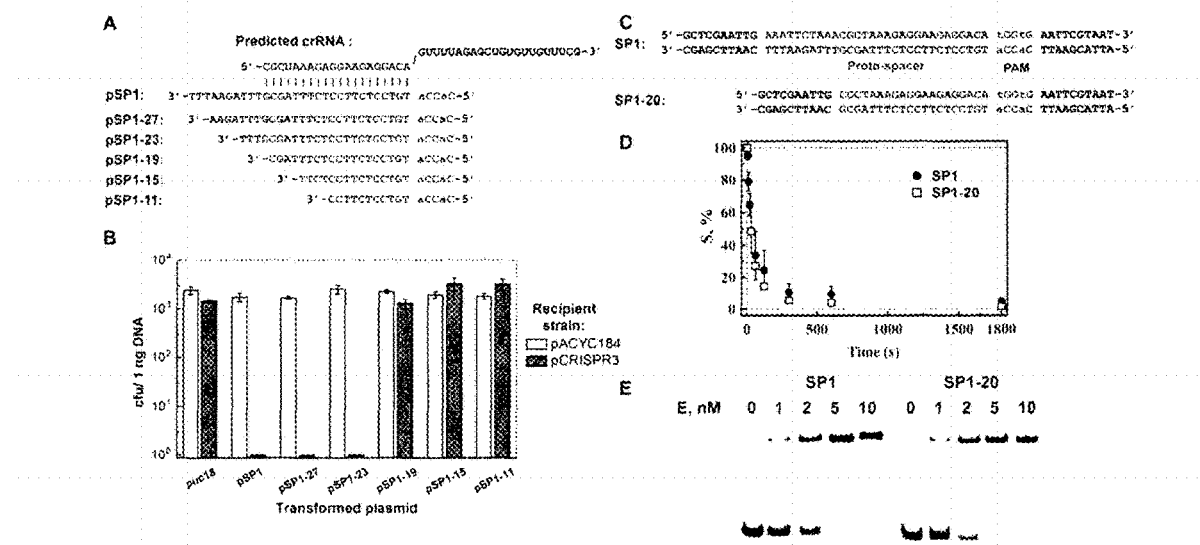
Figure 7
Figure 8

RNA-DIRECTED DNA CLEAVAGE BY THE CAS9-CRRNA COMPLEX

This application is a national stage of PCT/LT2013/000006 filed Mar. 15, 2013, WO 2013/141680, which claims priority to U.S. application Ser. Nos. 61/613,373 filed Mar. 20, 2012 and 61/625,420 filed Apr. 17, 2012, each of which is expressly incorporated by reference herein in its entirety.

BACKGROUND

Clustered Regularly Interspaced Short Palindromic Repeats (CRISPR) together with cas (CRISPR-associated) genes comprise an adaptive immune system that provides acquired resistance against invading foreign nucleic acids in bacteria and archaea (Barrangou et al., 2007. Science 315: 1709-12). CRISPR consists of arrays of short conserved repeat sequences interspaced by unique variable DNA sequences of similar size called spacers, which often originate from phage or plasmid DNA (Barrangou et al., 2007. Science 315:1709-12; Bolotin et al., 2005. Microbiology 151:2551-61; Mojica et al., 2005. J Mol Evol 60:174-82). The CRISPR-Cas system functions by acquiring short pieces of foreign DNA (spacers) which are inserted into the CRISPR region and provide immunity against subsequent exposures to phages and plasmids that carry matching sequences (Barrangou et al., 2007. Science 315:1709-12; Brouns et al., 2008. Science 321: 960-4) The CRISPR-Cas immunity is generally carried out through three stages, referred to as i) adaptation/immunization/spacer acquisition, ii) CRISPR expression/crRNA biogenesis, iii) interference/immunity. (Horvath & Barrangou, 2010. Science 327:167-70; Deveau et al., 2010. Annu Rev Microbiol. 64:475-93; Marraffini & Sontheimer, 2010. Nat Rev Genet 11, 181-90; Bhaya et al., Annu Rev Genet 45:273-97; Wiedenheft et al., 2012. Nature 482:331-338). Here, we specifically focus on the interference/immunity step which enables crRNA-mediated silencing of foreign nucleic acids.

The highly diverse CRISPR-Cas systems are categorized into three major types, which are further subdivided into ten subtypes, based on core element content and sequences (Makarova et al., 2011. Nat Rev Microbiol 9:467-77). The structural organization and function of nucleoprotein complexes involved in crRNA-mediated silencing of foreign nucleic acids differ between distinct CRISPR/Cas types (Wiedenheft et al., 2012. Nature 482:331-338). In the Type I-E system, as exemplified by *Escherichia coli*, crRNAs are incorporated into a multisubunit effector complex called Cascade (CRISPR-associated complex for antiviral defence) (Brouns et al., 2008. Science 321: 960-4), which binds to the target DNA and triggers degradation by the signature Cas3 protein (Sinkunas et al., 2011. EMBO J 30:1335-42; Beloglazova et al., 2011. EMBO J 30:616-27). In Type III CRISPR/Cas systems of *Sulfolobus solfataricus* and *Pyrococcus furiosus*, Cas RAMP module (Cmr) and crRNA complex recognize and cleave synthetic RNA in vitro (Hale et al., 2012. Mol Cell 45:292-302; Zhang et al., 2012. Mol Cell, 45:303-13) while the CRISPR/Cas system of *Staphylococcus epidermidis* targets DNA in vivo (Marraffini & Sontheimer, Science. 322:1843-5).

RNP complexes involved in DNA silencing by Type II CRISPR/Cas systems, more specifically in the CRISPR3/Cas system of *Streptococcus thermophilus* DGCC7710 (Horvath & Barrangou, 2010. Science 327:167-70), consists of four cas genes cas9, cas1, cas2, and csn2, that are located upstream of 12 repeat-spacer units (FIG. 1A). Cas9 (formerly named cas5 or csn1) is the signature gene for Type II systems (Makarova et al., 2011. Nat Rev Microbiol 9:467-77). In the closely related *S. thermophilus* CRISPR1/Cas system, disruption of cas9 abolishes crRNA-mediated DNA interference (Barrangou et al., 2007. Science 315:1709-12). We have shown recently that the *S. thermophilus* CRISPR3/Cas system can be transferred into *Escherichia coli*, and that this heterologous system provides protection against plasmid transformation and phage infection, de novo (Sapranauskas et al., 2011. Nucleic Acids Res 39:9275-82). The interference against phage and plasmid DNA provided by *S. thermophilus* CRISPR3 requires the presence, within the target DNA, of a proto-spacer sequence complementary to the spacer-derived crRNA, and a conserved PAM (Proto-spacer Adjacent Motif) sequence, NGGNG, located immediately downstream the proto-spacer (Deveau et al., 2008. J Bacteriol 190:1390-400; Horvath et al., 2008. J Bacteriol 190:1401-12; Mojica et al., 2009. Microbiology 155:733-40). Single point mutations in the PAM or defined proto-spacer positions allow the phages or plasmids to circumvent CRISPR-mediated immunity (Deveau et al., 2008. J Bacteriol 190:1390-400; Garneau et al., 2010. Nature 468:67-71; Sapranauskas et al., 2011. Nucleic Acids Res 39:9275-82). We have established that in the heterologous system, cas9 is the sole cas gene necessary for CRISPR-encoded interference (Sapranauskas et al., 2011. Nucleic Acids Res 39:9275-82), suggesting that this protein is involved in crRNA processing and/or crRNA-mediated silencing of invasive DNA. Cas9 of *S. thermophilus* CRISPR3/Cas system is a large multi-domain protein comprised of 1,409 aa residues (Sapranauskas et al., 2011. Nucleic Acids Res 39:9275-82). It contains two nuclease domains, a RuvC-like nuclease domain near the amino terminus, and a HNH-like nuclease domain in the middle of the protein. Mutational analysis has established that interference provided in vivo by Cas9 requires both the RuvC- and HNH-motifs (Sapranauskas et al., 2011. Nucleic Acids Res 39:9275-82).

Isolation of the Cas9-crRNA complex of the *S. thermophilus* CRISPR3/Cas system as well as complex assembly in vitro from separate components and demonstration that it cleaves both synthetic oligodeoxynucleotide and plasmid DNA bearing a nucleotide sequence complementary to the crRNA, in a PAM-dependent manner, is provided. Furthermore, we provide experimental evidence that the PAM is recognized in the context of double-stranded DNA and is critical for in vitro DNA binding and cleavage. Finally, we show that the Cas9 RuvC- and HNH-active sites are responsible for the cleavage of opposite DNA strands. Taken together, our data demonstrate that the Cas9-crRNA complex functions as an RNA-guided endonuclease which uses RNA for the target site recognition and Cas9 for DNA cleavage. The simple modular organization of the Cas9-crRNA complex, where specificity for DNA targets is encoded by a small crRNA and the cleavage machinery consists of a single, multidomain Cas protein, provides a versatile platform for the engineering of universal RNA-guided DNA endonucleases. Indeed, we provide evidence that by altering the RNA sequence within the Cas9-crRNA complex, programmable endonucleases can be designed both for in vitro and in vivo applications, and we provide a proof of concept for this novel application. These findings pave the way for the development of novel molecular tools for RNA-directed DNA surgery.

SUMMARY OF THE INVENTION

A method for the site-specific modification of a target DNA molecule through contacting under suitable conditions, a target polydeoxynucleotide molecule; and an RNA-guided DNA endonuclease comprising at least one RNA sequence and at least one of an RuvC active site motif and an HNH active site motif; to result in the target polydeoxynucleotide molecule modified in a region that is determined by the complimentary binding of the RNA sequence to the target DNA molecule is provided. The method includes incubating under suitable conditions a composition that includes a target double stranded polydeoxynucleotide or single stranded polydeoxynucleotide; wherein a double stranded polydeoxynucleotide contains a short proto-spacer adjacent motif (PAM), which is non-obligatory for a single stranded polydeoxynucleotide; and where PAM comprises a 5'-NGGNG-3' sequence; a polyribonucleotide (crRNA) comprising a 3' and 5' regions wherein the 3' region comprises at least 22 nt of the repeat present in a microbe containing CRISPR locus and 5'-region comprises of at least 20 nt of the spacer sequence immediately downstream of the repeat in the CRISPR locus, which is substantially complementary, optionally complementary, to a portion of the target polynucleotide, a polypeptide wherein the amino acid sequence of polypeptide and amino acid sequence of SEQ ID NO: 1 have at least 80% identity, isolated from S. thermophilus, or genetically modified microorganism, including a genetically modified E. coli, or wherein the polypeptide is produced by a method selected from recombinant DNA technology or chemical synthesis; a polyribonucleotide tracrRNA of nucleotide sequence SEQ ID NO: 5 (or have at least 80% identity) comprising a 5' and 3' regions wherein the 5' region is comprised of at least 22 nucleotides is complementary to the 22 nucleotides 3' region of crRNA, and 3' region. Wherein polyribonucleotides are produced by in vitro transcription or chemical synthesis. Wherein, suitable conditions means conditions in vitro or in vivo where reaction might occur.

A method for the conversion of Cas9 polypeptide into a nickase, cleaving only one strand of double-stranded DNA, by inactivating one of the active sites (RuvC or HNH) in the polypeptide by at least on point mutation, exemplified by D31A (SEQ ID NO: 2), N891A (SEQ ID NO: 3) and H868A (SEQ ID NO: 4) point mutations, is provided. RuvC motif mutant cleaves only bottom DNA strand in respect to 5'NGGNG-3' motif, while HNH motif mutant cleaves top strand.

Polypeptide-polyribonucleotides complex might be isolated from a genetically modified microbe (for example Escherichia coli or Streptoccocus thermophilus), or assembled in vitro from separate components. In the genetically modified microbe components of the complex might be encoded on the one, two or three separate plasmids containing host promoters of the genetically modified microbe or promoters from a native host genome.

A method for assembly of active polypeptide-polyribonucleotides complex in vitro, comprising incubating the components of the complex under conditions suitable for complex assembly is provided. The complex might be assembled using three or four components. Method for three components assembly comprises incubating the Cas9 polypeptide, 78 nt tracrRNA polyribonucleotide (SEQ ID NO: 5), and 42 nt crRNA polyribonucleotide (5'-NNNNNNNNNNNNNNNNNNNNGUUUUAGAGCU-GUGUUGUUUCG-3') (SEQ ID NO: 15) under conditions suitable for complex assembly. Method for four components assembly comprises incubating the Cas9 polypeptide; 102 nt tracrRNA polyribonucleotide (SEQ ID NO: 6); polyribonucleotide containing sequence 5'-NNNNNNNNNNNNNNNNNNNNGUUUUAGAGCU-GUGUUGUUUCG-3' (SEQ ID NO: 15) and flanking regions and RNase III polypeptide, cleaving double stranded RNA polynucleotide. The examples for polyribonucleotide containing sequence 5'-NNNNNNNNNNNNNNNNNNNNGUUUUAGAGCU-GUGUUGUUUCG-3' (SEQ ID NO: 15) are SEQ ID NO: 8, SEQ ID NO: 9, SEQ ID NO: 10, SEQ ID NO: 11 and SEQ ID NO: 12). Examples of source for suitable RNaseIII include Escherichia coli or Streptococcus thermophilus.

A method for re-programming of a Cas9-crRNA complex specificity by mixing separate components or using a cassette containing a single repeat-spacer-repeat unit is provided. Any sequence might be inserted between two repeats in the cassette using suitable restriction endonucleases. Cassette might be used to target sequences in vivo, or to produce RNA ribonucleotide suitable for complex assembly in vitro.

BRIEF DESCRIPTION OF THE FIGURES

FIG. 4(B) discloses SEQ ID NOS 50, 50-51, and 52, 52-53, respectively, in order of appearance. (C) Comparison of crRNA sequences. The sequence and length of S. pyogenes crRNA was determined by deep sequencing analysis (2). The approximate length of crRNA from S. thermophilus LMD-9 (2) and DGCC7710 (this work) strains were determined by the northern blot analysis. FIG. 4(C) discloses SEQ ID NOS 54-56, respectively, in order of appearance.

FIG. 5(A) discloses SEQ ID NOS 31, 7, and 34, respectively, in order of appearance. (B) Oligoduplex SP1 cleavage. 2.5 nM of Cas9-crRNA complex and 1 nM SP1 oligoduplex labeled with 33P at the 5'-end of either (+) or (−)strand were incubated in the reaction buffer (10 mM Tris-HCl pH=7.5, 10 mM NaCl, 10 mM MgCl2, 0.1 mg/ml BSA) at 37° C. for varied time intervals (30 s to 10 min) and reaction products analysed in the 20% PAA gel. Lanes M1 and M2 contain chemically synthesized 5'-end 33P-labeled 37 nt and 18 nt oligodeoxynucleotides corresponding to the cleavage products of (−) and (+) DNA strands, respectively. Cleavage positions are designated by arrows. FIG. 5(B) discloses SEQ ID NO: 31. (C) Schematic representation of pSP1 plasmid (Sapranauskas et al., 2011. Nucleic Acids Res 39:9275-82) used in the plasmid cleavage assay. FIG. 5(C) discloses SEQ ID NO: 57. (D) pSP1 plasmid cleavage. Agarose gel analysis of pSP1 cleavage products (left panel). SC—super-coiled plasmid DNA, OC—open circular DNA nicked at one of the strands, FLL—full length linear DNA cut at both strands. Final reaction mixtures at 37° C. contained 2.5 nM of pSP1 plasmid and 2.5 nM of Cas9-crRNA complex in the reaction buffer (section B). Direct sequencing electropherograms (right panel) of (+) (upper part) and (−) (lower part) strands of pSP1 plasmid cleavage product. The non-templated addition of adenine (T in the reverse complement sequence shown here) at the extremity of sequence is a sequencing artefact caused by the polymerase. FIG. 5(D) discloses SEQ ID NOS 58, 59, 58, and 60, respectively, in order of appearance.

FIG. 7 shows reprograming of Cas9-crRNA complex. (A) Schematic representation of heterologous loci in two plasmids used for reprogramming of Cas9-crRNA complex. pCas(−)SPN were constructed from pCas9(−) plasmid (See FIG. 2A), by inserting new spacer sequence (SN) (5'-CC ACC CAG CAA AAT TCG GTT TTC TGG CTG-3' (SEQ ID NO: 16)) and inactivating Cas9 gene as described in (1). (B) Agarose gel analysis of plasmid DNA cleavage products. pSP1 and pSP1+SPN (pSP1 plasmid with inserted new proto-spacer and PAM over AatII site were incubated at 2.5 nM concentration with 2 nM of Cas9-crRNA complex in the reaction buffer (10 mM Tris-HCl pH=7.5, 10 mM NaCl, 10 mM MgCl2, 0.1 mg/ml BSA) at 37° C. for varied time intervals and reaction products analysed in the agarose gel. SC—super-coiled plasmid DNA, OC—open circular DNA nicked at one of DNA strands, FLL—full length linear DNA cut at both strands. (C) Oligoduplex SP1 cleavage. 2.5 nM of Cas9-crRNA complex and 1 nM SPN oligoduplex (Table S2) labeled with 33P at the 5'-end of either (+) or (−)strand were incubated in the reaction buffer (10 mM Tris-HCl pH=7.5, 10 mM NaCl, 10 mM MgCl2, 0.1 mg/ml BSA) at 37° C. M1-18 nt length marker Lanes M1 and M2 contain chemically synthesized 5'-end 33P-labeled 18 nt and 37 nt oligodeoxynucleotides corresponding to the cleavage products of (+) and (−) DNA strands, respectively. (D) Schematic representation of SPN oligoduplex substrate and cleavage products. SPN oligoduplex contains the new proto-spacer (red letters), PAM (blue letters). Cleavage positions are designated by arrows. FIG. 7(D) discloses SEQ ID NO: 39.

FIG. 8 shows impact of spacer length on CRISPR-encoded immunity. (A) Schematic representation of shortened versions of proto-spacers inserted in the transformed plasmids. FIG. 8(A) discloses SEQ ID NOS 7 and 61-66, respectively, in order of appearance. (B) Effect of proto-spacer length on the plasmid transformation efficiency. Transformation efficiency is expressed as cfu per nanogram of plasmid DNA (mean±SD). (C). Schematic representation of oligoduplexes used in the in vitro cleavage and binding experiments. FIG. 8(C) discloses SEQ ID NOS 31 and 38, respectively, in order of appearance. (D) Time courses of the 27 bp oligoduplex (full length protospacer SP1, filled circles) and the 20 bp oligoduplex (truncated protospacer SP1-20, square) cleavage by the Cas9-crRNA complex. (E) Electrophoretic mobility shift assay of SP1 and SP1-20 oligoduplex binding by the Cas9-crRNA complex.

FIG. 11(C) discloses SEQ ID NOS 31. (D) Strand preference of N891A mutant. N891 mutant cleaves only (−)strand of SP1 oligoduplex. Cleavage positions are designated by arrows. FIG. 11(D) discloses SEQ ID NOS 31.

FIG. 12(A) discloses SEQ ID NOS 58, 59, 58, and 58, respectively, in order of appearance. (B) Direct sequencing of reaction products obtained with Cas9 N891A mutant (HNH-like active site motif). FIG. 12(B) discloses SEQ ID NOS 58, 58, 58, and 60, respectively, in order of appearance. (C) SP1 oligoduplex binding by the wt Cas9-crRNA and active site mutant complexes. (D) Cleavage of (+)SP1 strand by Cas9-crRNA mutant complexes.

FIG. 14 discloses SEQ ID NOS. 31 and 7, respectively, in order of appearance.

strand which were used to determine the size of the cleavage products and map the cleavage position. Cas9 protein cleaves both strands of oligoduplex inside the proto-spacer, after the 37th nucleotide, 3 nt upstream of the PAM (5'-NGGNG-3') leaving blunt ends. Both strands of non-specific substrate (K1 and K2) are not cleaved when incubated with Cas9-crRNA complex for 30 min. FIG. 17 discloses SEQ ID NO: 31.

FIG. 19 discloses SEQ ID NO: 31.

Figure 1:
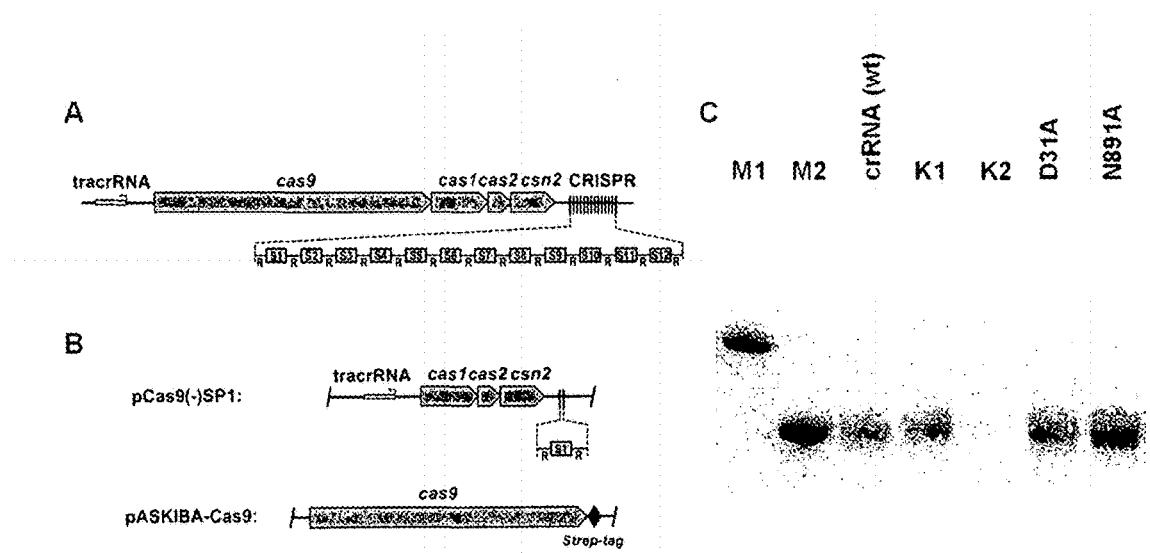
FIG. 1 shows Cas9 protein co-purifies with crRNA. (A) Schematic representation of CRISPR3/Cas system of S. thermophilus. Four cas genes (cas9, cas1, cas2, csn2) are located upstream of the CRISPR repeat-spacer array, consisting of 13 repeat (R) sequences and 12 unique spacers (S1-S12). The tracrRNA, required for crRNA maturation in Type II CRISPR systems (Deltcheva et al., 2011. Nature 471:602-7), is located upstream the cas9 gene and encoded on the opposite DNA strand (showed by an arrow) in respect to the other elements of CRISPR3/Cas system. (B) Schematic representation of heterologous loci in two plasmids used for the co-expression of the Cas9-crRNA complex. E. coli RR1 strain contained pCas9(-)1SP (encoding Cas1, Cas2, Csn2, SP1 and tracrRNA) and pASKIBA-Cas9 (encoding Strep-tagged version of Cas9) plasmids. (C) Northern analysis of Cas9-crRNA complexes using anti-crDNA oligonucleotide as a probe. M1-84 nt oligodeoxynucleotide corresponding to the spacer S1-repeat unit; M2-42 nt synthetic oligoribonucleotide corresponding to the predicted S. thermophilus CRISPR3 crRNA (See FIG. 4); crRNA (wt)—crRNA isolated from the wt Cas9 complex; K1—crRNA (wt) treated with Dnase I for 15 min; K2—crRNA (wt) treated with RNaseI for 15 min, D31A—crRNA purified from the Cas9 D31A mutant complex; N891A—crRNA purified from the Cas9 N891A mutant complex.

The following non-limiting examples further describe the methods, compositions, uses, and embodiments.

DETAILED DESCRIPTION OF ILLUSTRATIVE EMBODIMENTS

Example 1

In this example, we have isolated the Cas9-crRNA complex of *S. thermophilus* CRISPR3/Cas system and demonstrate that it cuts in a PAM dependent manner both synthetic oligodeoxynucleotide and plasmid DNA bearing a nucleotide sequence complementary to the crRNA. Furthermore, we provide experimental evidence that PAM is recognized in the context of double-stranded DNA and is critical for in vitro DNA binding and cleavage. Finally, we show that RuvC and HNH-motifs of Cas9 contribute to the cleavage of opposite DNA strands. Taken together, our data demonstrate that Cas9-crRNA complex functions as RNA-guided endonuclease which uses RNA module for the target site recognition and employs two separate active sites in the protein module for DNA cleavage. These findings pave the way for engineering of programable Cas9-crRNA complexes as universal RNA-guided endonucleases.

Materials and Methods

DNA manipulations. Genomic DNA of *Streptococcus thermophilus* DGCC7710 strain was used as a template in PCR reactions to clone cas9. To generate a pASKIBA3-Cas9 plasmid which was used for the expression of the C-terminal Strep-tagged Cas9 protein variant, PCR fragment amplified with following primers: 5'-ACGTCTCAAATGTTGTT-TAATAAGTGTATAATAATTTC-3' (SEQ ID NO: 21) and 5'-ACGTCTCCGCGCTACCCTCTCCTAGTTTG-3' (SEQ ID NO: 22) was cloned into the pASK-IBA3 expression vector via Esp3I sites. To generate a pBAD-Cas9 plasmid which was used for the expression of the C-terminal 6× His-tagged Cas9 protein variant ("6× His" disclosed as SEQ ID NO: 23), PCR fragment amplified with the following primer pair: 5'-ACGTCTCACATGACTAAGCCATACT-CAATTGGAC-3' (SEQ ID NO: 24) and 5'-ACTCGAGAC-CCTCTCCTAGTTTGGCAA-3' (SEQ ID NO: 25) was cloned into the pBAD24-Chis expression vector via NcoI and XhoI sites. Full sequencing of cas9 gene in pASKIBA3-Cas9 and pBAD-Cas9 plasmids revealed no difference with the original cas9 sequence. To obtain plasmids pCas9(−)SP1 (FIG. 1B) and pCRISPR3-SP1 (FIG. 2A), bearing a single spacer1, PCR fragment amplified from pCRISPR3 plasmid with the following primer pair:5' GACCACTTATTGAGG-TAAATGAG 3' (SEQ ID NO: 26)/5' CAAACCAGGATC- CAAGCTAATACAGCAG-3' (SEQ ID NO: 27) ((BamHI (GGATCC) sites is underlined) was cloned into pCas9(−) and pCRISPR3 plasmids (Sapranauskas et al., 2011. Nucleic Acids Res 39:9275-82), respectively.

Expression and purification of Cas9 protein and Cas9-crRNA complex. 6× His-tagged ("6× His" disclosed as SEQ ID NO: 23) version of Cas9 protein was expressed and purified using a scheme described for the Cas3 protein from *S. thermophilus* CRISPR4/Cas system (Sinkunas et al., 2011. EMBO J 30:1335-42). For purification of the Cas9-crRNA complex, Strep-tagged version of the Cas9 protein was expressed in *E. coli* RR1 strain, bearing pCas9(−)SP1 plasmid (FIG. 1B). LB broth was supplemented with Ap (100 µg/ml) and Cm (10 µg/ml). *E. coli* cells for the Cas9-crRNA complex isolation were grown in two steps. First, 4 ml of cells culture were grown at 37° C. to OD600 of ~0.5, and expression induced by adding 0.2 µg/ml of anhydrotetracycline (AHT) (Sigma). After for 4 h, 1/400 of the pre-induced culture was inoculated into fresh LB medium supplemented with Ap (100 µg/ml), Cm (12 µg/ml) and AHT (0.2 µg/ml) and was grown at 37° C. overnight. Harvested cells were disrupted by sonication and cell debris removed by centrifugation. The supernatant was loaded onto the 1 ml StrepTrap HP column (GE Healthcare) and eluted with 2.5 mM of desthiobiotin. Approximately 1.5 µg of the Cas9 protein was obtained in a single run from 1 L of *E. coli* culture. The fractions containing Cas9 were stored at +4° C. for several days. The homogeneity of protein preparations was estimated by SDS-PAGE. Protein concentrations in the Cas9-crRNA complexes were determined by densitometric analysis of SDS-PAGE gels containing samples of Strep-Tactin purified Cas9 proteins along with known amounts of His-tagged Cas9 protein. The concentration of the Cas9-crRNA complexes is expressed as Cas9 protein concentration assuming that Cas9 is a monomer and binds crRNA in a complex with 1:1 stoichiometry.

Northern blot analysis. Cas9-bound RNA was isolated from Strep-Tactin purified Cas9, co-expressed with pCas9(−)SP1 plasmid using the miRNeasy Mini kit (Qiagen). Northern blots were performed by running RNA on a 10% polyacrylamide gel with 7 M urea in 20 mM MOPS/NaOH pH 8 buffer. The RNA was transferred to a SensiBlot™ Plus Nylon Membrane (Fermentas) by semi-dry blotting using a Trans-blot SD (Bio-Rad). RNA was cross-linked to the membrane with 0.16 M I-ethyl-3-(3-dimethylaminopropyl) carbodiimide (EDC) (Pierce)/0.13 M 1-methylimidazole (Sigma) pH 8 at 60° C. for 1 h. The membrane was pre-hybridized with 2×SSC buffer containing 1% SDS and 0.1 mg/ml denatured DNA from fish testes (Ambion) for 1 h at 40° C. Blots were probed for 12 h with a $^{32}$P-5'-labelled 42 nt anti-crRNA DNA oligonucleotide containing 20 nt of spacer1 and 22 nt of the repeat sequence (5'-TC-GAAACAACACAGCTCTAAAACTGTCCTCTTC-CTCTTTAGC-3' (SEQ ID NO: 28)). The blots were washed 3× for 15 min with 0.2×SSC buffer containing 0.2% SDS, and were visualized using phosphorimaging. A 42, nt synthetic oligoribonucleotide (5'-CGCUAAAGAGGAAGAG-GACAGUUUUAGAGCUGUGUUGUUUCG-3' (SEQ ID NO: 7)) and 84 nt DNA oligonucleotide.

Oligonucleotide substrates. All oligonucleotide substrates used in this study are given in Table 1. Oligodeoxyribo-nucleotides were purchased from Metabion (Martinsried, Germany). The 5'-ends of oligonucleotides were radiolabelled using PNK (Fermentas) and [γ-33P]ATP (Hartmann Analytic). Duplexes were made by annealing two oligonucleotides with complementary sequences (SP1, SP1-Δp, SP2). Radioactive label was introduced at the 5' end of individual DNA strand prior to the annealing with unlabelled strand.

Reactions with oligonucleotide substrates. Reactions were typically carried out by adding 2 nM of Cas9-crRNA complex to 1 nM labeled oligonucleotide in 10 mM Tris-HCl (pH 7.5 at 37° C.), 10 mM NaCl, 0.1 mg/ml BSA and 10 mM MgCl2 at 37° C. Aliquots were removed at timed intervals and quenched with loading dye (95% v/v formamide, 0.01% bromphenol blue, 25 mM EDTA, pH 9.0) and subjected to denaturing gel electrophoresis through 20% polyacrylamide followed by a FLA-5100 phosphorimager (Fujilm) detection.

Reactions with plasmid substrates. Reactions on pUC18 plasmid and its derivatives (Sapranauskas et al., 2011. Nucleic Acids Res 39:9275-82) were conducted at 37° C. in the buffer used for reactions on oligonucleotide substrates. Reaction mixtures typically contained 2.5 nM supercoiled plasmid and 2 nM of Cas9-crRNA complex. The reactions were initiated by adding protein to the mixture of the other components. Aliquots were removed at timed intervals and quenched with phenol/chloroform. The aqueous phase was mixed with loading dye solution (0.01% bromphenol blue and 75 mM EDTA in 50% v/v glycerol) and analyzed by electrophoresis through agarose.

Plasmid cleavage position determination. To achieve complete cleavage of plasmid substrate, 8 nM of Cas9-crRNA complex was incubated with 2.5 nM of supercoiled plasmid in the reaction buffer at 37° C. for 10 min. Reaction products were purified and concentrated using GeneJET PCR Purification Kit (Fermentas). Spacer1 surrounding region of Cas9 linearized and nicked plasmids were directly sequenced with the following primers: 5'-ccgcatcaggcgccat-tcgcc-3' (SEQ ID NO: 29) (sequencing of (+)strand) and 5'-gcgaggaagcggaagagcgccc-3' (SEQ ID NO: 30) (sequencing of (−)strand).

Binding assay. Increasing amounts of protein-crRNA complex were mixed with 0.5 nM of $^{33}$P-labeled double-stranded and single-stranded DNA substrates (Table 1) in the binding buffer (40 mM Tris-acetate, pH 8.3 at 25 C, 0.1 EDTA, 0.1 mg/ml BSA, 10% v/v glycerol) and incubated for 15 min at room temperature. Free DNA and protein-DNA complexes were separated on the non-denaturing 8% polyacrylamide gel (ratio of acrylamide/N,N'-methylenebisacrylamide 29:1) using 40 mM Tris-acetate (pH 8.3) supplemented with 0.1 mM EDTA as the running buffer. Electrophoresis was run at room temperature for 3 h at 6 V/cm.

Mutagenesis. The mutants D31A and N891A were obtained by the site-directed mutagenesis as previously described (Tamulaitis et al., 2007. Nucleic Acids Res 35:4792-9). Sequencing of the entire gene for each mutant confirmed that only the designed mutation had been introduced.

TABLE 1

Oligonucleotide substrates. Proto-spacer sequence is underlined, PAM is on bold.

| Oligonucleotide | Sequence | Specification |
|---|---|---|
| SP1 (SEQ ID NO: 31) | 5'-GCTCGAATTGAAATTCTAAACGCTAAAGAGGAA GAGGACATGGTGAATTCGTAAT-3' 3'-CGAGCTTAACTTTAAGATTTGCGATTTCTCCTT CTCCTGTACCACTTAAGCATTA-5' | 55 bp oligoduplex substrate containing proto-spacer1 and PAM |
| SP1-pΔ (SEQ ID NO: 32) | 5'-GCTCGAATTGAAATTCTAAACGCTAAAGAGGAA GAGGACAAATTCGTAAT-3' 3'-CGAGCTTAACTTTAAGATTTGCGATTTCTCCTT CTCCTGTTTAAGCATTA-5' | 50 bp oligoduplex substrate containing proto-spacer2 |
| SP2 (SEQ ID NO: 33) | 5'-GCTCGAATTGTACTGCTGTATTAGCTTGGTTGT TGGTTTGTGGTGAATTCGTAAT-3' 3'-CGAGCTTAACATGACGACATAATCGAACCAACA ACCAAACACCACTTAAGCATTA-5' | 55 bp oligoduplex substrate containing proto-spacer2 and PAM (oligodublex without proto-spacer1) |
| s(+) SP1 (SEQ ID NO: 34) | 5'-ATTACGAATTCACCATGTCCTCTTCCTCTTTAG CGTTTAGAATTTCAATTCGAGC-3' | 55 nt ssDNA oligonucleotide substrate (+) strand of SP1 oligoduplex |
| s(+) SP1-pΔ (SEQ ID NO: 35) | 5'-ATTACGAATTTGTCCTCTTCCTCTTTAGCGTTT AGAATTTCAATTCGAGC-3' | 50 nt ssDNA oligonucleotide substrate (+) trand of SP1-pΔ oligoduplex |
| s(+) SP2 (SEQ ID NO: 36) | 5'-ATTACGAATTCACCACAAACCAACAACCAAGCT AATACAGCAGTACAATTCGAGC-3' | 55 nt ssDNA oligonucleotide substratate (+) strand of SP2 oligoduplex |
| s(-) SP1 (SEQ ID NO: 37) | 5'-GCTCGAATTGAAATTCTAAACGCTAAAGAGGA AGAGGACATGGTGAATTCGTAAT-3' | 55 nt ssDNA oligonucleotide substrate, (-) strand of SP1 oligoduplx |
| SP1-20 (SEQ ID NO: 38) | 5'-GCTCGAATTGCGCTAAAGAGGAAGAGGACATG GTGAATTCGTAAT-3' 3'-CGAGCTTAACGCGATTTCTCCTTCTCCTGTAC CACTTAAGCATTA-5' | 45 nt oligoduplex substrate containing 20 nt of proto-spacer1 and PAM |
| SPN (SEQ ID NO: 39) | 5'-GCTCGAATTGCCACCCAGCAAAATTCGGTTTT CTGGCTGATGGTGAATTCGTAAT-3' 3'-CGAGCTTAACGGTGGGTCGTTTTAAGCCAAAA GACCGACTACCACTTAAGCATTA-5' | 55 bp oligoduplex substrate containing proto-spacerN and PAM |

Results

Figure 2:
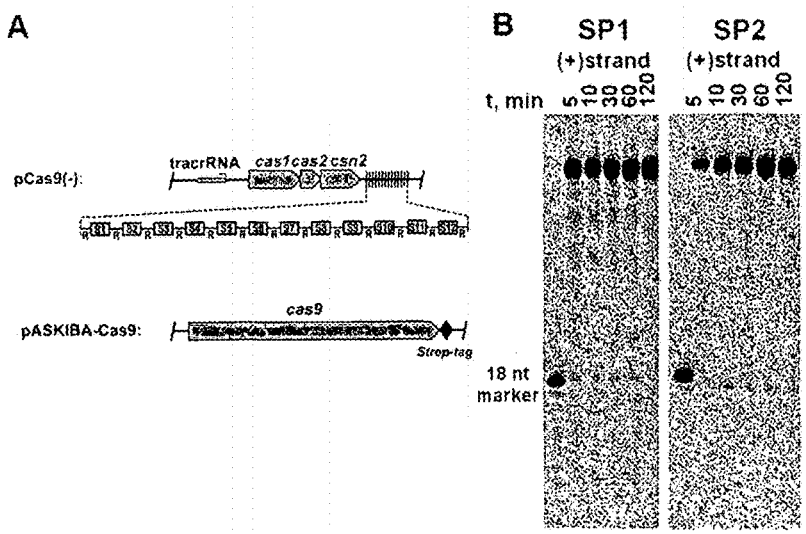
FIG. 2 shows DNA cleavage by Cas9-crRNA complexes obtained by Cas9 co-expression with full length CRISPR locus. (A) Schematic representation of CRISPR/Cas locus of recombinant pCas9(-) plasmid carrying indigenous 12 spacer-repeat array of SthCRISPR3/Cas system and pASKIBA-Cas9 plasmid carrying cas9 gene with a Strep-tag at the C-terminus. (B) Oligoduplex cleavage assay. Both pCas9(-) and pASKIBA-Cas9 plasmids were co-expressed in E. coli, Cas9-crRNA complexes were purified and subjected to cleavage analysis using SP1 (first proto-spacer) and SP2 (second proto-spacer) oligoduplexes labeled with 33P at the 5'-end of the (+) strand. Reaction products were analysed on PAA gel.

Expression and purification of the Cas9-crRNA complex. The cas9 gene from the CRISR3 system of S. thermophilus DGCC7710 strain was cloned into the pASK-IBA3 vector to produce a construct encoding a Cas9 protein fusion containing a C-terminal Strep(II)-tag (FIG. 1B). Initially, we have tried to purify Cas9-crRNA complex from E. coli strain RR1 expressing Cas9 protein on the pASK-IBA3 vector and other Cas proteins (except Cas9) on pCas9(-) plasmid (Sapranauskas et al, 2011). pCas9(-) also contained a complete CRISPR3 array comprised of 12 spacer-repeat units (FIG. 2A). To achieve simultaneous transcription of all target genes we performed cas9 gene expression in two steps. First, we induced Cas9 expression in a small volume of E. coli culture and after 4 h transferred an aliquot of pre-induced culture into a larger volume of fresh LB media already containing inductor and incubated overnight. Cas9 protein complex was purified from the crude cell extract using Strep-Tactin Sepharose. We managed to isolate a small amount of the Cas9-crRNA complex which showed only traces of nucleolytic activity on the oligoduplex SP1 containing a proto-spacer1 and PAM. We assumed that low cleavage activity could be due to the intrinsic heterogeneity of Cas9-crRNA complexes resulting from the transcription of 12 spacer-repeat units. If all spacer-repeat units are uniformly transcribed into a mature crRNA, the concentration of the Cas9 complex containing crRNA against spacer-1 will make ¹/₁₂th fraction of the total Cas9-crRNA concentration. The cleavage activity of the Cas9-crRNA preparation against the SP2 oligoduplex containing a proto-spacer-2 and PAM is consistent with the heterogeneity of Cas9-crRNA complexes (FIG. 2B). To increase the yield of the specific Cas9-crRNA complex we engineered a pCas9(-)SP1 plasmid which contains a single R-spacer1-R unit in the CRISPR array (FIG. 1B). Plasmid transformation interference assay confirmed that the CRISPR3/Cas system carrying a single spacer1 prevents plasmid pSP1 transformation in E. coli with the same efficiency as the CRISPR3/Cas system carrying a complete CRISPR region (FIG. 3B). We have isolated Cas9-crRNA complex following the procedure described above and analysed crRNA bound to Cas9 protein.

Figure 3:
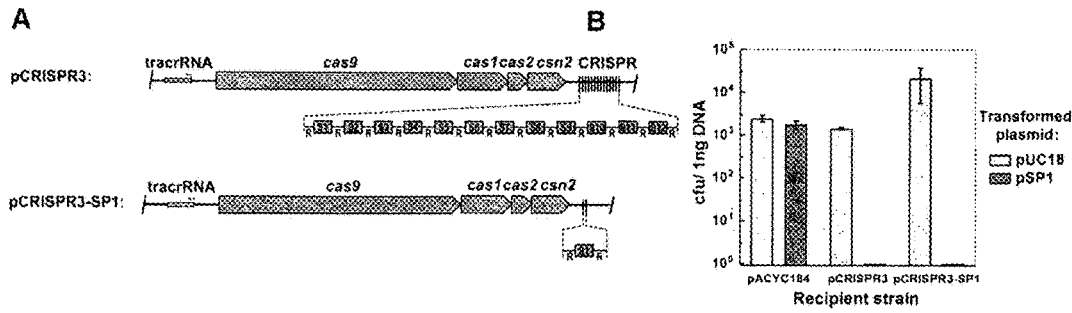
FIG. 3 shows immunity against plasmid transformation in E. coli cells provided by the SthCRISPR3/Cas system. (A) Schematic representation of CRISPR/Cas locus of recombinant plasmid pCRISPR3 carrying indigenous 12 spacer-repeat array of SthCRISPR3/Cas system and engineered pCRISPR3-SP1 plasmid carrying 1 spacer-repeat unit. (B) Interference of plasmid transformation by SthCRISPR3/Cas system in E. coli cells. Escherichia coli RR1 recipient strains carrying plasmids pACYC184, pCRISPR3 or pCRISPR3-SP1, were transformed with plasmid pSP1 carrying proto-spacers and PAM or pUC18 (1). Transformation efficiency is expressed as cfu per nanogram of plasmid DNA (mean±SD).
Figure 4:
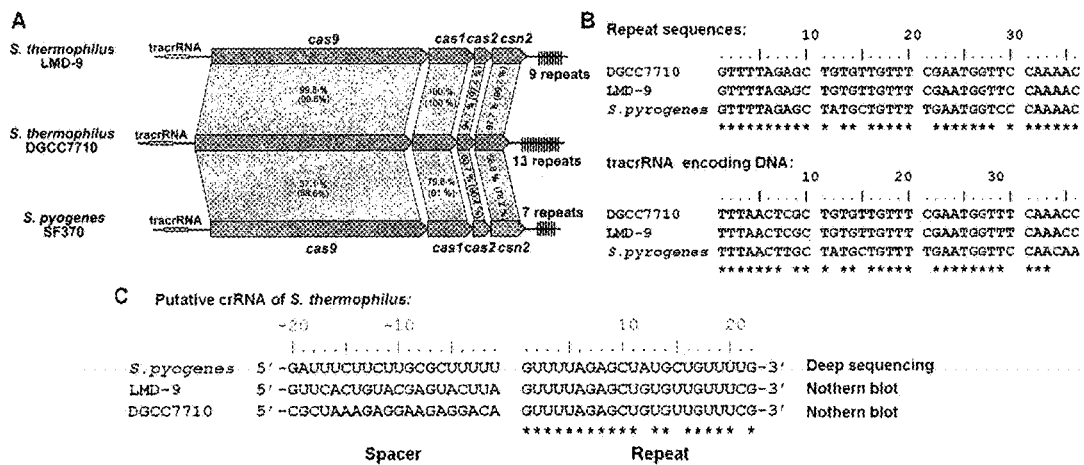
FIG. 4 shows comparison of Type IIA CRISPR/Cas systems from S. thermophilus DGCC7710, LMD-9 and S. pyogenes SF370 strains. (A) Schematic organization of the CRISPR/Cas systems. Nucleotide sequences corresponding to the tracrRNA required for the crRNA maturation in of S.pyogenes (2) are present in LMD-9 and DGCC7710. Percentage of identical and similar (in parenthesis) residues between corresponding protein sequences that are connected by dashed lines. (B). Alignment of the conserved repeat sequences and tracrRNA. Corresponding sequences from DGCC7710 and LMD-9 are identical. Nucleotide positions which are identical in all three strains are labeled with an asterisk below aligned sequences.

Cas9 protein co-purifies with crRNA. CRISPR3/Cas system of S. thermophilus belongs to the Type IIA subtype (former Nmeni or CASS4) of CRISPR/Cas systems (Makarova et al., 2011. Nat Rev Microbiol 9:467-77). It has been shown that in the Type IIA CRISPR/Cas system of Streptococcus pyogenes trans-encoded small RNA (tracrRNA) and bacterial RNaseIII are involved in the generation of crRNA (Deltcheva et al., 2011. Nature 471:602-7). Streptococcus pyogenes crRNA is only 42 nt in length and has no "5'-handle" which is conserved in crRNA's from Type I and III CRISPR systems (Hale et al., 2009. Cell 139:945-56; Jore et al., 2011. Nat Struct Mol Biol 18:529-36). According to the northern blot analysis crRNA of similar length is generated in the S. thermophilus LMD-9 CRISPR3/Cas system (Makarova et al., 2011. Nat Rev Microbiol 9:467-77), which is almost identical to the CRISPR3/Cas system of DGCC7710 strain (FIGS. 4A and B). We assumed that crRNA isolated from the Cas9-crRNA complex expressed in the heterologous E. coli strain (FIG. 1) may have the same length (FIG. 4). Therefore, to probe nucleic acids extracted from the Strep-Tactin purified Cas9 complex we used 42 nt anti-crRNA DNA oligonucleotide comprised of 22 nt region corresponding to the 3'-end of the repeat sequence and 20 nt at the 5'-end of SP1 fragment. Nucleic acid present in the Cas9 complex hybridized with anti-crRNA oligonucleotide, and was sensitive to RNAse but not DNAse treatment (FIG. 1C). The size of extracted crRNA was identical to the 42 nt synthetic oligoribonucleotide corresponding to the putative crRNA of the CRISPR3 system of *S. thermophilus* DGCC7710 strain (FIG. 3A, FIG. 4C). Taken together, these data confirm that Cas9 Strep-tag protein co-purifies with 42 nt crRNA, which is derived from CRISPR3 region.

Figure 5:
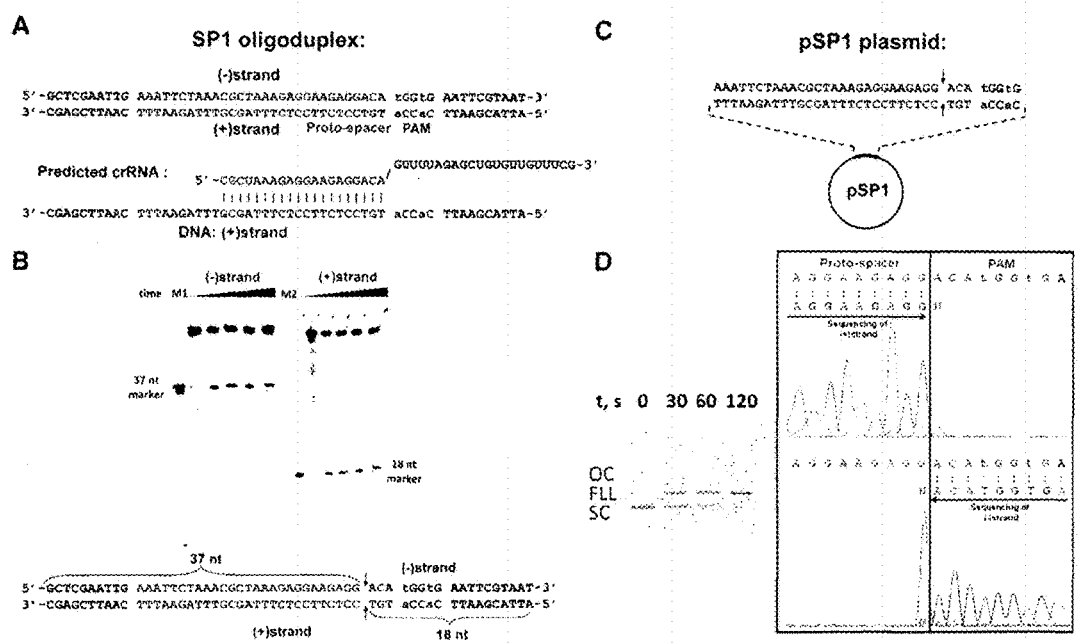
FIG. 5 shows Cas9-crRNA complex cleaves in vitro double-stranded DNA within a proto-spacer. (A) Oligoduplex substrate used in the cleavage assay. 55 nt oligoduplex SP1 contains the proto-spacer1 (red letters), PAM (blue letters) and 10 nt flanking sequences on both sides identical to those in pSP1 plasmid. In the SP1 oligoduplex DNA strand complimentary to the 5'-terminal fragment of crRNA (red letters) is named (+)strand, an opposite DNA strand is named (−)strand.
Figure 6:
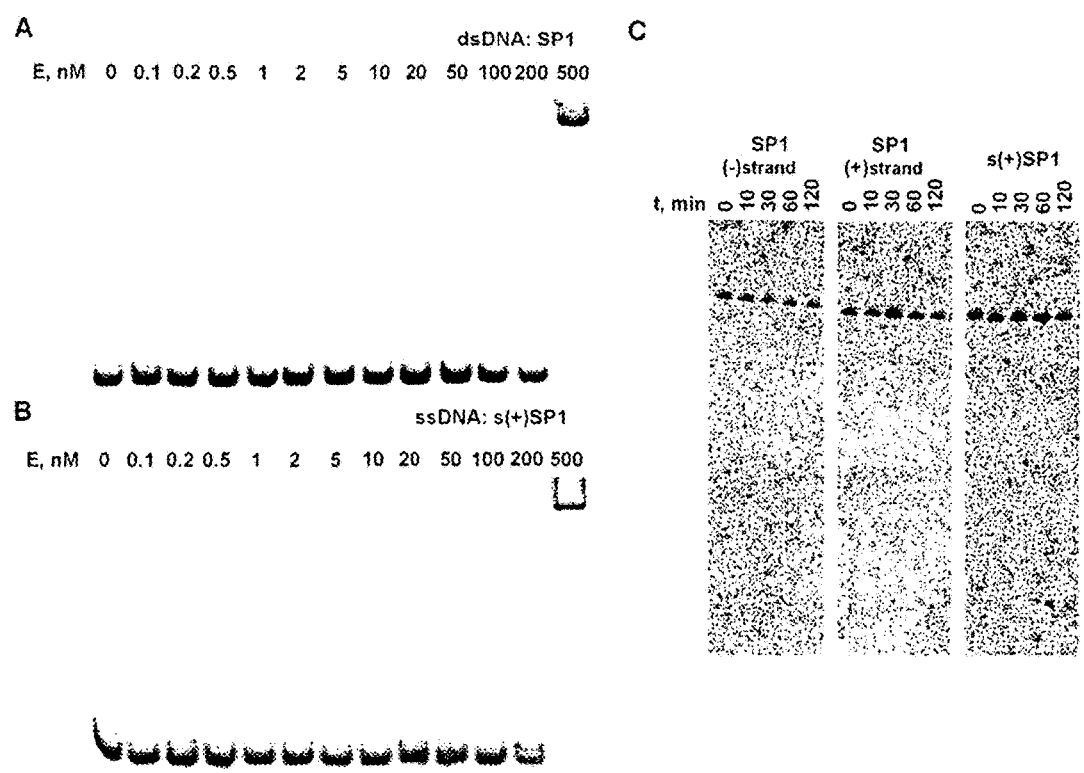
FIG. 6 shows DNA binding and cleavage analysis of Cas9-Chis protein lacking crRNA. Electrophoretic mobility shift analysis (EMSA) of Cas9-Chis protein binding to (A) the double stranded SP1 oligoduplex and (B) the single stranded s(+)SP1 oligonucleotide. Electrophoretic mobility shift experiments were performed in the binding buffer (40 mM Tris-acetate, pH 8.3 at 25 C, 0.1 EDTA, 0.1 mg/ml BSA, 10% v/v glycerol). The reactions contained 0.5 nM of the 33P-labelled oligoduplex, and the protein at concentrations as indicated above each lane. (C). Oligonucleotide cleavage assay. 5 nM of Cas9-Chis protein was incubated in the reaction buffer (10 mM Tris-HCl, pH=7.5, 10 mM NaCl, 10 mM MgCl2, 0.1 mg/ml BSA) at 37° C. with 1 nM oligonucleotide. SP1 oligoduplex was labeled with 33P at the 5'-end of the (+) or (−) strand. Single stranded oligonucleotide s(+)SP1 was labeled with 33P at the 5'-end.

Cas9 protein cleaves double-stranded DNA within a proto-spacer. To test in vitro activity of purified Cas9-crRNA complex we first used the SP1 oligoduplex (Table 1) containing the proto-spacer sequence identical to spacer SP1 in the CRISPR3 array, the PAM sequence 5'-TGGTG-3' downstream of the proto-spacer, and 10 nt flanking sequences from pSP1 plasmid (Sapranauskas et al., 2011. Nucleic Acids Res 39:9275-82) (FIG. 5A). The oligoduplex strand complementary to crRNA is named (+)strand, while the opposite duplex strand is called the ( )strand. To monitor cleavage reaction either (+) or (−)strand of the SP1 oligoduplex was P33-labeled at the 5'-terminus. Data shown in FIG. 5B demonstrate that the Cas9-crRNA complex cleaves both strands of oligoduplex at fixed position. Mapping of the cleavage position using synthetic oligonucleotides as size markers revealed that the Cas9-crRNA complex cuts both strands of the SP1 oligoduplex within the proto-spacer 3 nt upstream of the PAM (FIG. 5B) leaving blunt ends. It is worth to note, that no cleavage is observed after the 2 h incubation of the SP1 oligoduplex with the Cas9 protein lacking crRNA (FIG. 6C).

To test whether the Cas9-crRNA complex can locate the proto-spacer and cut DNA in vitro in long DNA substrates mimicking in vivo invading foreign DNA we analyzed cleavage of pSP1 plasmid (Sapranauskas et al., 2011. Nucleic Acids Res 39:9275-82) (FIG. 5C) carrying proto-spacer1 and PAM. In the presence of Cas9-crRNA complex supercoiled form of pSP1 plasmid was converted into a linear form (FIG. 5D), while pUC18 plasmid lacking proto-spacer1 was not cleaved. This means that both strands of the pSC1 plasmid were cleaved specifically within the proto-spacer region. We used direct sequencing to determine the ends of linear DNA form formed after the Cas9-crRNA cleavage. Sequencing results confirmed that cleavage of plasmid DNA occurred 3 nt away from 5'-NGGNG-3' PAM sequence similarly to the SP1 oligoduplex cleavage (FIG. 5D). The cleavage positions identified in the in vitro experiments (FIG. 4) for the CRISPR3/Cas system of *S. thermophilus* are identical to those determined in the in vivo cleavage experiments for the CRISPR1/Cas system in *S. thermophilus* (Garneau et al., 2010. Nature 468:67-71). To check if Cas9-crRNA induced cleavage occurs at the same position in other proto-spacer sequences, we analysed cleavage of the SP2 oligoduplex carrying a protospacer-2 and PAM sequences by the heterogeneous Cas9-crRNA complex isolated from the host carrying 12 spacer-repeat units. We have found that this heterogeneous Cas9-crRNA complex cuts (+)strand of SP2 oligoduplex exactly at the same position as in the SP1 oligoduplex.

Cas9-crRNA cleavage specificity is directed by the crRNA sequence. To demonstrate directly that Cas9-crRNA complex specificity can be re-programmed by changing crRNA in the ribonucleoprotein complex we inserted a new spacer (SN) instead of spacer S1 in the CRISPR region generating pCas(−)SN plasmid containing only a minimal CRISPR region and tracrRNA encoding sequence (FIG. 7), co-expressed this plasmid together with pASKIBA-Cas9 and purified Cas9-crRNA complex. The cleavage specificity of Cas9-crRNA complex was analysed using plasmids pSP1+SPN and pSP1 pSP1+SPN plasmid containing the proto-spacer sequence matching the SN spacer in the CRISPR region, was linearized by the Cas9-crRNA complex, while pSP1 plasmid which lacks complimentary sequence remained intact (FIG. 7B). To determine the cleavage position within the SPN spacer sequence, we performed experiments with SPN oligoduplex, containing proto-spacer complementary to spacer SN and PAM (FIG. 7D). Oligoduplex cleavage assay confirmed (FIGS. 7C and D) that Cas9-crRNA complex with re-engineered specificity cleaves both DNA strands within the SN proto-spacer 3 nt upstream of the PAM identically to other Cas9-crRNA complexes.

The length of the spacer in the CRISPR3 region of *S. thermophilus* is 30 nt. According to the data provided in the FIG. 1C, the mature crRNA copurified with the Cas9 protein is comprised of 42 nt. It means that only 20 nt of crRNA is complementary to the (+)strand of proto-spacer. To assess whether 5'-end of proto-spacer is important for the plasmid interference by the CRISPR3 system of *S. thermophilus* we engineered plasmids pSP1-27, pSP1-23, pSP1-19, pSP1-15, pSP1-11 with the 5'-truncated proto-spacer1 (the length of proto-spacer 27 bp, 23 bp, 19 bp, 15 bp, 11 bp, respectively), and analyzed transformation efficiency of the recipient strain containing pCRISPR3 (FIG. 8B). Plasmids containing 4 or 7 bp truncations at the 5' end of proto-spacer1, had no effect on the recipient strain ability to interfere with plasmid transformation. Shorter versions of proto-spacer (11, 15, 19 bp) abolished recipient strain ability to prevent plasmid transformation. These data shows that 5' end of the proto-spacer, which has no complementarity to mature crRNA is not important for CRISPR3/Cas function. In full support to the in vivo experiments, the SP1-20 oligoduplex containing only 20 nt of the protospacer-1 is efficiently cleaved by Cas9-crRNA (FIG. 8D and E).

PAM is required for DNA binding and cleavage by Cas9-crRNA. Plasmids carrying a proto-spacer but not PAM (pSP1-pΔ) or multiple PAM's but no proto-spacer (pUC18) are resistant for Cas9-crRNA cleavage (FIG. 8A). Hence, in accordance with in vivo data both PAM and proto-spacer are required for double-stranded DNA cleavage by Cas9-crRNA complex (Sapranauskas et al., 2011. Nucleic Acids Res 39:9275-82). To find out, whether PAM is recognized in a context of a double-stranded or a single-stranded DNA, we analyzed Cas9-crRNA binding and cleavage of oligodeoxynucleotides i) SP1 (containing both proto-spacer and PAM), ii) SP1-Δp (contains only proto-spacer), and iii) SP2 (contains only PAM). The (+)strands of these oligodeoxynucleotides were used as single-stranded DNA substrates (s(+) SP1, s(+)SP1-Δp, s(+)SP2, accordingly) (Table 1).

Figure 9:
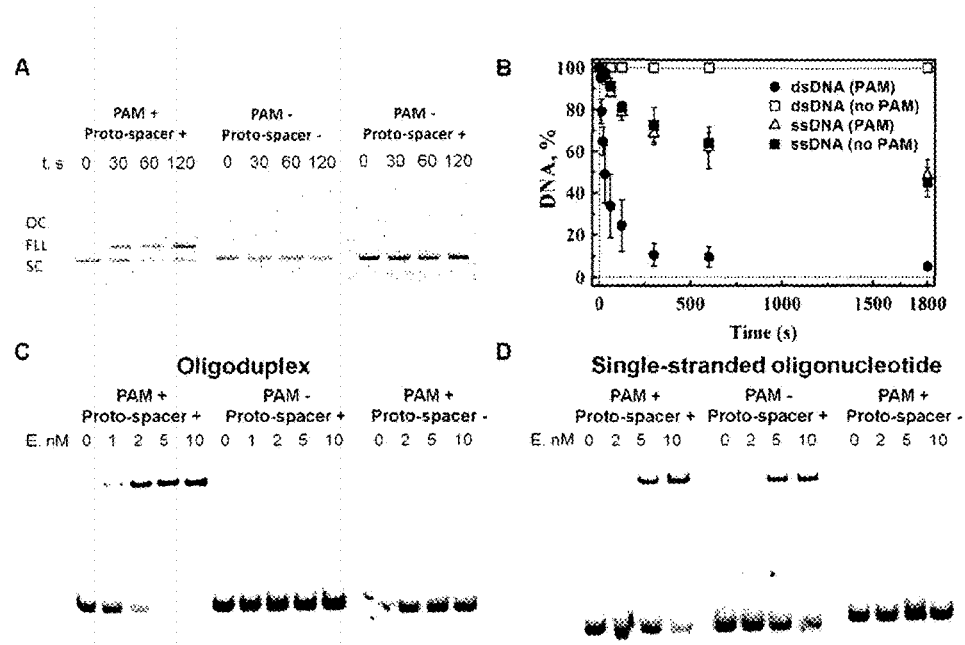
FIG. 9 shows PAM is required for in vitro DNA binding and cleavage by the Cas9-crRNA complex. (A) Agarose gel analysis of plasmid DNA cleavage products. Three different plasmids: PAM+Proto-spacer+ (pSP1 plasmid containing both the proto-spacer and PAM), PAM-Protospacer-(pUC18 plasmid containing multiple PAMs but no protospacer) and PAM-Protospacer+ (pSP1-pΔ (Sapranauskas et al., 2011. Nucleic Acids Res 39:9275-82) containing a proto-spacer without PAM) were incubated at 2.5 nM concentration with 2 nM of Cas9-crRNA complex in the reaction buffer (10 mM Tris-HCl pH=7.5, 10 mM NaCl, 10 mM MgCl2, 0.1 mg/ml BSA) at 37° C. for varied time intervals and reaction products analysed in the agarose gel. SC—super-coiled plasmid DNA, OC—open circular DNA nicked at one of DNA strands, FLL—full length linear DNA cut at both strands. (B) Time courses of (+)strand hydrolysis in the single-stranded and double-stranded oligodeoxynucleotides. Reactions containing 2 nM Cas9-crRNA and 1 nM of oligodeoxynucleotide were conducted at 37° C. in the reaction buffer (section A). SP1 (filled circles) and SP1-pt (open squares) oligoduplexes were used as dsDNA. s(+)SP1 (open triangles) and s(+) SP1-pΔ (filled squeres) were used as ssDNA. (C) and (D) dsDNA and ssDNA (+)strand) binding by Cas9-crRNA complex. The reactions contained 0.5 nM of the 33P-labelled ssDNA or dsDNA oligonucleotide, and the protein at concentrations as indicated above each lane. After 15 min at room temperature, the samples were subjected to PAGE for 2 h and analysed as described in 'Materials and Methods'

Consistent with the plasmid cleavage experiments, oligoduplexes which have only proto-spacer, but not PAM are not cut by Cas9-crRNA (FIG. 9B). On the other hand, (+)strand in the single-stranded form is cut at the similar rate independently whether it has or has not PAM (FIG. 9B). These data clearly show that PAM is required only for a double-stranded but not for a single-stranded DNA cleavage.

To test if PAM is important for DNA binding by the Cas9-crRNA complex, electrophoretic mobility shift experiments were performed. To avoid cleavage, binding experiments were performed in the absence of Mg2+ ions which are necessary for cleavage. Cas9-crRNA showed different binding patterns for double-stranded and single-stranded oligonucleotides. In the case of the SP1 oligoduplex a low mobility complex is observed already at 1 nM concentration (FIG. 9C). On the other hand, no binding is observed under the same experimental conditions for oligoduplexes without PAM (SP1-Δp) or without proto-spacer (SP2). Moreover, no low mobility complex is observed in the case of Cas9 protein without crRNA (FIG. 6A), confirming that crRNA is important for complex formation. Thus, taken together binding experiments clearly show that the Cas9 protein complex is unable to bind double-stranded DNA in the absence of PAM, even if it contains crRNA complementary to proto-spacer. To put it into other words, double-stranded DNA substrates lacking PAM are not cleaved because PAM is required for Cas9-crRNA binding.

On the other hand, single-stranded oligonucleotides ((+) strand) are bound by Cas9-crRNA with the same affinity independently of the PAM presence (FIG. 9D). Again, no binding was observed for single-stranded DNA oligonucleotide without proto-spacer (FIG. 9D), or for Cas9 protein lacking crRNA (FIG. 6C). Taken together these data indicate that Cas9-crRNA complex discriminates PAM only in the double-stranded but not a single-stranded DNA.

Figure 10:
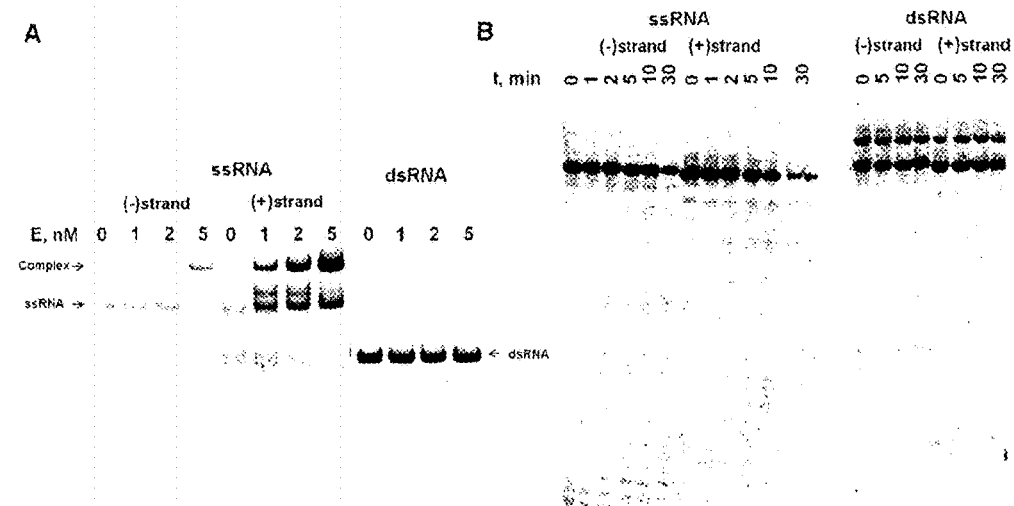
FIG. 10 shows RNA binding and cleavage analysis of Cas9-crRNA complex. (A) Electrophoretic mobility shift analysis (EMSA) of Cas9-crRNA complex binding to 84 nt RNA fragment containing proto-spacer-1, PAM and 24 nt flanking sequences on both sides. Left panel: RNA (−) strand; center panel: RNA (+) strand; right panel: double stranded RNA. RNA fragments used for analysis were generated by in vitro transcription (TranscriptAid™ T7 High Yield Transcription Kit, Fermentas) from PCR fragments with inserted T7 promoter at the front end of RNA coding sequence. PCR fragments coding (+) and (−) RNA strands were obtained from pSP1 plasmid (1) with following primer pairs accordingly: 5' taatacgactcactataGggtaccgagctgaattg 3' (SEQ ID NO: 17)/5' GGGAAACAGCTATGACCAT-GATTACGAATTC-3' (SEQ ID NO: 18) and 5' gggtac-cgagctgaattgaaattcTAAACG 3' (SEQ ID NO: 19)/5' taatac-gactcactataGggAAACAGCTATGACCATGATTACG 3' (SEQ ID NO: 20) (T7 RNA polymerase promoter underlined, transcription start on bold). The reactions contained 1 nM of the 33P-labelled RNA fragment, and the protein at concentrations as indicated above each lane. After 15 min at room temperature, the samples were subjected to PAGE for 2 h and analyzed as described in 'Materials and Methods'. (B) RNA cleavage assay. 2.5 nM of Cas9-crRNA complex was incubated in the reaction buffer (10 mM Tris-HCl pH=7.5, 10 mM NaCl, 10 mM MgCl2, 0.1 mg/ml BSA,) at 37° C. in the presence of 1 nM (+) and (−) RNA strands (left panel) or double stranded RNA labeled on (+) or (−) strand (right panel). Reaction products were analysed on denaturing PAA gel.

Since some Type III CRISPR systems provide RNA rather than DNA interference, we have studied RNA binding and cleavage by the Cas9-crRNA complex. The Cas9-crRNA did not cleave specifically either single-stranded RNA, or double-stranded RNA bearing a proto-spacer and PAM (FIG. 10B). This finding confirms confirms once more that DNA is a primary target for the CRISPR3/Cas system of S. thermophilus. Cas9-crRNA complex binds a complementary RNA containing a proto-spacer, but this interaction is probably functionally not important, because single stranded RNA is not cleaved specifically by Cas9 within a proto-spacer.

Figure 11:
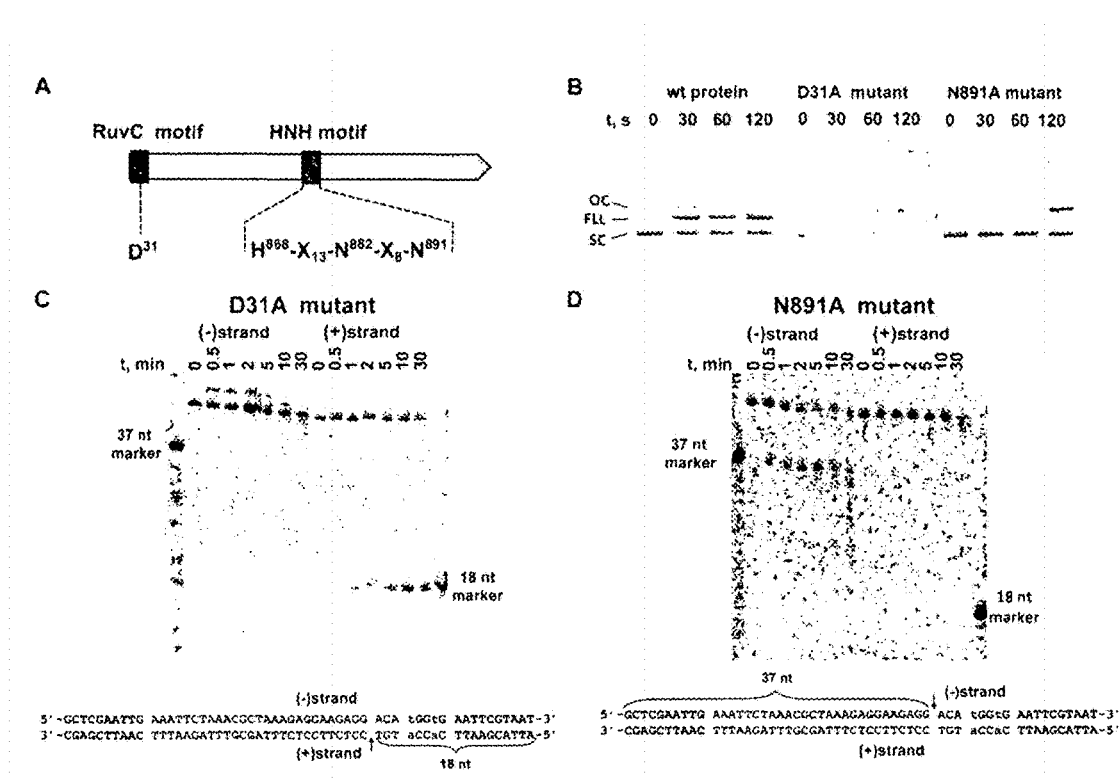
FIG. 11 shows RuvC and HNH active site motifs of Cas9 contribute to the cleavage of opposite DNA strands. (A) Localization of the conserved active site motifs within Cas9 protein. Amino acid residues identified as crucial for Cas9 in vivo activity (Sapranauskas et al., 2011. Nucleic Acids Res 39:9275-82) are indicated. (B). Agarose gel analysis of pSP1 plasmid cleavage by Cas9 and mutant proteins. Reactions were performed as described in and 'Materials and Methods' (C) Strand preference of D31A mutant. Reactions were performed as described in FIG. 2A and 'Materials and Methods'. D31 mutant cleaves only (+)strand of SP1 oligoduplex.

Mutagenesis of Cas9 protein RuvC and HNH motifs. Plasmid transformation experiments indicate that RuvC and HNH motifs (FIG. 11A) are important for Cas9 function (Sapranauskas et al., 2011. Nucleic Acids Res 39:9275-82). To test if these motifs are involved in the target DNA cleavage, we expressed and purified D31A and N891A mutants following procedure described for wt Cas9. Both mutants co-purified with crRNA identical to crRNA in the wt Cas9 complex (FIG. 11C). To test whether mutant proteins retained cleavage activity, we monitored pSP1 plasmid cleavage by mutant Cas9-crRNA complexes. Surprisingly, instead of linear reaction product observed for the wt Cas9 protein, both mutants produced nicked DNA form (FIG. 11B) indicating that both active sites mutants cleave only one DNA strand of plasmid substrate within a proto-spacer.

Figure 12:
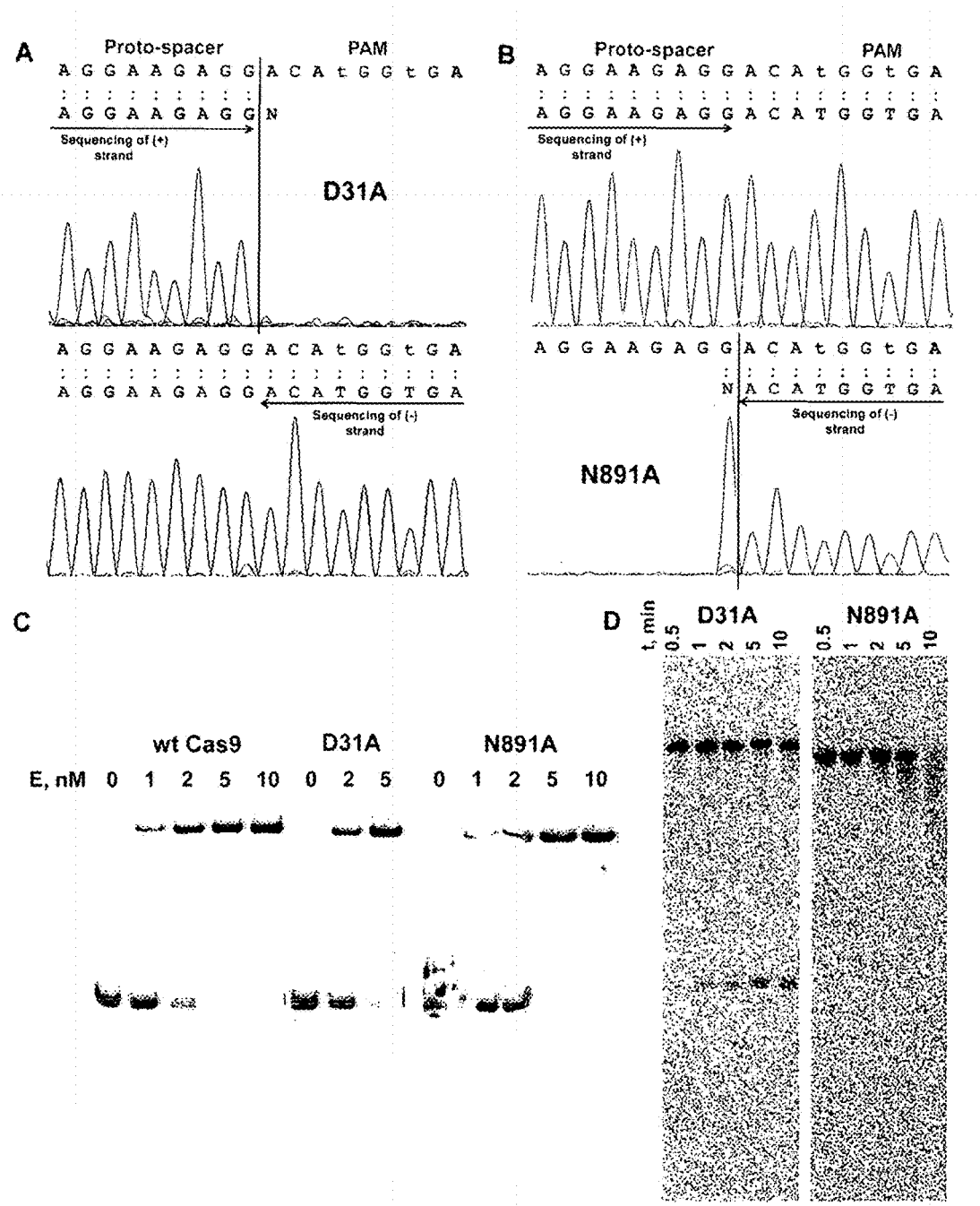
FIG. 12 shows properties of Cas9 active site mutant-crRNA complexes. (A) Direct sequencing of reaction products obtained with Cas9 mutant D31A (RuvC-like active site motif).

To determine whether mutant proteins exhibit a strand preference, we analysed D31A and N891A mutant cleavage of the SP1 oligoduplex. RuvC active site mutant (D31A) cut (+)strand of oligoduplex at the same position as wt Cas9-crRNA protein, while the (−)strand stayed intact (FIG. 11C). And vice versa, HNH active site mutant (N891A) cleaved only (−)strand, but not (+)strand of the SP1 oligoduplex (FIG. 11D). Taken together these data indicate that RuvC and HNH active sites act on opposite DNA strands to generate a double strand break. To test, whether the same cleavage pattern is conserved during the plasmid DNA cleavage, we sequenced proto-spacer regions of nicked plasmids. Run-off sequence data confirmed that RuvC active site mutant cut only (+) DNA strand while HNH/McrA mutant—only (−)strand (FIGS. 12A and B). Furthermore, we found that RuvC mutant cleaved (+)strand of a single-stranded DNA but no such cleavage was detected for the HNH mutant (FIG. 12D).

Figure 13:
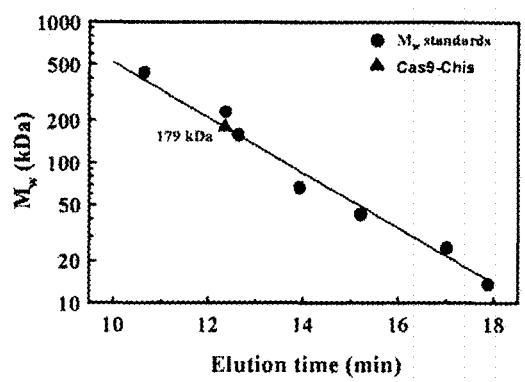
FIG. 13 shows molecular mass of the wt Cas9-Chis protein. Gel filtration experiments were carried out at room temperature using Superdex 200 10/300 GL column (GE healthcare) pre-equilibrated with 10 mM sodium phosphate (pH 7.4) buffer containing 500 mM sodium chloride. The apparent Mw of Cas9 (black triangle) were calculated by interpolation from the standard curve obtained using a set of proteins of known Mw (black circles) (Bio-Rad Gel Filtration Standards).

To test whether mutations altered DNA-binding affinity of mutant protein-crRNA complexes, DNA binding was studied using the electrophoretic mobility shift assay. Both mutant protein-crRNA complexes bound oligoduplex SP1 with the same affinity as wild type protein (FIG. 12C.). Thus, mutations in the putative active sites of Cas9 have no significant effect on double-stranded DNA-binding properties of the Cas9-crRNA complex. Since 42 nt crRNA was present in the mutant protein complexes (FIG. 12C), we conclude that mutant Cas9-crRNA complexes lost ability to cut one of the target DNA strand due to active site mutation. Since Cas9-HisTag protein is a monomer in solution (FIG. 13), it is likely that Cas9 protein is functional as a monomer and uses two active sites for the cleavage of opposite DNA strands. Similar strategy is exploited by some restriction endonucleases (Armalyte et al., 2005. J Biol Chem 280: 41584-94).

Discussion

Cas9-crRNA complex of CRISPR3/Cas system of S. thermophilus is crRNA-guided endonuclease. This work demonstrates that Cas9-crRNA complex of CRISPR3/Cas system of S. thermophilus is crRNA-directed endonuclease which cuts both DNA strands in the presence of Mg2+-ions within a protospacer 3 nt downstream of the PAM sequence to produce blunt end cleavage products. Sequence specificity of the Cas9-crRNA complex is dictated by the 42 nt crRNA which include ~20 nt fragment complementary to the proto-spacer sequence in the target DNA. In this respect the mature crRNA in the Cas9 complex of CRISPR3/Cas system of S. thermophilus is similar to crRNA of Streptoccocus pyogenes which has a 3'-handle of repeat sequence but lacks part of the spacer sequence and 5'-handle corresponding to the repeat fragment (Deltcheva et al, 2011). Therefore, crRNA present in the Cas9-crRNA complex of CRISPR3/Cas system of S. thermophilus is complementary only to the part of the proto-spacer sequence distal to PAM. Not surprisingly, truncation of the 3'-end of the proto-spacer sequence by 10 nucleotides has no effect on Cas9-crRNA cleavage of synthetic oligoduplexes or plasmid DNA (FIG. 8).

The cleavage machinery of Cas9-crRNA complex resides in the Cas9 protein which provides two active sites for the phosphodiester bond cleavage. The RuvC- and HNH-like active sites of Cas9 protein are located on different domains and act independently on individual DNA strands. Alanine replacement of the active site residues in the RuvC- and HNH-motifs transforms Cas9-crRNA complex into a strand-specific nicking endonucleases similar to the nicking enzymes (Chan et al., 2011. Nucleic Acids Res 39:1-18). Consistent with in vivo studies, a functional activity of the Cas9-crRNA complex in vitro is absolutely dependent on the presence of the proto-spacer adjacent motif NGGNG upstream of the proto-spacer sequence. Data presented in the FIG. 3 show that PAM is required for Cas9-crRNA binding to the double-stranded DNA. If PAM sequence is missing in double-stranded DNA, the Cas9-crRNA complex does not bind such DNA even if it contains a complementary proto-spacer sequence. On the other hand, Cas9-crRNA does not display DNA binding if PAM (or multiple PAM's) is present but proto-spacer sequence is absent. Thus, in consistence with the in vivo data, both PAM and proto-spacer sequences are necessary prerequisite for double-stranded DNA binding and subsequent cleavage. Contrary to the Cas9-crRNA binding to the double-stranded DNA, PAM sequence motif has no effect on the single-stranded DNA binding by: a single-stranded oligodeoxynucleotide containing proto-spacer with or without PAM sequence is bound equally well but with lower affinity than double-stranded DNA. In the presence of Mg2+ ions Cas9 cuts single-stranded DNA bound to the crRNA using its HNH-active site.

Figure 14:
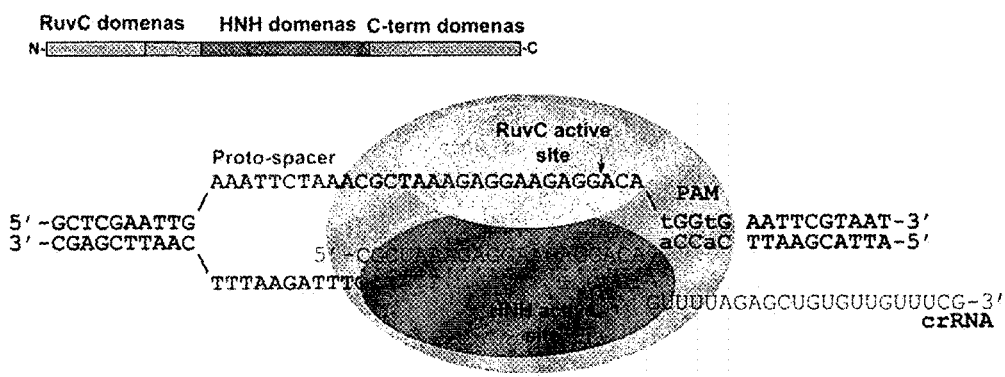
FIG. 14 shows schematic arrangement and mechanism of crRNA-directed DNA cleavage by the Cas9-crRNA complex. Domain architecture of Cas9 is shown schematically on the top. Cas9-crRNA complex binds to the dsDNA containing PAM. crRNA binds to the complementary (+)strand resulting in DNA strand separation and the R-loop formation. In the ternary complex RuvC active site of Cas9 is positioned at the scissile phosphate on the unpaired (−)strand, while HNH active site is located at the scissile phosphate on the DNA (+)strand bound to crRNA. Coordinated action of both active sites results in the double strand break 3 nt away from the 5'-NGGNG-5' PAM generating blunt end DNA.
Figure 15:
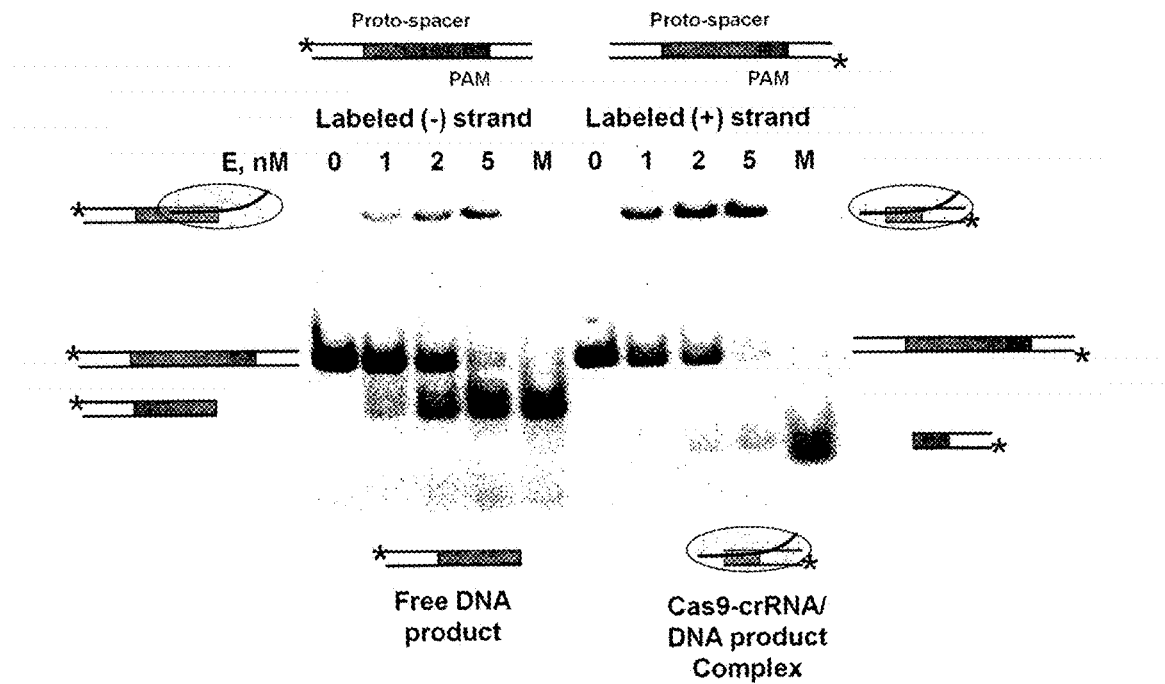
FIG. 15 shows native electrophoresis of Cas9-crRNA and cleavage products. The protein at concentrations as indicated above each lane, where incubated in the reaction buffer (10 mM Tris-HCl pH=7.5, 10 mM NaCl, 10 mM MgCl2, 0.1 mg/ml BSA) at 37° C. for 30 min in the presence of 0.5 nM SP1 oligoduplex. Samples was mixed with loading dye solution (0.01% bromphenol blue and 75 mM EDTA in 50% v/v glycerol) and analysed by non-denaturing PAGE. The gel lanes marked M—melted form of cleavage reactions products. The cartoons in each side of the gel illustrate protein-DNA complexes and DNA that correspond to each band, while cartoons below the gel illustrate major substrate form after reaction.

Mechanism of DNA interference in the Type II systems. Our results establish a simple model for the mechanism of double-stranded DNA cleavage by Cas9-crRNA complex in the S. thermophilus CRISPR3/Cas system (FIG. 14). Cas9-crRNA complexes using a mechanism that yet has to be defined locates and binds to a proto-spacer sequence within the double-stranded DNA in a PAM-dependent process. It is possible that PAM in the double-stranded DNA serves as an initiation site (signal) for the strand separation and promotes subsequent pairing of crRNA to the complementary (+)strand of DNA. It remains to be established whether a Cas9 protein module or Cas9-bound crRNA (for example, using nucleotides in the conserved the "3'-handle" of the conserved repeat sequence) recognizes the PAM sequence. Despite of the lack of these mechanistic details, our data clearly demonstrate that PAM is recognized by Cas9-crRNA in the context of double-stranded DNA. The Cas9-crRNA binding to the target sequence in the ds DNA presumably results in the R-loop structure where (−)strand is displaced and the complementary (+) DNA strand is paired to the crRNA. In the presence of Mg2+ ions phosphodiester bond cleavage occurs on both strands 3 nt 5'-upstream of the PAM sequence to generate blunt DNA ends. DNA cleavage analysis by the RuvC- or HNH-motif mutants demonstrate that RuvC- and HNH-like active sites of Cas9 protein act on the (−) and (+)strands, respectively. Therefore, in the catalytically competent the Cas9-crRNA complex, the N-terminal domain containing the catalytic D31A residue of the RuvC motif is positioned at the displaced (−) DNA strand, while the central part of Cas9 containing the HNH motif is located in the vicinity of the scissile phosphodiester bond of (+) DNA strand paired to crRNA. After DNA cleavage Cas9-crRNA remains bound to the reaction products (FIG. 15). Taken together data presented here suggest a first molecular mechanism for the DNA interference step by the CRISPR3/Cas system of S. thermophilus. Since cas9 is a signature gene (Makarova et al., 2011. Nat Rev Microbiol 9:467-77) for Type IIA and Type IIB systems the cleavage mechanism proposed here is likely to be conserved in other Type IIA and Type IIB systems. Stand-alone versions of Cas9-like proteins which are not a part of the CRISPR system were identified by bioinformatics (Makarova et al., 2011. Biol Direct 6: 38). In the light of the data provided here we suggest that these proteins can provide interference against foreign DNA similarly to Cas9 if loaded with small crRNA molecules which may be generated through the pathway different from CRISPR.

Comparison to other RNA interference complexes. The mechanism proposed here for the double-stranded DNA cleavage by the Cas9-crRNA complex differs significantly from that for the Type I-E (former E. coli or CASS2) system (Jore et al., 2011. Nat Struct Mol Biol 18:529-36). In the E. coli system crRNA and Cas proteins assemble into a large ribonucleoprotein complex named Cascade that facilitates target recognition by enhancing sequence-specific hybridization between the CRISPR RNA and complementary target sequences (Jore et al., 2011. Nat Struct Mol Biol 18:529-36). Target recognition is dependent on PAM and governed by the "seed" crRNA sequence located at the 5'-end of the spacer region (Semenova et al., 2011. Proc Natl Acad Sci USA 108:10098-103). However, while Cascade-crRNA complex alone is able to bind double-stranded DNA containing PAM and proto-spacer, it requires an accessory Cas3 protein for DNA cleavage. Cas3 is a single-stranded DNA nuclease and helicase which is able to cleave single-stranded DNA producing multiple cuts (Sinkunas et al., 2011. EMBO J 30:1335-42). The mechanistic details of the Cas3 action on a proper biological substrate (e.g., Cascade-crRNA bound to the double-stranded DNA in the R-loop like complex) have yet to be established. However, it has been demonstrated recently that Cas3 of M. jannaschii alone is able to cut both DNA strands in the synthetic substrate mimicking R-loop (Beloglazova et al., 2011. EMBO J 30:616-27). It is proposed that Cas3 may follow similar mechanism for DNA cleavage in the presence of Cascade-crRNA complex. Thus, current data clearly show that mechanistic details of the interference step for the Type I-E system differs from that of CRISPR3 system both by the catalytic machinery and mechanism and complexity.

In the III-B subtype CRISPR systems present in many archea and some bacteria, Cas module RAMP (Cmr) proteins and cRNA assemble into the effector complex that targets invading RNA (Hale et al., 2009. Cell 139:945-56; Hale et al., 2012. Mol Cell 45:292-302). In *Pyroccus furiosus* RNA silencing complex comprised of six Cmr1-6 proteins and crRNA binds to the target RNA and cuts it at fixed distance in respect to 3'-end the psiRNA. The cleavage activity depends on Mg2+-ions however individual Cmr protein(-s) responsible for target RNA cleavage has yet to be identified. The effector complex of *Sulfolobus solfataricus* comprised of seven Cmr1-7 proteins and crRNA cuts invading RNA in an endonucleolytic reaction at UA dinucleotides (Zhang et al., 2012. Mol Cell 45: 303-13). Importantly, both Cmr-crRNA complexes perform RNA cleavage in a PAM independent manner.

The data provided here show that Cas9-crRNA complex of CRISPR3 system is so far the most simple DNA interference system comprised of a single Cas9 protein bound to the crRNA molecule. The simple modular organization of the Cas9-crRNA complex where specificity for DNA target is encoded by the crRNA and cleavage machinery is brought by the Cas protein provides a versatile platform for engineering of universal RNA-guided DNA endonucleases.

Example 2

In Vitro Assembly of Cas9-crRNA Complex from 4 Components

In this example we demonstrate that the catalytically active Cas9-crRNA complex can be assembled in vitro by mixing 4 individual components: the C-terminal 6× His-tagged variant of Cas9 protein ("6× His" disclosed as SEQ ID NO: 23), tracrRNA transcript (SEQ ID NO: 5), CRISPR RNA transcript (SEQ ID NO: 8) and E. coli RNAseIII (Abgene). Cas9 protein is first pre-incubated with tracrRNA and CRISPR RNA transcripts, followed by the subsequent incubation with RNAseIII to generate a catalytically competent Cas9-crRNA complex which is used for the site-specific DNA cleavage.

More specifically, RNA fragments required for complex assembly were produced by in vitro transcription (Transcrip-tAid™ T7 High Yield Transcription Kit, Fermentas) of PCR-generated fragment containing a T7 promoter at the proximal end of RNA coding sequence. PCR-generated DNA fragments encoding CRISPR RNA and tracrRNA were produced using pCas9(−)SP1 plasmid as a template with a following primer pair: 5'-taatacgactcactataGggtagaaaaga-tatcctacgagg-3' (SEQ ID NO: 40)/5'-CAACAAC- CAAGCTAATACAGCAG-3' (SEQ ID NO: 41) and 5'-aaaaacaccgaatcggtgccac-3' (SEQ ID NO: 42)/5'-taatac-gactcactataGggTAATAATAATTGTGGTTTGAAAC-CATTC-3' (SEQ ID NO: 43) (T7 RNA polymerase promoter underlined, transcription start shown in bold). The 150 nt CRISPR RNA transcript is comprised of 102 nt Repeat-Spacer1-Repeat sequences flanked by the 23 nt upstream and 25 nt downstream regions required for primer annealing. The 105 nt transcript of tracrRNA is comprised of a 38 nt stretch partially complimentary to the *S. thermophilus* DCGG7710 CRISPR3 repeat sequence fragment (anti-repeat sequence), flanked by the 16 nt upstream and 51 nt downstream region. RNA fragments produced by in vitro transcription were purified using RNeasy MinElute Cleanup Kit (Qiagen).

For in vitro assembly of catalytically competent Cas9-crRNA complex, the 6× His-tagged Cas9 protein ("6× His" disclosed as SEQ ID NO: 23) was mixed with CRISPR RNA and tracrRNA transcripts at 1:0.5:1 molar ratio and pre-incubated in a buffer containing 10 mM Tris-HCl (pH 7.5 at 37° C.), 100 mM NaCl at 37° C. for 30 min followed by addition of RNAseIII (Ambion), MgCl2 and DTT and subsequent incubation for additional 30 min. The final concentrations of the components in the assembly mix were the following: 100 nM of 6× His-tagged Cas9 protein ("6× His" disclosed as SEQ ID NO: 23), 50 nM of CRISPR RNA, 100 nM of tracrRNA, 50 nM RNAseIII, 10 mM MgCl2 and 1 mM DTT.

Below we provide experimental evidences that in vitro assembled Cas9-crRNA complex guided by the crRNA sequence cleaves DNA at the specific site to generate blunt ends. In this respect Cas9-crRNA complex can be used an alternative for a restriction endonuclease or meganuclease for the site-specific DNA cleavage in vitro. The sequence specificity of the complex is dictated by the crRNA sequence which can be engineered to address a desirable DNA target.

Figure 16:
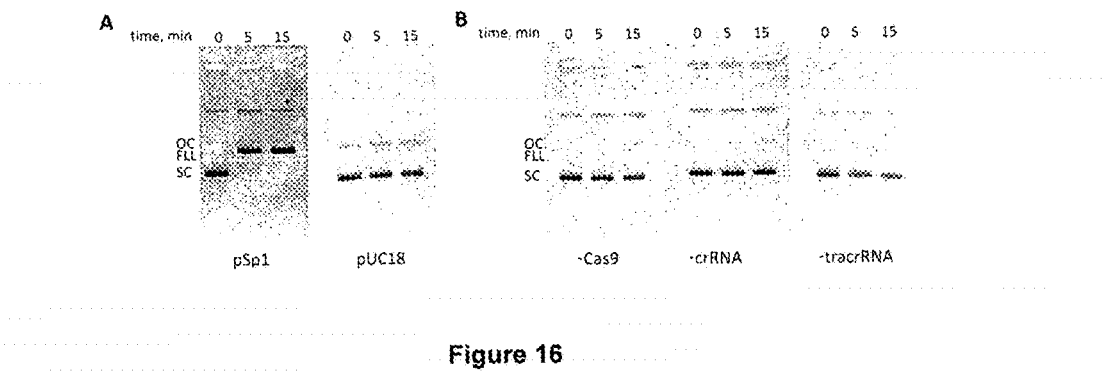
FIG. 16 shows plasmid DNA cleavage by Cas9-crRNA complex. (A) pSP1 and pUC18 plasmid DNA cleavage. Cas9-crRNA complex was incubated with pSP1 and pUC18 plasmids in a reaction buffer provided in the Example 1. pSP1 plasmid contained a proto-spacer1 sequence flanked by the 5'-NGGNG-3' PAM sequence. Proto-spacer1 sequence was not present in pUC18, Reaction products were analysed in the agarose gel. Under these conditions pSP1 plasmid is converted into a linear form while pUC18 plasmid lacking proto-spacer1 sequence is resistant to cleavage. (B) pSP1 cleavage reactions in the absence of one of the components. In the reaction mixes lacking one of the components (Cas9, crRNA or tracrRNA, respectively) pSP1 plasmid is not cleaved. SC—super-coiled plasmid DNA, OC—open circular DNA nicked at one of DNA strands, FLL—full length linear DNA cut at both strands.

First, the DNA cleavage activity of the in vitro assembled Cas9-crRNA complex was assayed on the plasmid substrates pSP1 and pUC18. The pSP1 plasmid contained a proto-spacer1 sequence flanked by the 5'-NGGNG-3' PAM sequence. Proto-spacer1 sequence was not present in pUC18. Reactions on pUC18 and pSP1 plasmids (Sapranauskas et al., 2011. Nucleic Acids Res 39:9275-82) were conducted at 37° C. in the 10 mM Tris HCl (pH 7.5 at 37° C.), 50 mM NaCl, 0.05 mg/ml BSA, 0.5 mM DTT and 10 mM MgCl2. Reaction mixtures typically contained 3.0 nM of supercoiled plasmid DNA. The reactions were initiated by mixing 50 µl volumes of Cas9-crRNA complex and plasmid DNA (1:1 v/v ratio) in a reaction buffer. Aliquots were removed at timed intervals and quenched with phenol/chloroform. The aqueous phase was mixed with loading dye solution (0.01% bromphenol blue and 75 mM EDTA in 50% v/v glycerol) and reaction products analyzed by electrophoresis through agarose (FIG. 16). To check whether the pSP1 plasmid pre-cleaved by Cas9-crRNA complex can be re-ligated, we purified linear pSP1 cleavage product from agarose gel using GeneJET gel extraction Kit (Fermentas) and re-ligated using T4 DNA ligase (Fermentas). After transformation of *E. coli* cells by the ligation mix, five individual clones were selected from resulting transformants, plasmid DNA was purified and subjected to sequencing using the following primers: 5'-ccgcatcaggcgccattcgcc-3' (SEQ ID NO: 29) (sequencing of (+)strand) and 5'-gcgaggaagcggaagagcgccc-3' (SEQ ID NO: 30) (sequencing of (−)strand). Sequence analysis revealed that the DNA sequence of the pSP1 plasmid in the locus that was cleaved by Cas9-crRNA complex and re-ligated was identical to the sequence of the non-treated plasmid. *E. coli* transformation by the ligation mix in the absence of T4 DNA ligase did not produce transformants indicating that no traces of super-coiled plasmid are co-purified with the linear reaction product.

Figure 17:
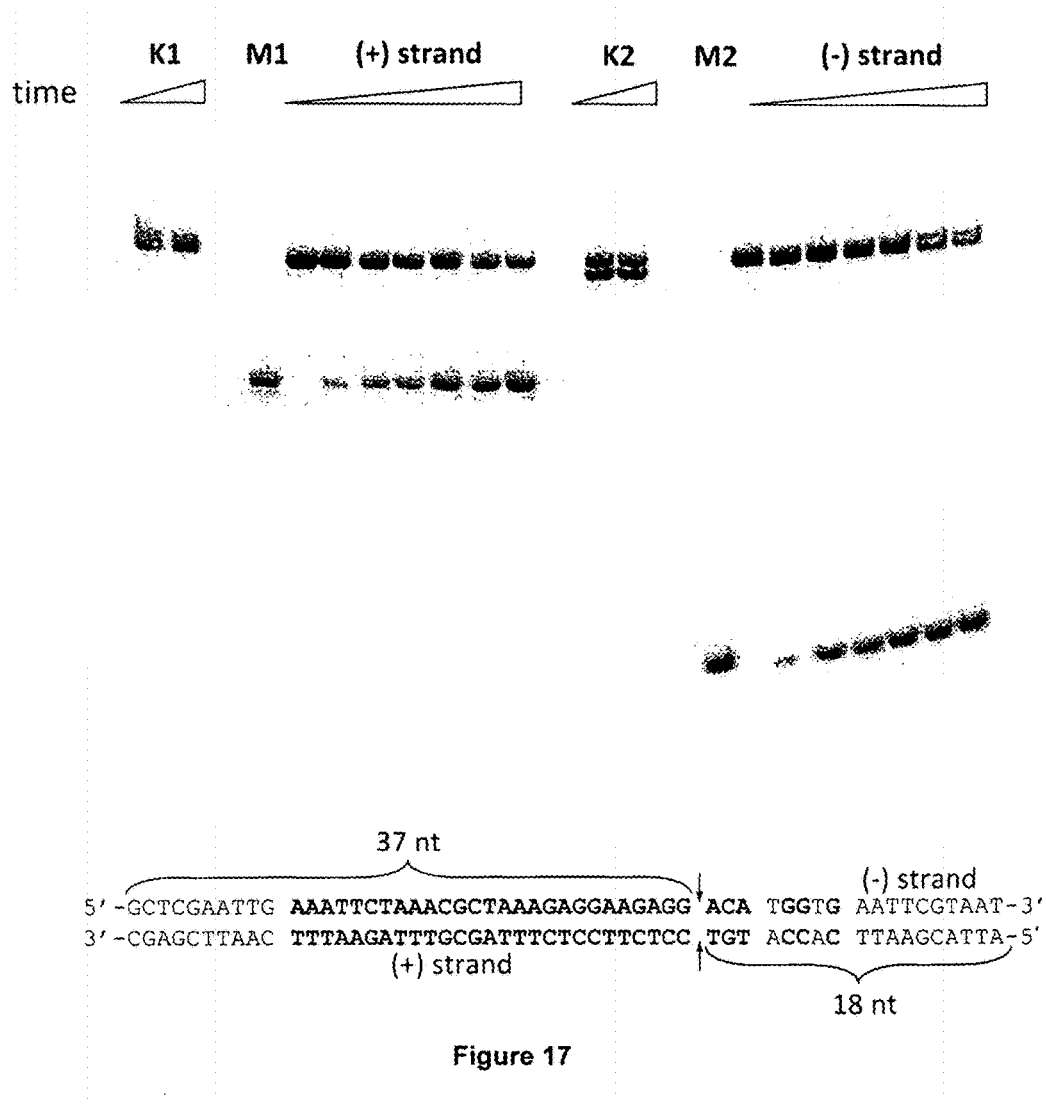
FIG. 17 shows DNA oligoduplex cleavage by Cas9-crRNA complex. The strand of oligoduplex which is complementary to crRNA is marked as (+) strand, while the other strand -(−) strand. To monitor cleavage reactions either (+) or (−) strand of the oligoduplex was P33-labeled at the 5'-terminus. M1 and M2 are synthetic oligonucleotide markers corresponding to the 37 nt of (−) strand and 18 nt of (+)

Next, the cleavage activity of the in vitro assembled Cas9-crRNA complex was assayed on a synthetic 55 bp oligodeoxynucleotide duplex SP1 containing a proto-spacer sequence matching to the spacer sequence of crRNA (FIG. 17). Reactions conditions were identical to those described above for the plasmid DNA cleavage, except that 1 nM of oligoduplex was used. Reaction product analysis revealed that in vitro assembled Cas9-crRNA complex cleaved both strands of the oligoduplex at fixed position, inside the proto-spacer, after the 37th nucleotide from the 5'-terminus, 3 nt upstream of the PAM sequence 5'-NGGNG-3' leaving blunt ends (FIG. 17).

Example 3

In Vitro Assembly of Cas9-crRNA Complex from 3 Components

In this example we demonstrate that active Cas9-crRNA complex can be assembled in vitro by mixing 3 individual components: the C-terminal 6× His-tagged variant of Cas9 protein ("6× His" disclosed as SEQ ID NO: 23), tracrRNA transcript provided in Example 1 (SEQ ID NO: 5 and SEQ ID NO: 6), and CRISPR RNA transcript (SEQ ID NO: 8) provided in Example 1 or synthetic crRNA (SEQ ID NO: 7) which corresponds to the putative crRNA of CRISPR3/Cas system of *S. thermophilus* DGCC7710 strain. Synthetic 42 nt oligoribonucleotide is comprised of 20 nt of identical to the spacer1 of CRISPR3 region at the 5' terminus and 22 nt of repeat sequence at the 3' end. More specifically, tracrRNA and CRISPR RNA transcripts were obtained as described in Example 1. To generate the Cas9-crRNA complex the 6× His-tagged Cas9 protein ("6× His" disclosed as SEQ ID NO: 23) was mixed with tracrRNA and CRISPR RNA transcript, or 42 nt synthetic crRNA, at 1:0.5:1 molar ratio and incubated in a buffer containing 10 mM Tris-HCl (pH 7.5 at 37° C.), 100 mM NaCl at 37° C. for 1 h. The final concentrations of the components in the assembly mix were the following: 100 nM of 6× His-tagged Cas9 protein ("6× His" disclosed as SEQ ID NO: 23), 50 nM of CRISPR RNA or 42 nt synthetic crRNA, 100 nM of tracrRNA.

Below we provide experimental evidences that in vitro assembled Cas9-crRNA complex guided by the crRNA sequence cleaves DNA at the specific site to generate blunt ends. In this respect Cas9-crRNA complex can be used an alternative for a restriction endonuclease or meganuclease for the site-specific DNA cleavage in vitro. The sequence specificity of the complex is dictated by the crRNA sequence which can be engineered to address a desirable DNA target.

Figure 18:
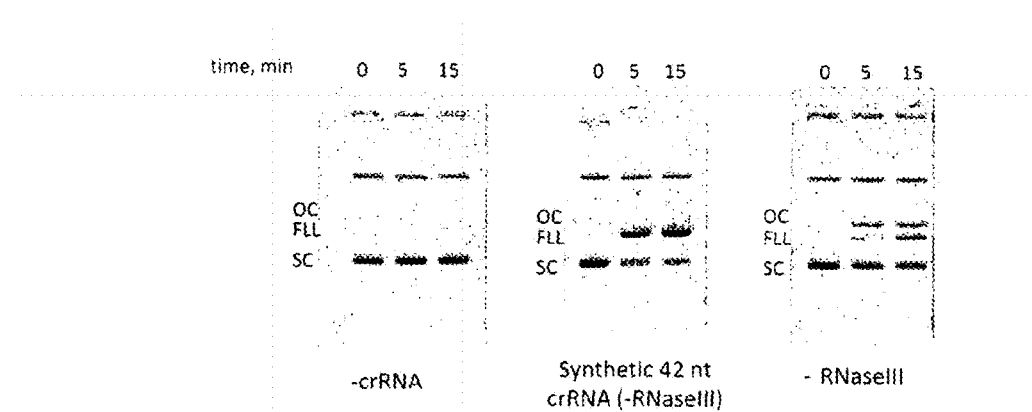
FIG. 18 shows plasmid DNA cleavage by Cas9-crRNA complex assembled in the absence of RNaseIII. Cas9-crRNA complex was incubated with pSP1 plasmid and reaction products analysed in the agarose gels. The pSP1 plasmid is resistant for cleavage in the presence of complex assembled without crRNA (left panel). The pSP1 plasmid is converted into linear form in the presence of complex assembled using synthetic 42 nt crRNA (no RNAseIII) (middle panel). The pSP1 plasmid is converted into a mixture of linear and circular DNA forms in the presence of complex assembled using CRISPR RNA transcript (no RNAseIII) (right panel).

First, the DNA cleavage activity of the in vitro assembled Cas9-crRNA complex was assayed on the plasmid substrates pSP1 and pUC18. The pSP1 plasmid contained a proto-spacer1 sequence flanked by the 5'-NGGNG-3' PAM sequence. Proto-spacer1 sequence was not present in pUC18. Reactions on plasmid substrates (Sapranauskas et al., 2011. Nucleic Acids Res 39:9275-82) were conducted at 37° C. in the 10 mM Tris-HCl (pH 7.5 at 37° C.), 50 mM NaCl, 0.05 mg/ml BSA, 0.5 mM of DTT and 10 mM MgCl2. Reaction mixtures typically contained 3.0 nM of supercoiled plasmid DNA. The reactions were initiated by mixing 50 µl volumes of Cas9-crRNA complex and plasmid DNA (1:1 v/v ratio) in a reaction buffer. Aliquots were removed at timed intervals and quenched with phenol/chloroform. The aqueous phase was mixed with loading dye solution (0.01% bromphenol blue and 75 mM EDTA in 50% v/v glycerol) and reaction products analyzed by electrophoresis through agarose (FIG. 18).

Figure 19:
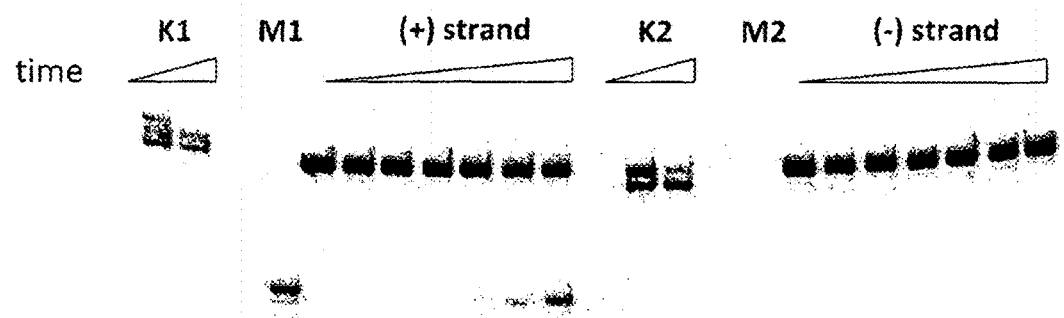
FIG. 19 shows DNA oligoduplex cleavage by Cas9-crRNA complex. The strand of oligoduplex which is complementary to crRNA is marked as (+) strand, while the other strand -(−) strand. To monitor cleavage reaction either (+) or (−) strand of the oligoduplex was P33-labeled at the 5'-terminus. M1 and M2 are synthetic oligonucleotide markers corresponding to the 37 nt of (−) strand and 18 nt of (+) strand which were used to determine the size of the cleavage products and map the cleavage position. Cas9 protein cleaves both strands of oligoduplex inside the proto-spacer, after the 37th nucleotide form the 5'-end, 3 nt upstream of the PAM (5'-NGGNG-3') leaving blunt ends. Both strands of non-specific substrate (K1 and K2) are not cleaved when incubated with Cas9-crRNA complex for 30 min.
Figure 19:
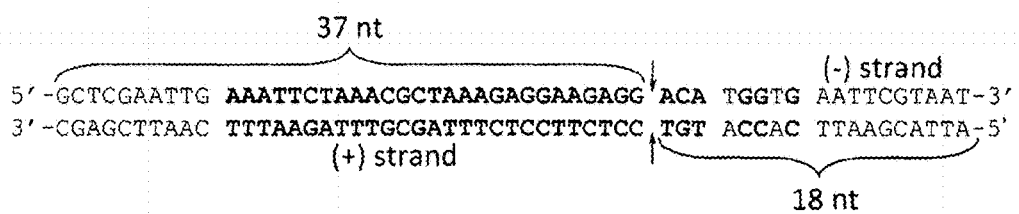

Next, the cleavage activity of the in vitro assembled Cas9-crRNA complex was assayed on a synthetic 55 bp oligodeoxynucleotide duplex SP1 containing a a proto-spacer sequence matching to the spacer sequence of crRNA (FIG. 19). Reactions conditions were identical to those described above for the plasmid DNA cleavage, except that 1 nM of oligoduplex was used. Reaction product analysis revealed that in vitro assembled Cas9-crRNA complex cleaved both strands of the oligoduplex at fixed position, inside the proto-spacer, after the 37th nucleotide form the 5'-end, 3 nt upstream of the PAM sequence 5'-NGGNG-3' leaving blunt ends (FIG. 19).

Example 4

Figure 20:
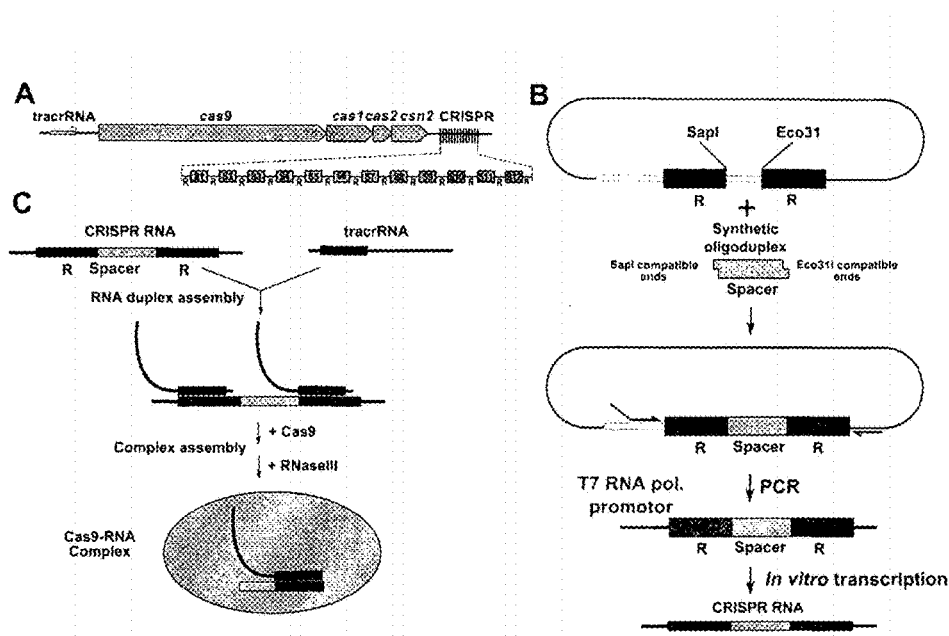
FIG. 20 shows (A) Schematic representation of the CRISPR3/Cas system of *S. thermophilus* DGCC7710. Four cas genes (cas9, cas1, cas2, csn2) are located upstream of the CRISPR repeat-spacer array, consisting of 13 repeat (R) sequences and 12 unique spacers (S1-S12). The tracrRNA, required for crRNA maturation in Type II CRISPR/Cas systems (Deltcheva et al., 2011. Nature 471, 602-7), is located upstream the cas9 gene and encoded on the opposite DNA strand (shown by an arrow) with respect to the other elements of this system. (B) The pathways for a new spacer insertion in to CRISPR region and CRISPR RNA synthesis. Synthetic oligoduplex encoding desired spacer sequence and containing SapI and Eco31I restriction compatible ends was inserted between two repeats. The CRISPR region was amplified using PCR. The new spacer encoding CRISPR RNA was obtained by In vitro transcription. (C) In vitro assembly of Cas9-RNA complex. The CRISPR RNA and tracrRNA transcripts were assembled in to duplex. The Cas9 protein was first pre-incubated with RNA duplex, followed by the subsequent incubation with RNAseIII to generate a catalytically competent Cas9-RNA complex.

Interchangeable Spacer Cassette for the re-programming of the Cas9-crRNA Complex Specificity In this example we describe an interchangeable spacer cassette which allows to produce crRNA carrying a nucleotide sequence against any desirable DNA target to be used for assembly of the Cas9-crRNA complex described in Examples 1 and 2 (FIG. 20B). The cassette caries a single repeat-spacer-repeat unit which allows insertion of the oligoduplex carrying the new spacer sequence required to generate a desired crRNA. To engineer a cassette, first we constructed a cassette containing a leader sequence, a repeat sequence and a unique SapI recognition site in the vicinity of the repeat sequence followed by BamHI site (FIG. 20C). To generate CRISPR region containing the unique desired spacer, we inserted a synthetic oligoduplex containing a unique spacer sequence and a repeat unit into the plasmid precleaved with SapI and BamHI restriction enzymes. Using this cassette we produced crRNA transcripts which contained nucleotide sequences complementary to the proto-spacers N1 and N2 present in pUC18 plasmid (see below).

Figure 21:
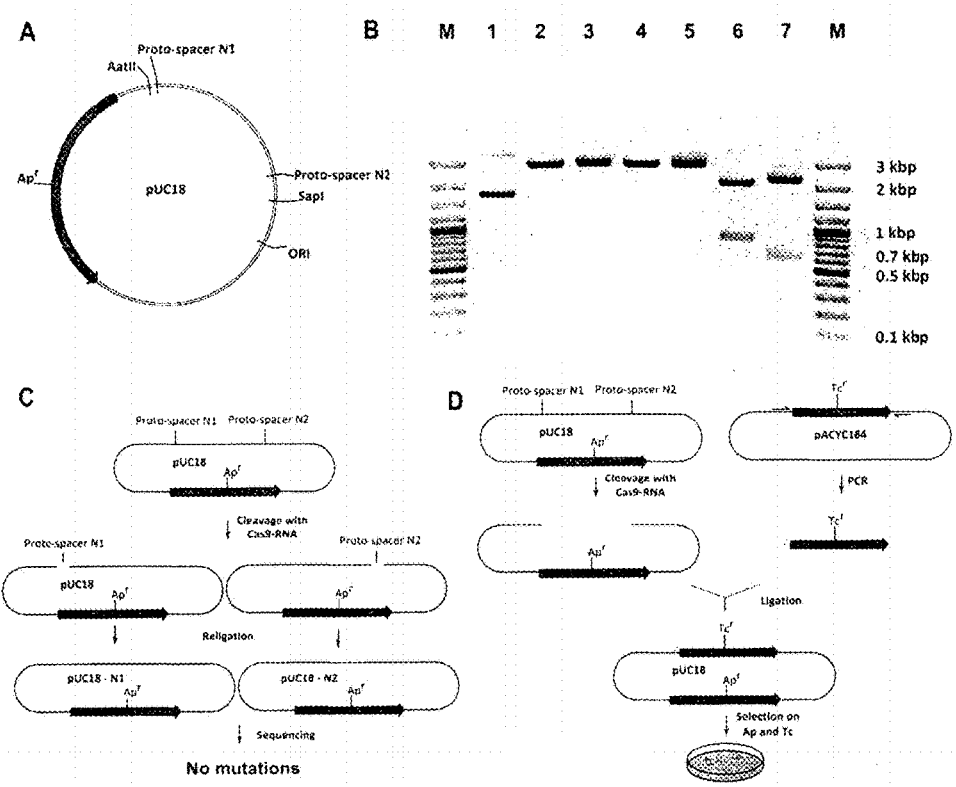
FIG. 21 shows A. Schematic representation of pUC18 plasmid. The distance between SapI and AatII restriction sites is 775 bp, while the distance between two spacers is 612 bp. B. pUC18 plasmid cleavage by re-programed Cas9-crRNA complexes. "1"—pUC18 plasmid; "2"—pUC18 cleaved with AatII; "3"—pUC18 cleaved with complex containing crRNA matching proto-spacer1; "4"—pUC18 cleaved with SapI; "5"—pUC18 cleaved with complex containing crRNA matching proto-spacer2; "6"—pUC18 cleaved with AatII and SapI; "7"—pUC18 cleaved with mix of the complexes used in the line 3 and 5.

As proof of the principle demonstration, we used an interchangeable spacer cassette to generate crRNA1 and crRNA2 which were engineered to target pUC18 plasmid at proto-spacer1 and proto-spacer2, respectively, incorporated crRNA1 and crRNA2 into Cas9 complex as described in the Example 1 and used these complexes for the cleavage of pUC18 plasmid. The proto-spacer N1 is located near the SapI restriction endonuclease site, while the proto-spacer N2 is in the vicinity of AatII site. The distance between SapI and AatII restriction sites is 775 bp, while the distance between the putative Cas9-crRNA complex cleavage sites located in the spacers N1 and N2 is 612 bp (FIG. 21A). The crRNA1 and crRNA2 PCR fragments containing T7 promoter at the proximal end were obtained from the corresponding interchangeable spacer cassette plasmids and used to produce by in vitro transcription CRISPR RNA transcripts carrying sequences matching spacer N1 or spacer N2 sequences. The catalytically active complexes of Cas9 with crRNA-1 and crRNA-2 were assembled for DNA cleavage as described in Example 1. In vitro assembled complexes containing either crRNA1 or crRNA2 linearized pUC18 plasmid (FIG. 21B). When both complexes were incubated with the pUC18plasmid, two DNA fragments (2074 and 612 bp) were obtained (FIG. 21B), indicating that plasmid cleavage occurred at sites targeted by the crRNA molecules present in the complexes.

Example 5

Cloning Procedure Using Cas9-crRNA Complex

In this example we demonstrate that Cas9-crRNA complex may be used to prepare a vector for cloning procedure. First we demonstrated that cleavage products obtained by the Cas9-crRNA complex can be re-ligated by DNA ligase. We purified linear pSP1 cleavage product from agarose gel and re-ligated it using DNA ligase. After transformation of *E. coli* cells by the ligation mix, five individual clones were selected from resulting transformants, plasmid DNA was purified and subjected to sequencing. Sequence analysis revealed that the DNA sequence of the pSP1 plasmid in the locus that was cleaved by Cas9-RNA complex and re-ligated was identical to the sequence of the non-treated plasmid. *E. coli* transformation by the ligation mix in the absence of T4 DNA ligase did not produce transformants indicating that no traces of supercoiled plasmid are co-purified with the linear reaction product. This result illustrates, that the DNA ends generated by the Cas9 cleavage are substrates for T4 DNA ligase, and therefore must contain a phosphate at the 5' terminus and a free OH group at the 3' terminus (Lehman 1974. Science 186:790-7).

Next we analyzed cleavage of pUC18 plasmid with Cas9 complex loaded with crRNA1 and crRNA2 described in Example 5 (FIG. 21A). First, pUC18 was cleaved with one complex, purified and re-ligated. Sequencing of 10 clones in each case confirmed, that sequence of cleaved and re-ligated plasmid was identical to the sequence of the non-treated plasmid (FIG. 21C). This experiment suggests that additional mutations are not introduced after cleavage by Cas9-crRNA complex and ligation, and the Cas9-crRNA complex can be used for cloning experiments. When both complexes were incubated with the pUC18 plasmid, two DNA fragments (2074 and 612 bp) were obtained (FIG. 21B), indicating that plasmid cleavage occurred at sites targeted by the crRNA molecules present in the complexes. To demonstrate that the pUC18 plasmid cleaved with Cas9-RNA complexes is suitable for a genetic engineering we cloned PCR fragment containing a promoter and a tetracycline resistance gene from the pACYC184 plasmid to the pUC18 vector pre-cleaved with the Cas9 complex mix containing both crRNA1 or crRNA2. The clones were selected on the media enriched by tetracycline and ampicillin. Sequencing of 4 selected clones confirmed that the intact PCR fragment was inserted into a desired position ((FIG. 21C).

More specifically, the 2 µg pUC18 was incubated with the mix of separately assembled Cas9-RNA complexes (250 nM each) containing different crRNAs for 1 hour at 37° C. in 100 µl reaction volume (10 mM Tris-HCl (pH 7.5 at 37° C.), 100 mM NaCl, 1 mM DTT and 10 mM MgCl$_2$). Obtained vector fragment was purified from agarose gel using Gene-JET gel extraction Kit (Thermo Fisher scientific) and divided in to two equal parts. One part of pre-cleaved vector was dephosphorylated with the FastAP alkaline phosphatase while another part was untreated. 1282 bp insert containing a promoter and a tetracycline resistance gene was obtained from the pACYC184 plasmid by PCR. After purification using the GeneJET PCR Purification Kit (Thermo Fisher scientific), a solution containing the PCR fragment was divided in to two parts. One part was phosphorylated with T4 polynucleotide kinase (Thermo Fisher scientific) while another part remained untreated. Untreated vector was ligated with the untreated PCR fragment, while a dephosphorylated vector was ligated with a phosphorylated fragment using the T4 DNA ligase (Thermo Fisher scientific). Clones were selected on a media supplemented with 100 µg/ml of Ap and 25 µg/ml Tc.

Example 6

Cleavage of Long DNA Substrates by Cas9 crRNA Complex

In this example we demonstrate that Cas9-crRNA may be addressed to cleave targets in long DNA molecules, including phage λ, E. coli and human genomic DNAs.

More specifically, we addressed Cas9-RNA complex to cleave specific sites in λ bacteriophage (48 kb), E. coli BL-21 strain (4.6 Mb) and human (3.2 Gb) genomic DNAs. Cas9-crRNA complex was assembled as described in Examples 2 and 3. We used 42 nt long synthetic crRNAs, 150 nt pre-crRNAs and tracrRNAs synthesized using in vitro transcription from templates generated as described in Example 4.

λ DNA cleavage reactions were initiated by mixing λ DNA (Thermo Fisher Scientific) with assembled Cas9-RNA complex (1:1 v/v ratio) and incubating at 37° C. Final reaction mixture contained 2 μg λ DNA, 50 nM Cas9-RNA complex, 10 mM Tris-HCl (pH 7.5 at 37° C.), 100 mM NaCl, 1 mM DTT and 10 mM MgCl$_2$ in 100 μl reaction volume. Aliquots were removed at timed intervals and quenched with phenol/chloroform. The aqueous phase was mixed with 3× loading dye solution (0.01% bromphenol blue and 75 mM EDTA in 50% v/v glycerol) and reaction products analyzed by electrophoresis through agarose gels and ethidium bromide staining. The analysis of linear λ phage genomic DNA cleavage products in agarose gel confirmed that ~40 bp length DNA is efficiently cleaved at a single site (FIG. 22A).

DNA from E. coli BL21 (DE3) strain was isolated using the Genomic DNA purification kit (Thermo Fisher Scientific). For cleavage assay, E. coli genomic DNA was combined with assembled Cas9-RNA complex (1:1 v/v ratio) and incubated for 3 hours at 37° C. Final reaction mixture contained 30 μg genomic DNA, 1 μM Cas9-RNA complex, 10 mM Tris-HCl (pH 7.5 at 37° C.), 100 mM NaCl, 1 mM DTT and 10 mM MgCl$_2$ in 300 μl reaction volume. Following incubation, 30 μl of FastDigest PstI (Thermo Fisher Scientific) was added and the reaction mix was incubated for additional 16 hours at 37° C. The reaction was terminated by heating the reaction mixture for 30 min at 55° C. with Proteinase K (0.5 mg/ml; Thermo Fisher Scientific) and SDS (0.5%, w/v) followed by 30 min incubation at room temperature with RNase A (0.25 mg/ml; Thermo Fisher Scientific). After phenol/chloroform extraction, DNA was precipitated by isopropanol and dissolved in TE buffer (10 mM Tris-HCl, pH 8.0 and 1 mM EDTA). 10 μg of DNA was mixed with 3× loading dye solution (0.01% bromphenol blue and 75 mM EDTA in 50% v/v glycerol) and electrophoresed on 1% agarose gel.

To analyse Cas9-crRNA cleavage products of E. coli genomic DNA, we designed a probe against DNA fragment containing a Cas9-RNA complex target (a proto-spacer) (FIG. 22B) and performed Southern blot analysis. Southern blot analysis was performed as described in (Sambrook et al, 1989. Molecular Cloning: A Laboratory Manual) with the following modifications. Fractionated DNA was transferred from agarose gel onto SensiBlot Plus Nylon membrane (Thermo Fisher Scientific) via semi-dry transfer. DNA was denatured and fixed on the membrane by placing it on paper towel saturated with 0.4 M NaOH for 10 min, rinsed with 2×SSC and air dried. The membrane was prehybridized with 6×SSC buffer containing 0.5% SDS and 100 μg/ml denatured salmon sperm DNA (Amresco) for 1 h at 65° C. The hybridization probe was generated by PCR using the genomic E. coli BL21(DE3) DNA as a template yielding 397 bp product. 5'-ends were dephosphorylated with FastAP phosphatase (Thermo Fisher Scientific) and radiolabelled by incubating with [γ-$^{32}$P]ATP (Hartmann Analytic) and T4 PNK (Thermo Fisher Scientific). The labeled probe was purified using GeneJET PCR Purification Kit (Thermo Fisher Scientific), denatured by heating to 95° C. for 5 min, rapidly cooled on ice and added directly to the prehybridization solution. The membrane was probed for 16 hours at 65° C. and washed twice with 2×SSC, 0.5% SDS and twice with 2×SSC, 0.1% SDS at room temperature, air dried and visualized by phosphorimaging (FLA-5100; Fujifilm).

Figure 22:
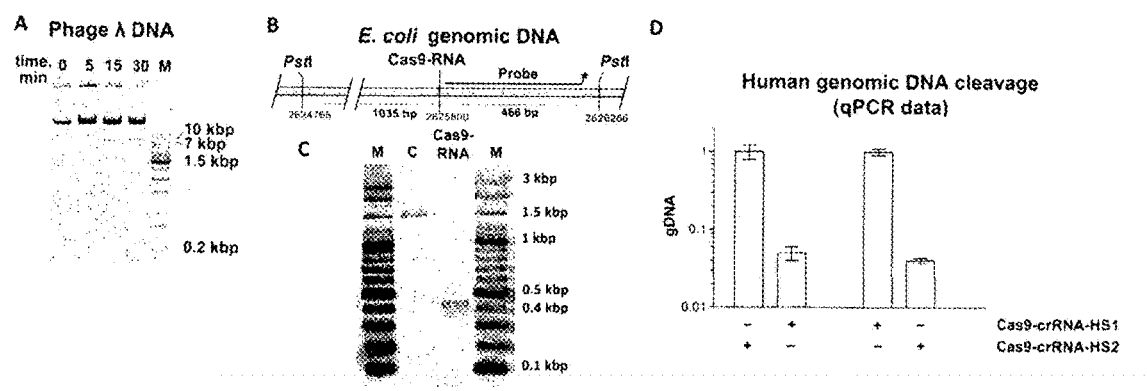
FIG. 22 shows genomic DNA cleavage with in vitro assembled Cas9-RNA complex. (A) Agarose gel analysis of linear Λ DNA cleavage products. Phage Λ DNA was incubated with Cas9-RNA complex in the reaction buffer for various time intervals. The target site for Cas9-RNA complex is located 8 kb away from the cos site. (B). Probe selection for Southern blot experiments. Genomic DNA was fragmented by treating with PstI enzyme. The proto-spacer is located between two PstI sites. If genomic DNA is cleaved with Cas9-RNA complex, 466 bp fragment should be detected. Otherwise the probe will hybridize with 1499 bp length fragment. (C) Southern blot analysis of genomic DNA fragments. C line—*E. coli* genomic DNA fragmented with PstI. Cas9-RNA—genomic DNA was incubated with Cas9-RNA complex before fragmentation. (D). Human genomic DNA cleavage by Cas9-crRNA complex. Relative amount of intact DNA DNA fragments were estimated by qPCR.

The probe was designed to target DNA fragment containing a target (a proto-spacer) for the Cas9-RNA complex (FIG. 22B). The distance between two PstI targets is ~1500 bp, while the distance between proto-spacer and left PstI target is 466 bp. After cleavage with Cas9 complex we detected only 466 bp DNA fragment (FIG. 22C), which means that all DNA targets were cleaved by Cas9 protein in the desired position. These data clearly demonstrates that Cas9 protein effectively finds targets in very long and complex molecules such as viral and bacterial DNA.

To analyze Cas9-crRNA cleavage products of human genomic DNA we used DNA extracted from human brain. Human genomic DNA was combined with assembled Cas9-crRNA complex (1:1 v/v ratio) and incubated for 30 min at 37° C. Final reaction mixture contained 1 μg genomic DNA, 100 nM Cas9, 10 mM Tris-HCl (pH 7.5 at 37° C.), 100 mM NaCl, 1 mM DTT and 10 mM MgCl$_2$ in 100 μl reaction volume. Cas9-crRNA-HS1 (SEQ ID NO: 13) and Cas9-crRNA-HS2 (SEQ ID NO: 14) complexes were assembled to target RASGEF1C or ARL15 loci, respectively. Cleavage products were analyzed using qPCR (FIG. 22D). After treatment with Cas9-crRNA complex, the amount of intact DNA targets decreased more than 25 times. The analysis of the results obtained from qPCR data revealed that Cas9-RNA complexes cleave human genomic DNA efficiently in the desired loci. These data clearly demonstrates that Cas9 protein effectively finds targets in very long and complex molecules such as viral, bacterial and mammal DNA.

The application contains a Sequence Listing which has been submitted in ASCII format and is hereby incorporated by reference in its entirety. The ASCII copy, created on Mar. 13, 2013, is named 078981.4_SL.txt and is 63.6 kilobytes in size.

The embodiments shown and described in the specification are only specific embodiments of inventors who are skilled in the art and are not limiting in any way. Therefore, various changes, modifications, or alterations to those embodiments may be made without departing from the spirit of the invention in the scope of the following claims. The references cited are expressly incorporated by reference herein in their entirety.

The invention claimed is:

1. A method for site-specific modification of a target DNA molecule, the method comprising
assembling a recombinant Cas9-crRNA complex in vitro by combining a Cas9 protein, an engineered crRNA, and a tracrRNA under conditions suitable for formation of the complex, and
contacting a target DNA molecule with the recombinant Cas9-crRNA complex, wherein the engineered crRNA is capable of universal targeting and programmed to guide the recombinant Cas9-crRNA complex to a region comprising a site in the target DNA molecule, wherein the crRNA sequence is reprogrammed to be heterologous to the Cas9 protein, and
wherein the site-specific modification of the target DNA molecule is cleavage of the target DNA molecule.

2. The method of claim 1, wherein a fragment of the crRNA is substantially complementary to the target DNA molecule.

3. The method of claim 2, wherein the fragment of the crRNA that is substantially complementary to the target DNA molecule comprises about 20 nucleotides.

4. The method of claim 2, wherein the fragment of the crRNA that is substantially complementary to the target DNA molecules comprises at least 20 nucleotides.

5. The method of claim 1, wherein the Cas9 protein comprises at least one of an RuvC active site motif and an HNH active site motif.

6. The method of claim 1, wherein the crRNA comprises a 3' and a 5' region, wherein the 3' region comprises at least 22 nucleotides of a CRISPR repeat and the 5' region comprises at least 20 nucleotides of a spacer sequence engineered to be substantially complementary to the region of the target DNA.

7. The method of claim 1, wherein the target DNA molecule comprises a proto-spacer adjacent motif (PAM) sequence.

8. The method of claim 7, wherein the PAM sequence comprises a nucleic acid molecule having the nucleic acid sequence 5'-NGGNG.

9. The method of claim 5, wherein one of the RuvC active site motif or the HNH active site motif of the Cas9 protein is inactivated, and wherein the target DNA is double stranded and the modification of the target DNA molecule is site-specific nicking of a single strand of the target DNA molecule.

10. The method of claim 1, wherein the target DNA is double stranded or single stranded.

11. The method of claim 7, wherein the PAM sequence comprises a proto-spacer upstream of the PAM.

12. The method of claim 1, wherein the recombinant Cas9-crRNA complex remains associated with the target DNA molecule after cleavage.

13. The method of claim 10, wherein the target DNA is double stranded and the proto-spacer adjacent motif (PAM) sequence is recognized in the context of double stranded DNA.

14. The method of claim 9, wherein the RuvC active site motif or the HNH active site motif of the Cas9 protein is inactivated by a point mutation.

15. The method of claim 14, wherein the point mutation in the RuvC motif is D31A and the point mutation in the HNH motif is N891A.

16. The method of claim 1 wherein, prior to assembly of the recombinant Cas9-crRNA complex, the engineered crRNA and the tracrRNA are produced by in vitro transcription or chemical synthesis; and Cas9 protein is produced by a method selected from recombinant DNA technology or chemical synthesis.

17. The method of claim 16 wherein Cas9 protein is isolated from a genetically modified microorganism.

18. The method of claim 1 wherein, prior to assembly of the recombinant Cas9-crRNA complex, Cas9 protein, the engineered crRNA, and the tracrRNA are isolated from a genetically modified microorganism.

19. The method of claim 18 wherein the genetically modified microorganism is created by introducing at least one plasmid encoding Cas9 protein, the engineered crRNA, and the tracrRNA into the microorganism, to result in the genetically modified microorganism.

20. The method of claim 19 wherein Cas9 protein, the engineered crRNA, and the tracrRNA are encoded in two separate plasmids.

21. The method of claim 19 wherein Cas9 protein, the engineered crRNA, and the tracrRNA are encoded in three separate plasmids.

22. The method of claim 1 wherein Cas9 is at least 80% identical with SEQ ID NO: 1.

23. The method of claim 1 wherein the engineered crRNA and the tracrRNA are assembled into a duplex, and then Cas9 protein is incubated with the duplex, to result in the recombinant Cas9-crRNA complex.

* * * * *

SEQUENCE LISTING

<160> NUMBER OF SEQ ID NOS: 69

<210> SEQ ID NO 1

<211> LENGTH: 1409
<212> TYPE: PRT
<213> ORGANISM: Streptococcus thermophilus

<400> SEQUENCE: 1

```
Met Leu Phe Asn Lys Cys Ile Ile Ser Ile Asn Leu Asp Phe Ser
1               5                   10                  15

Asn Lys Glu Lys Cys Met Thr Lys Pro Tyr Ser Ile Gly Leu Asp Ile
            20                  25                  30

Gly Thr Asn Ser Val Gly Trp Ala Val Ile Thr Asp Asn Tyr Lys Val
        35                  40                  45

Pro Ser Lys Lys Met Lys Val Leu Gly Asn Thr Ser Lys Lys Tyr Ile
50                  55                  60

Lys Lys Asn Leu Leu Gly Val Leu Leu Phe Asp Ser Gly Ile Thr Ala
65                  70                  75                  80

Glu Gly Arg Arg Leu Lys Arg Thr Ala Arg Arg Tyr Thr Arg Arg
                85                  90                  95

Arg Asn Arg Ile Leu Tyr Leu Gln Glu Ile Phe Ser Thr Glu Met Ala
            100                 105                 110

Thr Leu Asp Asp Ala Phe Phe Gln Arg Leu Asp Asp Ser Phe Leu Val
        115                 120                 125

Pro Asp Asp Lys Arg Asp Ser Lys Tyr Pro Ile Phe Gly Asn Leu Val
130                 135                 140

Glu Glu Lys Val Tyr His Asp Glu Phe Pro Thr Ile Tyr His Leu Arg
145                 150                 155                 160

Lys Tyr Leu Ala Asp Ser Thr Lys Lys Ala Asp Leu Arg Leu Val Tyr
                165                 170                 175

Leu Ala Leu Ala His Met Ile Lys Tyr Arg Gly His Phe Leu Ile Glu
            180                 185                 190

Gly Glu Phe Asn Ser Lys Asn Asn Asp Ile Gln Lys Asn Phe Gln Asp
        195                 200                 205

Phe Leu Asp Thr Tyr Asn Ala Ile Phe Glu Ser Asp Leu Ser Leu Glu
210                 215                 220

Asn Ser Lys Gln Leu Glu Glu Ile Val Lys Asp Lys Ile Ser Lys Leu
225                 230                 235                 240

Glu Lys Lys Asp Arg Ile Leu Lys Leu Phe Pro Gly Glu Lys Asn Ser
                245                 250                 255

Gly Ile Phe Ser Glu Phe Leu Lys Leu Ile Val Gly Asn Gln Ala Asp
            260                 265                 270

Phe Arg Lys Cys Phe Asn Leu Asp Glu Lys Ala Ser Leu His Phe Ser
        275                 280                 285

Lys Glu Ser Tyr Asp Glu Asp Leu Glu Thr Leu Leu Gly Tyr Ile Gly
290                 295                 300

Asp Asp Tyr Ser Asp Val Phe Leu Lys Ala Lys Lys Leu Tyr Asp Ala
305                 310                 315                 320

Ile Leu Leu Ser Gly Phe Leu Thr Val Thr Asp Asn Glu Thr Glu Ala
                325                 330                 335

Pro Leu Ser Ser Ala Met Ile Lys Arg Tyr Asn Glu His Lys Glu Asp
            340                 345                 350

Leu Ala Leu Leu Lys Glu Tyr Ile Arg Asn Ile Ser Leu Lys Thr Tyr
        355                 360                 365

Asn Glu Val Phe Lys Asp Asp Thr Lys Asn Gly Tyr Ala Gly Tyr Ile
370                 375                 380

Asp Gly Lys Thr Asn Gln Glu Asp Phe Tyr Val Tyr Leu Lys Asn Leu
```

```
                385                 390                 395                 400
Leu Ala Glu Phe Glu Gly Ala Asp Tyr Phe Leu Glu Lys Ile Asp Arg
                    405                 410                 415
Glu Asp Phe Leu Arg Lys Gln Arg Thr Phe Asp Asn Gly Ser Ile Pro
                420                 425                 430
Tyr Gln Ile His Leu Gln Glu Met Arg Ala Ile Leu Asp Lys Gln Ala
            435                 440                 445
Lys Phe Tyr Pro Phe Leu Ala Lys Asn Lys Glu Arg Ile Glu Lys Ile
        450                 455                 460
Leu Thr Phe Arg Ile Pro Tyr Tyr Val Gly Pro Leu Ala Arg Gly Asn
465                 470                 475                 480
Ser Asp Phe Ala Trp Ser Ile Arg Lys Arg Asn Glu Lys Ile Thr Pro
                    485                 490                 495
Trp Asn Phe Glu Asp Val Ile Asp Lys Glu Ser Ser Ala Glu Ala Phe
                500                 505                 510
Ile Asn Arg Met Thr Ser Phe Asp Leu Tyr Leu Pro Glu Glu Lys Val
            515                 520                 525
Leu Pro Lys His Ser Leu Leu Tyr Glu Thr Phe Asn Val Tyr Asn Glu
        530                 535                 540
Leu Thr Lys Val Arg Phe Ile Ala Glu Ser Met Arg Asp Tyr Gln Phe
545                 550                 555                 560
Leu Asp Ser Lys Gln Lys Lys Asp Ile Val Arg Leu Tyr Phe Lys Asp
                    565                 570                 575
Lys Arg Lys Val Thr Asp Lys Asp Ile Ile Glu Tyr Leu His Ala Ile
                580                 585                 590
Tyr Gly Tyr Asp Gly Ile Glu Leu Lys Gly Ile Glu Lys Gln Phe Asn
            595                 600                 605
Ser Ser Leu Ser Thr Tyr His Asp Leu Leu Asn Ile Ile Asn Asp Lys
        610                 615                 620
Glu Phe Leu Asp Asp Ser Ser Asn Glu Ala Ile Ile Glu Glu Ile Ile
625                 630                 635                 640
His Thr Leu Thr Ile Phe Glu Asp Arg Glu Met Ile Lys Gln Arg Leu
                    645                 650                 655
Ser Lys Phe Glu Asn Ile Phe Asp Lys Ser Val Leu Lys Lys Leu Ser
                660                 665                 670
Arg Arg His Tyr Thr Gly Trp Gly Lys Leu Ser Ala Lys Leu Ile Asn
            675                 680                 685
Gly Ile Arg Asp Glu Lys Ser Gly Asn Thr Ile Leu Asp Tyr Leu Ile
        690                 695                 700
Asp Asp Gly Ile Ser Asn Arg Asn Phe Met Gln Leu Ile His Asp Asp
705                 710                 715                 720
Ala Leu Ser Phe Lys Lys Ile Gln Lys Ala Gln Ile Ile Gly Asp
                    725                 730                 735
Glu Asp Lys Gly Asn Ile Lys Glu Val Val Lys Ser Leu Pro Gly Ser
                740                 745                 750
Pro Ala Ile Lys Lys Gly Ile Leu Gln Ser Ile Lys Ile Val Asp Glu
            755                 760                 765
Leu Val Lys Val Met Gly Gly Arg Lys Pro Glu Ser Ile Val Val Glu
        770                 775                 780
Met Ala Arg Glu Asn Gln Tyr Thr Asn Gln Gly Lys Ser Asn Ser Gln
785                 790                 795                 800
Gln Arg Leu Lys Arg Leu Glu Lys Ser Leu Lys Glu Leu Gly Ser Lys
                    805                 810                 815
```

-continued

Ile Leu Lys Glu Asn Ile Pro Ala Lys Leu Ser Lys Ile Asp Asn Asn
                820                 825                 830

Ala Leu Gln Asn Asp Arg Leu Tyr Leu Tyr Leu Gln Asn Gly Lys
        835                 840                 845

Asp Met Tyr Thr Gly Asp Leu Asp Ile Asp Arg Leu Ser Asn Tyr
850                 855                 860

Asp Ile Asp His Ile Ile Pro Gln Ala Phe Leu Lys Asp Asn Ser Ile
865                 870                 875                 880

Asp Asn Lys Val Leu Val Ser Ser Ala Ser Asn Arg Gly Lys Ser Asp
                885                 890                 895

Asp Phe Pro Ser Leu Glu Val Val Lys Lys Arg Lys Thr Phe Trp Tyr
                900                 905                 910

Gln Leu Leu Lys Ser Lys Leu Ile Ser Gln Arg Lys Phe Asp Asn Leu
        915                 920                 925

Thr Lys Ala Glu Arg Gly Gly Leu Leu Pro Glu Asp Lys Ala Gly Phe
        930                 935                 940

Ile Gln Arg Gln Leu Val Glu Thr Arg Gln Ile Thr Lys His Val Ala
945                 950                 955                 960

Arg Leu Leu Asp Glu Lys Phe Asn Asn Lys Lys Asp Glu Asn Asn Arg
                965                 970                 975

Ala Val Arg Thr Val Lys Ile Ile Thr Leu Lys Ser Thr Leu Val Ser
                980                 985                 990

Gln Phe Arg Lys Asp Phe Glu Leu Tyr Lys Val Arg Glu Ile Asn Asp
        995                 1000                1005

Phe His His Ala His Asp Ala Tyr Leu Asn Ala Val Ile Ala Ser
        1010                1015                1020

Ala Leu Leu Lys Lys Tyr Pro Lys Leu Glu Pro Glu Phe Val Tyr
        1025                1030                1035

Gly Asp Tyr Pro Lys Tyr Asn Ser Phe Arg Glu Arg Lys Ser Ala
        1040                1045                1050

Thr Glu Lys Val Tyr Phe Tyr Ser Asn Ile Met Asn Ile Phe Lys
        1055                1060                1065

Lys Ser Ile Ser Leu Ala Asp Gly Arg Val Ile Glu Arg Pro Leu
        1070                1075                1080

Ile Glu Val Asn Glu Glu Thr Gly Glu Ser Val Trp Asn Lys Glu
        1085                1090                1095

Ser Asp Leu Ala Thr Val Arg Arg Val Leu Ser Tyr Pro Gln Val
        1100                1105                1110

Asn Val Val Lys Lys Val Glu Glu Gln Asn His Gly Leu Asp Arg
        1115                1120                1125

Gly Lys Pro Lys Gly Leu Phe Asn Ala Asn Leu Ser Ser Lys Pro
        1130                1135                1140

Lys Pro Asn Ser Asn Glu Asn Leu Val Gly Ala Lys Glu Tyr Leu
        1145                1150                1155

Asp Pro Lys Lys Tyr Gly Gly Tyr Ala Gly Ile Ser Asn Ser Phe
        1160                1165                1170

Ala Val Leu Val Lys Gly Thr Ile Glu Lys Gly Ala Lys Lys Lys
        1175                1180                1185

Ile Thr Asn Val Leu Glu Phe Gln Gly Ile Ser Ile Leu Asp Arg
        1190                1195                1200

Ile Asn Tyr Arg Lys Asp Lys Leu Asn Phe Leu Leu Glu Lys Gly
        1205                1210                1215

-continued

```
Tyr Lys Asp Ile Glu Leu Ile Ile Glu Leu Pro Lys Tyr Ser Leu
    1220                1225                1230

Phe Glu Leu Ser Asp Gly Ser Arg Arg Met Leu Ala Ser Ile Leu
    1235                1240                1245

Ser Thr Asn Asn Lys Arg Gly Glu Ile His Lys Gly Asn Gln Ile
    1250                1255                1260

Phe Leu Ser Gln Lys Phe Val Lys Leu Leu Tyr His Ala Lys Arg
    1265                1270                1275

Ile Ser Asn Thr Ile Asn Glu Asn His Arg Lys Tyr Val Glu Asn
    1280                1285                1290

His Lys Lys Glu Phe Glu Leu Phe Tyr Tyr Ile Leu Glu Phe
    1295                1300                1305

Asn Glu Asn Tyr Val Gly Ala Lys Lys Asn Gly Lys Leu Leu Asn
    1310                1315                1320

Ser Ala Phe Gln Ser Trp Gln Asn His Ser Ile Asp Glu Leu Cys
    1325                1330                1335

Ser Ser Phe Ile Gly Pro Thr Gly Ser Glu Arg Lys Gly Leu Phe
    1340                1345                1350

Glu Leu Thr Ser Arg Gly Ser Ala Ala Asp Phe Glu Phe Leu Gly
    1355                1360                1365

Val Lys Ile Pro Arg Tyr Arg Asp Tyr Thr Pro Ser Ser Leu Leu
    1370                1375                1380

Lys Asp Ala Thr Leu Ile His Gln Ser Val Thr Gly Leu Tyr Glu
    1385                1390                1395

Thr Arg Ile Asp Leu Ala Lys Leu Gly Glu Gly
    1400                1405

<210> SEQ ID NO 2
<211> LENGTH: 1409
<212> TYPE: PRT
<213> ORGANISM: Streptococcus thermophilus

<400> SEQUENCE: 2

Met Leu Phe Asn Lys Cys Ile Ile Ser Ile Asn Leu Asp Phe Ser
1               5                   10                  15

Asn Lys Glu Lys Cys Met Thr Lys Pro Tyr Ser Ile Gly Leu Ala Ile
                20                  25                  30

Gly Thr Asn Ser Val Gly Trp Ala Val Ile Thr Asp Asn Tyr Lys Val
                35                  40                  45

Pro Ser Lys Lys Met Lys Val Leu Gly Asn Thr Ser Lys Lys Tyr Ile
    50                  55                  60

Lys Lys Asn Leu Leu Gly Val Leu Leu Phe Asp Ser Gly Ile Thr Ala
65                  70                  75                  80

Glu Gly Arg Arg Leu Lys Arg Thr Ala Arg Arg Arg Tyr Thr Arg Arg
                85                  90                  95

Arg Asn Arg Ile Leu Tyr Leu Gln Glu Ile Phe Ser Thr Glu Met Ala
                100                 105                 110

Thr Leu Asp Asp Ala Phe Phe Gln Arg Leu Asp Asp Ser Phe Leu Val
            115                 120                 125

Pro Asp Asp Lys Arg Asp Ser Lys Tyr Pro Ile Phe Gly Asn Leu Val
    130                 135                 140

Glu Glu Lys Val Tyr His Asp Glu Phe Pro Thr Ile Tyr His Leu Arg
145                 150                 155                 160

Lys Tyr Leu Ala Asp Ser Thr Lys Lys Ala Asp Leu Arg Leu Val Tyr
                165                 170                 175
```

```
Leu Ala Leu Ala His Met Ile Lys Tyr Arg Gly His Phe Leu Ile Glu
            180                 185                 190

Gly Glu Phe Asn Ser Lys Asn Asn Asp Ile Gln Lys Asn Phe Gln Asp
        195                 200                 205

Phe Leu Asp Thr Tyr Asn Ala Ile Phe Glu Ser Asp Leu Ser Leu Glu
    210                 215                 220

Asn Ser Lys Gln Leu Glu Glu Ile Val Lys Asp Lys Ile Ser Lys Leu
225                 230                 235                 240

Glu Lys Lys Asp Arg Ile Leu Lys Leu Phe Pro Gly Glu Lys Asn Ser
                245                 250                 255

Gly Ile Phe Ser Glu Phe Leu Lys Leu Ile Val Gly Asn Gln Ala Asp
            260                 265                 270

Phe Arg Lys Cys Phe Asn Leu Asp Glu Lys Ala Ser Leu His Phe Ser
        275                 280                 285

Lys Glu Ser Tyr Asp Glu Asp Leu Glu Thr Leu Leu Gly Tyr Ile Gly
    290                 295                 300

Asp Asp Tyr Ser Asp Val Phe Leu Lys Ala Lys Lys Leu Tyr Asp Ala
305                 310                 315                 320

Ile Leu Leu Ser Gly Phe Leu Thr Val Thr Asp Asn Glu Thr Glu Ala
                325                 330                 335

Pro Leu Ser Ser Ala Met Ile Lys Arg Tyr Asn Glu His Lys Glu Asp
            340                 345                 350

Leu Ala Leu Leu Lys Glu Tyr Ile Arg Asn Ile Ser Leu Lys Thr Tyr
        355                 360                 365

Asn Glu Val Phe Lys Asp Asp Thr Lys Asn Gly Tyr Ala Gly Tyr Ile
    370                 375                 380

Asp Gly Lys Thr Asn Gln Glu Asp Phe Tyr Val Tyr Leu Lys Asn Leu
385                 390                 395                 400

Leu Ala Glu Phe Glu Gly Ala Asp Tyr Phe Leu Glu Lys Ile Asp Arg
                405                 410                 415

Glu Asp Phe Leu Arg Lys Gln Arg Thr Phe Asp Asn Gly Ser Ile Pro
            420                 425                 430

Tyr Gln Ile His Leu Gln Glu Met Arg Ala Ile Leu Asp Lys Gln Ala
        435                 440                 445

Lys Phe Tyr Pro Phe Leu Ala Lys Asn Lys Glu Arg Ile Glu Lys Ile
    450                 455                 460

Leu Thr Phe Arg Ile Pro Tyr Tyr Val Gly Pro Leu Ala Arg Gly Asn
465                 470                 475                 480

Ser Asp Phe Ala Trp Ser Ile Arg Lys Arg Asn Glu Lys Ile Thr Pro
                485                 490                 495

Trp Asn Phe Glu Asp Val Ile Asp Lys Glu Ser Ser Ala Glu Ala Phe
            500                 505                 510

Ile Asn Arg Met Thr Ser Phe Asp Leu Tyr Leu Pro Glu Glu Lys Val
        515                 520                 525

Leu Pro Lys His Ser Leu Leu Tyr Glu Thr Phe Asn Val Tyr Asn Glu
    530                 535                 540

Leu Thr Lys Val Arg Phe Ile Ala Glu Ser Met Arg Asp Tyr Gln Phe
545                 550                 555                 560

Leu Asp Ser Lys Gln Lys Lys Asp Ile Val Arg Leu Tyr Phe Lys Asp
                565                 570                 575

Lys Arg Lys Val Thr Asp Lys Asp Ile Ile Glu Tyr Leu His Ala Ile
            580                 585                 590
```

```
Tyr Gly Tyr Asp Gly Ile Glu Leu Lys Gly Ile Glu Lys Gln Phe Asn
            595                 600                 605
Ser Ser Leu Ser Thr Tyr His Asp Leu Leu Asn Ile Ile Asn Asp Lys
    610                 615                 620
Glu Phe Leu Asp Asp Ser Ser Asn Glu Ala Ile Ile Glu Glu Ile Ile
625                 630                 635                 640
His Thr Leu Thr Ile Phe Glu Asp Arg Glu Met Ile Lys Gln Arg Leu
                645                 650                 655
Ser Lys Phe Glu Asn Ile Phe Asp Lys Ser Val Leu Lys Lys Leu Ser
            660                 665                 670
Arg Arg His Tyr Thr Gly Trp Gly Lys Leu Ser Ala Lys Leu Ile Asn
        675                 680                 685
Gly Ile Arg Asp Glu Lys Ser Gly Asn Thr Ile Leu Asp Tyr Leu Ile
    690                 695                 700
Asp Asp Gly Ile Ser Asn Arg Asn Phe Met Gln Leu Ile His Asp Asp
705                 710                 715                 720
Ala Leu Ser Phe Lys Lys Ile Gln Lys Ala Gln Ile Ile Gly Asp
                725                 730                 735
Glu Asp Lys Gly Asn Ile Lys Glu Val Val Lys Ser Leu Pro Gly Ser
            740                 745                 750
Pro Ala Ile Lys Lys Gly Ile Leu Gln Ser Ile Lys Ile Val Asp Glu
        755                 760                 765
Leu Val Lys Val Met Gly Gly Arg Lys Pro Glu Ser Ile Val Val Glu
    770                 775                 780
Met Ala Arg Glu Asn Gln Tyr Thr Asn Gln Gly Lys Ser Asn Ser Gln
785                 790                 795                 800
Gln Arg Leu Lys Arg Leu Glu Lys Ser Leu Lys Glu Leu Gly Ser Lys
                805                 810                 815
Ile Leu Lys Glu Asn Ile Pro Ala Lys Leu Ser Lys Ile Asp Asn Asn
            820                 825                 830
Ala Leu Gln Asn Asp Arg Leu Tyr Leu Tyr Tyr Leu Gln Asn Gly Lys
        835                 840                 845
Asp Met Tyr Thr Gly Asp Asp Leu Asp Ile Asp Arg Leu Ser Asn Tyr
850                 855                 860
Asp Ile Asp His Ile Ile Pro Gln Ala Phe Leu Lys Asp Asn Ser Ile
865                 870                 875                 880
Asp Asn Lys Val Leu Val Ser Ser Ala Ser Asn Arg Gly Lys Ser Asp
                885                 890                 895
Asp Phe Pro Ser Leu Glu Val Val Lys Lys Arg Lys Thr Phe Trp Tyr
            900                 905                 910
Gln Leu Leu Lys Ser Lys Leu Ile Ser Gln Arg Lys Phe Asp Asn Leu
        915                 920                 925
Thr Lys Ala Glu Arg Gly Gly Leu Leu Pro Glu Asp Lys Ala Gly Phe
    930                 935                 940
Ile Gln Arg Gln Leu Val Glu Thr Arg Gln Ile Thr Lys His Val Ala
945                 950                 955                 960
Arg Leu Leu Asp Glu Lys Phe Asn Asn Lys Lys Asp Glu Asn Asn Arg
                965                 970                 975
Ala Val Arg Thr Val Lys Ile Ile Thr Leu Lys Ser Thr Leu Val Ser
            980                 985                 990
Gln Phe Arg Lys Asp Phe Glu Leu Tyr Lys Val Arg Glu Ile Asn Asp
        995                 1000                1005
Phe His His Ala His Asp Ala Tyr Leu Asn Ala Val Ile Ala Ser
```

```
            1010                1015               1020
Ala Leu Leu Lys Lys Tyr Pro Lys Leu Glu Pro Glu Phe Val Tyr
        1025                1030              1035

Gly Asp Tyr Pro Lys Tyr Asn Ser Phe Arg Glu Arg Lys Ser Ala
        1040                1045              1050

Thr Glu Lys Val Tyr Phe Tyr Ser Asn Ile Met Asn Ile Phe Lys
        1055                1060              1065

Lys Ser Ile Ser Leu Ala Asp Gly Arg Val Ile Glu Arg Pro Leu
        1070                1075              1080

Ile Glu Val Asn Glu Glu Thr Gly Glu Ser Val Trp Asn Lys Glu
        1085                1090              1095

Ser Asp Leu Ala Thr Val Arg Arg Val Leu Ser Tyr Pro Gln Val
        1100                1105              1110

Asn Val Val Lys Lys Val Glu Glu Gln Asn His Gly Leu Asp Arg
        1115                1120              1125

Gly Lys Pro Lys Gly Leu Phe Asn Ala Asn Leu Ser Ser Lys Pro
        1130                1135              1140

Lys Pro Asn Ser Asn Glu Asn Leu Val Gly Ala Lys Glu Tyr Leu
        1145                1150              1155

Asp Pro Lys Lys Tyr Gly Gly Tyr Ala Gly Ile Ser Asn Ser Phe
        1160                1165              1170

Ala Val Leu Val Lys Gly Thr Ile Glu Lys Gly Ala Lys Lys Lys
        1175                1180              1185

Ile Thr Asn Val Leu Glu Phe Gln Gly Ile Ser Ile Leu Asp Arg
        1190                1195              1200

Ile Asn Tyr Arg Lys Asp Lys Leu Asn Phe Leu Leu Glu Lys Gly
        1205                1210              1215

Tyr Lys Asp Ile Glu Leu Ile Ile Glu Leu Pro Lys Tyr Ser Leu
        1220                1225              1230

Phe Glu Leu Ser Asp Gly Ser Arg Arg Met Leu Ala Ser Ile Leu
        1235                1240              1245

Ser Thr Asn Asn Lys Arg Gly Glu Ile His Lys Gly Asn Gln Ile
        1250                1255              1260

Phe Leu Ser Gln Lys Phe Val Lys Leu Leu Tyr His Ala Lys Arg
        1265                1270              1275

Ile Ser Asn Thr Ile Asn Glu Asn His Arg Lys Tyr Val Glu Asn
        1280                1285              1290

His Lys Lys Glu Phe Glu Glu Leu Phe Tyr Tyr Ile Leu Glu Phe
        1295                1300              1305

Asn Glu Asn Tyr Val Gly Ala Lys Lys Asn Gly Lys Leu Leu Asn
        1310                1315              1320

Ser Ala Phe Gln Ser Trp Gln Asn His Ser Ile Asp Glu Leu Cys
        1325                1330              1335

Ser Ser Phe Ile Gly Pro Thr Gly Ser Glu Arg Lys Gly Leu Phe
        1340                1345              1350

Glu Leu Thr Ser Arg Gly Ser Ala Ala Asp Phe Glu Phe Leu Gly
        1355                1360              1365

Val Lys Ile Pro Arg Tyr Arg Asp Tyr Thr Pro Ser Ser Leu Leu
        1370                1375              1380

Lys Asp Ala Thr Leu Ile His Gln Ser Val Thr Gly Leu Tyr Glu
        1385                1390              1395

Thr Arg Ile Asp Leu Ala Lys Leu Gly Glu Gly
        1400                1405
```

<210> SEQ ID NO 3
<211> LENGTH: 1409
<212> TYPE: PRT
<213> ORGANISM: Streptococcus thermophilus

<400> SEQUENCE: 3

```
Met Leu Phe Asn Lys Cys Ile Ile Ile Ser Ile Asn Leu Asp Phe Ser
1               5                   10                  15

Asn Lys Glu Lys Cys Met Thr Lys Pro Tyr Ser Ile Gly Leu Asp Ile
            20                  25                  30

Gly Thr Asn Ser Val Gly Trp Ala Val Ile Thr Asp Asn Tyr Lys Val
        35                  40                  45

Pro Ser Lys Lys Met Lys Val Leu Gly Asn Thr Ser Lys Lys Tyr Ile
    50                  55                  60

Lys Lys Asn Leu Leu Gly Val Leu Leu Phe Asp Ser Gly Ile Thr Ala
65                  70                  75                  80

Glu Gly Arg Arg Leu Lys Arg Thr Ala Arg Arg Tyr Thr Arg Arg
                85                  90                  95

Arg Asn Arg Ile Leu Tyr Leu Gln Glu Ile Phe Ser Thr Glu Met Ala
            100                 105                 110

Thr Leu Asp Asp Ala Phe Phe Gln Arg Leu Asp Asp Ser Phe Leu Val
        115                 120                 125

Pro Asp Asp Lys Arg Asp Ser Lys Tyr Pro Ile Phe Gly Asn Leu Val
    130                 135                 140

Glu Glu Lys Val Tyr His Asp Glu Phe Pro Thr Ile Tyr His Leu Arg
145                 150                 155                 160

Lys Tyr Leu Ala Asp Ser Thr Lys Lys Ala Asp Leu Arg Leu Val Tyr
                165                 170                 175

Leu Ala Leu Ala His Met Ile Lys Tyr Arg Gly His Phe Leu Ile Glu
            180                 185                 190

Gly Glu Phe Asn Ser Lys Asn Asn Asp Ile Gln Lys Asn Phe Gln Asp
        195                 200                 205

Phe Leu Asp Thr Tyr Asn Ala Ile Phe Glu Ser Asp Leu Ser Leu Glu
    210                 215                 220

Asn Ser Lys Gln Leu Glu Glu Ile Val Lys Asp Lys Ile Ser Lys Leu
225                 230                 235                 240

Glu Lys Lys Asp Arg Ile Leu Lys Leu Phe Pro Gly Glu Lys Asn Ser
                245                 250                 255

Gly Ile Phe Ser Glu Phe Leu Lys Leu Ile Val Gly Asn Gln Ala Asp
            260                 265                 270

Phe Arg Lys Cys Phe Asn Leu Asp Glu Lys Ala Ser Leu His Phe Ser
    275                 280                 285

Lys Glu Ser Tyr Asp Glu Asp Leu Glu Thr Leu Leu Gly Tyr Ile Gly
    290                 295                 300

Asp Asp Tyr Ser Asp Val Phe Leu Lys Ala Lys Lys Leu Tyr Asp Ala
305                 310                 315                 320

Ile Leu Leu Ser Gly Phe Leu Thr Val Thr Asp Asn Glu Thr Glu Ala
            325                 330                 335

Pro Leu Ser Ser Ala Met Ile Lys Arg Tyr Asn Glu His Lys Glu Asp
        340                 345                 350

Leu Ala Leu Leu Lys Glu Tyr Ile Arg Asn Ile Ser Leu Lys Thr Tyr
    355                 360                 365

Asn Glu Val Phe Lys Asp Asp Thr Lys Asn Gly Tyr Ala Gly Tyr Ile
```

```
                370                 375                 380
Asp Gly Lys Thr Asn Gln Glu Asp Phe Tyr Val Tyr Leu Lys Asn Leu
385                 390                 395                 400

Leu Ala Glu Phe Glu Gly Ala Asp Tyr Phe Leu Glu Lys Ile Asp Arg
                405                 410                 415

Glu Asp Phe Leu Arg Lys Gln Arg Thr Phe Asp Asn Gly Ser Ile Pro
                420                 425                 430

Tyr Gln Ile His Leu Gln Glu Met Arg Ala Ile Leu Asp Lys Gln Ala
                435                 440                 445

Lys Phe Tyr Pro Phe Leu Ala Lys Asn Lys Glu Arg Ile Glu Lys Ile
450                 455                 460

Leu Thr Phe Arg Ile Pro Tyr Tyr Val Gly Pro Leu Ala Arg Gly Asn
465                 470                 475                 480

Ser Asp Phe Ala Trp Ser Ile Arg Lys Arg Asn Glu Lys Ile Thr Pro
                485                 490                 495

Trp Asn Phe Glu Asp Val Ile Asp Lys Glu Ser Ser Ala Glu Ala Phe
                500                 505                 510

Ile Asn Arg Met Thr Ser Phe Asp Leu Tyr Leu Pro Glu Glu Lys Val
                515                 520                 525

Leu Pro Lys His Ser Leu Leu Tyr Glu Thr Phe Asn Val Tyr Asn Glu
530                 535                 540

Leu Thr Lys Val Arg Phe Ile Ala Glu Ser Met Arg Asp Tyr Gln Phe
545                 550                 555                 560

Leu Asp Ser Lys Gln Lys Lys Asp Ile Val Arg Leu Tyr Phe Lys Asp
                565                 570                 575

Lys Arg Lys Val Thr Asp Lys Asp Ile Ile Glu Tyr Leu His Ala Ile
                580                 585                 590

Tyr Gly Tyr Asp Gly Ile Glu Leu Lys Gly Ile Glu Lys Gln Phe Asn
                595                 600                 605

Ser Ser Leu Ser Thr Tyr His Asp Leu Leu Asn Ile Ile Asn Asp Lys
                610                 615                 620

Glu Phe Leu Asp Asp Ser Ser Asn Glu Ala Ile Ile Glu Glu Ile Ile
625                 630                 635                 640

His Thr Leu Thr Ile Phe Glu Asp Arg Glu Met Ile Lys Gln Arg Leu
                645                 650                 655

Ser Lys Phe Glu Asn Ile Phe Asp Lys Ser Val Leu Lys Lys Leu Ser
                660                 665                 670

Arg Arg His Tyr Thr Gly Trp Gly Lys Leu Ser Ala Lys Leu Ile Asn
                675                 680                 685

Gly Ile Arg Asp Glu Lys Ser Gly Asn Thr Ile Leu Asp Tyr Leu Ile
690                 695                 700

Asp Asp Gly Ile Ser Asn Arg Asn Phe Met Gln Leu Ile His Asp Asp
705                 710                 715                 720

Ala Leu Ser Phe Lys Lys Ile Gln Lys Ala Gln Ile Ile Gly Asp
                725                 730                 735

Glu Asp Lys Gly Asn Ile Lys Glu Val Val Lys Ser Leu Pro Gly Ser
                740                 745                 750

Pro Ala Ile Lys Lys Gly Ile Leu Gln Ser Ile Lys Ile Val Asp Glu
                755                 760                 765

Leu Val Lys Val Met Gly Gly Arg Lys Pro Glu Ser Ile Val Val Glu
                770                 775                 780

Met Ala Arg Glu Asn Gln Tyr Thr Asn Gln Gly Lys Ser Asn Ser Gln
785                 790                 795                 800
```

-continued

```
Gln Arg Leu Lys Arg Leu Glu Lys Ser Leu Lys Glu Leu Gly Ser Lys
            805                 810                 815
Ile Leu Lys Glu Asn Ile Pro Ala Lys Leu Ser Lys Ile Asp Asn Asn
            820                 825                 830
Ala Leu Gln Asn Asp Arg Leu Tyr Leu Tyr Tyr Leu Gln Asn Gly Lys
            835                 840                 845
Asp Met Tyr Thr Gly Asp Asp Leu Asp Ile Asp Arg Leu Ser Asn Tyr
            850                 855                 860
Asp Ile Asp His Ile Ile Pro Gln Ala Phe Leu Lys Asp Asn Ser Ile
865                 870                 875                 880
Asp Asn Lys Val Leu Val Ser Ser Ala Ser Ala Arg Gly Lys Ser Asp
            885                 890                 895
Asp Phe Pro Ser Leu Glu Val Val Lys Lys Arg Lys Thr Phe Trp Tyr
            900                 905                 910
Gln Leu Leu Lys Ser Lys Leu Ile Ser Gln Arg Lys Phe Asp Asn Leu
            915                 920                 925
Thr Lys Ala Glu Arg Gly Gly Leu Leu Pro Glu Asp Lys Ala Gly Phe
            930                 935                 940
Ile Gln Arg Gln Leu Val Glu Thr Arg Gln Ile Thr Lys His Val Ala
945                 950                 955                 960
Arg Leu Leu Asp Glu Lys Phe Asn Asn Lys Asp Glu Asn Asn Arg
            965                 970                 975
Ala Val Arg Thr Val Lys Ile Ile Thr Leu Lys Ser Thr Leu Val Ser
            980                 985                 990
Gln Phe Arg Lys Asp Phe Glu Leu Tyr Lys Val Arg Glu Ile Asn Asp
            995                1000                1005
Phe His His Ala His Asp Ala Tyr Leu Asn Ala Val Ile Ala Ser
            1010                1015                1020
Ala Leu Leu Lys Lys Tyr Pro Lys Leu Glu Pro Glu Phe Val Tyr
            1025                1030                1035
Gly Asp Tyr Pro Lys Tyr Asn Ser Phe Arg Glu Arg Lys Ser Ala
            1040                1045                1050
Thr Glu Lys Val Tyr Phe Tyr Ser Asn Ile Met Asn Ile Phe Lys
            1055                1060                1065
Lys Ser Ile Ser Leu Ala Asp Gly Arg Val Ile Glu Arg Pro Leu
            1070                1075                1080
Ile Glu Val Asn Glu Glu Thr Gly Glu Ser Val Trp Asn Lys Glu
            1085                1090                1095
Ser Asp Leu Ala Thr Val Arg Arg Val Leu Ser Tyr Pro Gln Val
            1100                1105                1110
Asn Val Val Lys Lys Val Glu Glu Gln Asn His Gly Leu Asp Arg
            1115                1120                1125
Gly Lys Pro Lys Gly Leu Phe Asn Ala Asn Leu Ser Ser Lys Pro
            1130                1135                1140
Lys Pro Asn Ser Asn Glu Asn Leu Val Gly Ala Lys Glu Tyr Leu
            1145                1150                1155
Asp Pro Lys Lys Tyr Gly Gly Tyr Ala Gly Ile Ser Asn Ser Phe
            1160                1165                1170
Ala Val Leu Val Lys Gly Thr Ile Glu Lys Gly Ala Lys Lys Lys
            1175                1180                1185
Ile Thr Asn Val Leu Glu Phe Gln Gly Ile Ser Ile Leu Asp Arg
            1190                1195                1200
```

```
Ile Asn Tyr Arg Lys Asp Lys Leu Asn Phe Leu Leu Glu Lys Gly
    1205                1210                1215

Tyr Lys Asp Ile Glu Leu Ile Ile Glu Leu Pro Lys Tyr Ser Leu
    1220                1225                1230

Phe Glu Leu Ser Asp Gly Ser Arg Arg Met Leu Ala Ser Ile Leu
    1235                1240                1245

Ser Thr Asn Asn Lys Arg Gly Glu Ile His Lys Gly Asn Gln Ile
    1250                1255                1260

Phe Leu Ser Gln Lys Phe Val Lys Leu Leu Tyr His Ala Lys Arg
    1265                1270                1275

Ile Ser Asn Thr Ile Asn Glu Asn His Arg Lys Tyr Val Glu Asn
    1280                1285                1290

His Lys Lys Glu Phe Glu Glu Leu Phe Tyr Tyr Ile Leu Glu Phe
    1295                1300                1305

Asn Glu Asn Tyr Val Gly Ala Lys Lys Asn Gly Lys Leu Leu Asn
    1310                1315                1320

Ser Ala Phe Gln Ser Trp Gln Asn His Ser Ile Asp Glu Leu Cys
    1325                1330                1335

Ser Ser Phe Ile Gly Pro Thr Gly Ser Glu Arg Lys Gly Leu Phe
    1340                1345                1350

Glu Leu Thr Ser Arg Gly Ser Ala Ala Asp Phe Glu Phe Leu Gly
    1355                1360                1365

Val Lys Ile Pro Arg Tyr Arg Asp Tyr Thr Pro Ser Ser Leu Leu
    1370                1375                1380

Lys Asp Ala Thr Leu Ile His Gln Ser Val Thr Gly Leu Tyr Glu
    1385                1390                1395

Thr Arg Ile Asp Leu Ala Lys Leu Gly Glu Gly
    1400                1405

<210> SEQ ID NO 4
<211> LENGTH: 1409
<212> TYPE: PRT
<213> ORGANISM: Streptococcus thermophilus

<400> SEQUENCE: 4

Met Leu Phe Asn Lys Cys Ile Ile Ile Ser Ile Asn Leu Asp Phe Ser
1               5                   10                  15

Asn Lys Glu Lys Cys Met Thr Lys Pro Tyr Ser Ile Gly Leu Asp Ile
                20                  25                  30

Gly Thr Asn Ser Val Gly Trp Ala Val Ile Thr Asp Asn Tyr Lys Val
            35                  40                  45

Pro Ser Lys Lys Met Lys Val Leu Gly Asn Thr Ser Lys Lys Tyr Ile
50                  55                  60

Lys Lys Asn Leu Leu Gly Val Leu Leu Phe Asp Ser Gly Ile Thr Ala
65                  70                  75                  80

Glu Gly Arg Arg Leu Lys Arg Thr Ala Arg Arg Tyr Thr Arg Arg
                85                  90                  95

Arg Asn Arg Ile Leu Tyr Leu Gln Glu Ile Phe Ser Thr Glu Met Ala
                100                 105                 110

Thr Leu Asp Asp Ala Phe Phe Gln Arg Leu Asp Asp Ser Phe Leu Val
            115                 120                 125

Pro Asp Asp Lys Arg Asp Ser Lys Tyr Pro Ile Phe Gly Asn Leu Val
130                 135                 140

Glu Glu Lys Val Tyr His Asp Glu Phe Pro Thr Ile Tyr His Leu Arg
145                 150                 155                 160
```

```
Lys Tyr Leu Ala Asp Ser Thr Lys Lys Ala Asp Leu Arg Leu Val Tyr
                165                 170                 175

Leu Ala Leu Ala His Met Ile Lys Tyr Arg Gly His Phe Leu Ile Glu
            180                 185                 190

Gly Glu Phe Asn Ser Lys Asn Asn Asp Ile Gln Lys Asn Phe Gln Asp
        195                 200                 205

Phe Leu Asp Thr Tyr Asn Ala Ile Phe Glu Ser Asp Leu Ser Leu Glu
    210                 215                 220

Asn Ser Lys Gln Leu Glu Glu Ile Val Lys Asp Lys Ile Ser Lys Leu
225                 230                 235                 240

Glu Lys Lys Asp Arg Ile Leu Lys Leu Phe Pro Gly Glu Lys Asn Ser
                245                 250                 255

Gly Ile Phe Ser Glu Phe Leu Lys Leu Ile Val Gly Asn Gln Ala Asp
            260                 265                 270

Phe Arg Lys Cys Phe Asn Leu Asp Glu Lys Ala Ser Leu His Phe Ser
        275                 280                 285

Lys Glu Ser Tyr Asp Glu Asp Leu Glu Thr Leu Leu Gly Tyr Ile Gly
    290                 295                 300

Asp Asp Tyr Ser Asp Val Phe Leu Lys Ala Lys Lys Leu Tyr Asp Ala
305                 310                 315                 320

Ile Leu Leu Ser Gly Phe Leu Thr Val Thr Asp Asn Glu Thr Glu Ala
                325                 330                 335

Pro Leu Ser Ser Ala Met Ile Lys Arg Tyr Asn Glu His Lys Glu Asp
            340                 345                 350

Leu Ala Leu Leu Lys Glu Tyr Ile Arg Asn Ile Ser Leu Lys Thr Tyr
        355                 360                 365

Asn Glu Val Phe Lys Asp Asp Thr Lys Asn Gly Tyr Ala Gly Tyr Ile
    370                 375                 380

Asp Gly Lys Thr Asn Gln Glu Asp Phe Tyr Val Tyr Leu Lys Asn Leu
385                 390                 395                 400

Leu Ala Glu Phe Glu Gly Ala Asp Tyr Phe Leu Glu Lys Ile Asp Arg
                405                 410                 415

Glu Asp Phe Leu Arg Lys Gln Arg Thr Phe Asp Asn Gly Ser Ile Pro
            420                 425                 430

Tyr Gln Ile His Leu Gln Glu Met Arg Ala Ile Leu Asp Lys Gln Ala
        435                 440                 445

Lys Phe Tyr Pro Phe Leu Ala Lys Asn Lys Glu Arg Ile Glu Lys Ile
    450                 455                 460

Leu Thr Phe Arg Ile Pro Tyr Tyr Val Gly Pro Leu Ala Arg Gly Asn
465                 470                 475                 480

Ser Asp Phe Ala Trp Ser Ile Arg Lys Arg Asn Glu Lys Ile Thr Pro
                485                 490                 495

Trp Asn Phe Glu Asp Val Ile Asp Lys Glu Ser Ser Ala Glu Ala Phe
            500                 505                 510

Ile Asn Arg Met Thr Ser Phe Asp Leu Tyr Leu Pro Glu Glu Lys Val
        515                 520                 525

Leu Pro Lys His Ser Leu Leu Tyr Glu Thr Phe Asn Val Tyr Asn Glu
    530                 535                 540

Leu Thr Lys Val Arg Phe Ile Ala Glu Ser Met Arg Asp Tyr Gln Phe
545                 550                 555                 560

Leu Asp Ser Lys Gln Lys Lys Asp Ile Val Arg Leu Tyr Phe Lys Asp
                565                 570                 575
```

-continued

```
Lys Arg Lys Val Thr Asp Lys Asp Ile Ile Glu Tyr Leu His Ala Ile
            580                 585                 590
Tyr Gly Tyr Asp Gly Ile Glu Leu Lys Gly Ile Glu Lys Gln Phe Asn
        595                 600                 605
Ser Ser Leu Ser Thr Tyr His Asp Leu Leu Asn Ile Ile Asn Asp Lys
    610                 615                 620
Glu Phe Leu Asp Asp Ser Ser Asn Glu Ala Ile Ile Glu Glu Ile Ile
625                 630                 635                 640
His Thr Leu Thr Ile Phe Glu Asp Arg Glu Met Ile Lys Gln Arg Leu
                645                 650                 655
Ser Lys Phe Glu Asn Ile Phe Asp Lys Ser Val Leu Lys Lys Leu Ser
            660                 665                 670
Arg Arg His Tyr Thr Gly Trp Gly Lys Leu Ser Ala Lys Leu Ile Asn
        675                 680                 685
Gly Ile Arg Asp Glu Lys Ser Gly Asn Thr Ile Leu Asp Tyr Leu Ile
    690                 695                 700
Asp Asp Gly Ile Ser Asn Arg Asn Phe Met Gln Leu Ile His Asp Asp
705                 710                 715                 720
Ala Leu Ser Phe Lys Lys Lys Ile Gln Lys Ala Gln Ile Ile Gly Asp
                725                 730                 735
Glu Asp Lys Gly Asn Ile Lys Glu Val Val Lys Ser Leu Pro Gly Ser
            740                 745                 750
Pro Ala Ile Lys Lys Gly Ile Leu Gln Ser Ile Lys Ile Val Asp Glu
        755                 760                 765
Leu Val Lys Val Met Gly Gly Arg Lys Pro Glu Ser Ile Val Val Glu
    770                 775                 780
Met Ala Arg Glu Asn Gln Tyr Thr Asn Gln Gly Lys Ser Asn Ser Gln
785                 790                 795                 800
Gln Arg Leu Lys Arg Leu Glu Lys Ser Leu Lys Glu Leu Gly Ser Lys
                805                 810                 815
Ile Leu Lys Glu Asn Ile Pro Ala Lys Leu Ser Lys Ile Asp Asn Asn
            820                 825                 830
Ala Leu Gln Asn Asp Arg Leu Tyr Leu Tyr Tyr Leu Gln Asn Gly Lys
        835                 840                 845
Asp Met Tyr Thr Gly Asp Asp Leu Asp Ile Asp Arg Leu Ser Asn Tyr
    850                 855                 860
Asp Ile Asp Ala Ile Ile Pro Gln Ala Phe Leu Lys Asp Asn Ser Ile
865                 870                 875                 880
Asp Asn Lys Val Leu Val Ser Ser Ala Ser Asn Arg Gly Lys Ser Asp
                885                 890                 895
Asp Phe Pro Ser Leu Glu Val Val Lys Lys Arg Lys Thr Phe Trp Tyr
            900                 905                 910
Gln Leu Leu Lys Ser Lys Leu Ile Ser Gln Arg Lys Phe Asp Asn Leu
        915                 920                 925
Thr Lys Ala Glu Arg Gly Gly Leu Leu Pro Asp Lys Ala Gly Phe
    930                 935                 940
Ile Gln Arg Gln Leu Val Glu Thr Arg Gln Ile Thr Lys His Val Ala
945                 950                 955                 960
Arg Leu Leu Asp Glu Lys Phe Asn Asn Lys Lys Asp Glu Asn Asn Arg
                965                 970                 975
Ala Val Arg Thr Val Lys Ile Ile Thr Leu Lys Ser Thr Leu Val Ser
            980                 985                 990
Gln Phe Arg Lys Asp Phe Glu Leu  Tyr Lys Val Arg Glu  Ile Asn Asp
```

```
              995                 1000                1005
      Phe His  His Ala  His Asp  Ala Tyr  Leu Asn  Ala Val  Ile Ala Ser
          1010          1015              1020

Ala Leu  Leu Lys  Lys Tyr  Pro Lys  Leu Glu  Pro Glu  Phe Val Tyr
          1025          1030              1035

Gly Asp  Tyr Pro  Lys Tyr  Asn Ser  Phe Arg  Glu Arg  Lys Ser Ala
          1040          1045              1050

Thr Glu  Lys Val  Tyr Phe  Tyr Ser  Asn Ile  Met Asn  Ile Phe Lys
          1055          1060              1065

Lys Ser  Ile Ser  Leu Ala  Asp Gly  Arg Val  Ile Glu  Arg Pro Leu
          1070          1075              1080

Ile Glu  Val Asn  Glu Glu  Thr Gly  Glu Ser  Val Trp  Asn Lys Glu
          1085          1090              1095

Ser Asp  Leu Ala  Thr Val  Arg Arg  Val Leu  Ser Tyr  Pro Gln Val
          1100          1105              1110

Asn Val  Val Lys  Lys Val  Glu Glu  Gln Asn  His Gly  Leu Asp Arg
          1115          1120              1125

Gly Lys  Pro Lys  Gly Leu  Phe Asn  Ala Asn  Leu Ser  Ser Lys Pro
          1130          1135              1140

Lys Pro  Asn Ser  Asn Glu  Asn Leu  Val Gly  Ala Lys  Glu Tyr Leu
          1145          1150              1155

Asp Pro  Lys Lys  Tyr Gly  Gly Tyr  Ala Gly  Ile Ser  Asn Ser Phe
          1160          1165              1170

Ala Val  Leu Val  Lys Gly  Thr Ile  Glu Lys  Gly Ala  Lys Lys Lys
          1175          1180              1185

Ile Thr  Asn Val  Leu Glu  Phe Gln  Gly Ile  Ser Ile  Leu Asp Arg
          1190          1195              1200

Ile Asn  Tyr Arg  Lys Asp  Lys Leu  Asn Phe  Leu Leu  Glu Lys Gly
          1205          1210              1215

Tyr Lys  Asp Ile  Glu Leu  Ile Ile  Glu Leu  Pro Lys  Tyr Ser Leu
          1220          1225              1230

Phe Glu  Leu Ser  Asp Gly  Ser Arg  Arg Met  Leu Ala  Ser Ile Leu
          1235          1240              1245

Ser Thr  Asn Asn  Lys Arg  Gly Glu  Ile His  Lys Gly  Asn Gln Ile
          1250          1255              1260

Phe Leu  Ser Gln  Lys Phe  Val Lys  Leu Leu  Tyr His  Ala Lys Arg
          1265          1270              1275

Ile Ser  Asn Thr  Ile Asn  Glu Asn  His Arg  Lys Tyr  Val Glu Asn
          1280          1285              1290

His Lys  Lys Glu  Phe Glu  Glu Leu  Phe Tyr  Tyr Ile  Leu Glu Phe
          1295          1300              1305

Asn Glu  Asn Tyr  Val Gly  Ala Lys  Lys Asn  Gly Lys  Leu Leu Asn
          1310          1315              1320

Ser Ala  Phe Gln  Ser Trp  Gln Asn  His Ser  Ile Asp  Glu Leu Cys
          1325          1330              1335

Ser Ser  Phe Ile  Gly Pro  Thr Gly  Ser Glu  Arg Lys  Gly Leu Phe
          1340          1345              1350

Glu Leu  Thr Ser  Arg Gly  Ser Ala  Ala Asp  Phe Glu  Phe Leu Gly
          1355          1360              1365

Val Lys  Ile Pro  Arg Tyr  Arg Asp  Tyr Thr  Pro Ser  Ser Leu Leu
          1370          1375              1380

Lys Asp  Ala Thr  Leu Ile  His Gln  Ser Val  Thr Gly  Leu Tyr Glu
          1385          1390              1395
```

```
Thr Arg Ile Asp Leu Ala Lys Leu Gly Glu Gly
    1400             1405

<210> SEQ ID NO 5
<211> LENGTH: 102
<212> TYPE: RNA
<213> ORGANISM: Streptococcus thermophilus

<400> SEQUENCE: 5
uaauaauaau uguggguuuga aaccauucga aacaacacag cgaguuaaaa uaaggcuuag    60
uccguacuca acuugaaaag guggcaccga uucgguguuu uu                       102

<210> SEQ ID NO 6
<211> LENGTH: 78
<212> TYPE: RNA
<213> ORGANISM: Streptococcus thermophilus

<400> SEQUENCE: 6
gggcgaaaca acacagcgag uuaaaauaag gcuuaguccg uacucaacuu gaaaaggugg    60
caccgauucg uguuuuu                                                   78

<210> SEQ ID NO 7
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 7
cgcuaaagag gaagaggaca guuuuagagc uguuguguuu cg                       42

<210> SEQ ID NO 8
<211> LENGTH: 150
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 8
ggguagaaaa gauauccuac gagguuuuag agcuguguug uuucgaaugg uuccaaaaca    60
aauucuaaac gcuaaagagg aagaggacag uuuuagagcu guugguuuc gaauggguucc    120 aaaacuacug cuguauuagc uuggguuguug                                    150

<210> SEQ ID NO 9
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 9
ggguagaaaa gauauccuac gagguuuuag agcuguguug uuucgaaugg uuccaaaact    60
gtcatgataa taatggtttc ttagacgtcg uuuuagagcu guuguguuuc gaauggguucc   120
```

-continued

```
aaaacuacug cuguauuagc uugguuguug                                150
```

<210> SEQ ID NO 10
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 10

```
ggguagaaaa gauauccuac gagguuuuag agcuguguug uuucgaaugg uuccaaaaca    60
cgagccggaa gcataaagtg taaagcctgg uuuuagagcu guuguuuuc gaaugguucc   120 aaaacuacug cuguauuagc uugguuguug                                   150
```

<210> SEQ ID NO 11
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 11

```
ggguagaaaa gauauccuac gagguuuuag agcuguguug uuucgaaugg uuccaaaact    60
caagggagaa tagaggctct cgttgcattg uuuuagagcu guuguuuuc gaaugguucc   120 aaaacuacug cuguauuagc uugguuguug                                   150
```

<210> SEQ ID NO 12
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 12

```
ggguagaaaa gauauccuac gagguuuuag agcuguguug uuucgaaugg uuccaaaacc    60
gggagggaag ctgcatgatg cgatgttatg uuuuagagcu guuguuuuc gaaugguucc   120 aaaacuacug cuguauuagc uugguuguug                                   150
```

<210> SEQ ID NO 13
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
gcucccgggg cucgaugaag guuuuagagc uguguuguuu cg        42

<210> SEQ ID NO 14
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 14
ugaaucguga aaucugcuca guuuuagagc uguguuguuu cg        42

<210> SEQ ID NO 15
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (1)..(20)
<223> OTHER INFORMATION: a, c, u, g, unknown or other

<400> SEQUENCE: 15
nnnnnnnnnn nnnnnnnnnn guuuuagagc uguguuguuu cg        42

<210> SEQ ID NO 16
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16
ccacccagca aaattcggtt ttctggctg                       29

<210> SEQ ID NO 17
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 17
taatacgact cactataggg taccgagctc gaattg               36

<210> SEQ ID NO 18
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 18
gggaaacagc tatgaccatg attacgaatt c                    31

<210> SEQ ID NO 19
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 19
gggtaccgag ctcgaattga aattctaaac g                              31

<210> SEQ ID NO 20
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 20
taatacgact cactataggg aaacagctat gaccatgatt acg                  43

<210> SEQ ID NO 21
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 21
acgtctcaaa tgttgtttaa taagtgtata ataatttc                        38

<210> SEQ ID NO 22
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 22
acgtctccgc gctaccctct cctagtttg                                  29

<210> SEQ ID NO 23
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic 6xHis tag"

<400> SEQUENCE: 23

His His His His His His
1               5

<210> SEQ ID NO 24
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 24
acgtctcaca tgactaagcc atactcaatt ggac        34

<210> SEQ ID NO 25
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 25
actcgagacc ctctcctagt ttggcaa        27

<210> SEQ ID NO 26
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 26
gaccacttat tgaggtaaat gag        23

<210> SEQ ID NO 27
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 27
caaaccagga tccaagctaa tacagcag        28

<210> SEQ ID NO 28
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

<400> SEQUENCE: 28
tcgaaacaac acagctctaa aactgtcctc ttcctcttta gc        42

<210> SEQ ID NO 29
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 29
ccgcatcagg cgccattcgc c        21

<210> SEQ ID NO 30
<211> LENGTH: 22
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 30
gcgaggaagc ggaagagcgc cc                                              22

<210> SEQ ID NO 31
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31
gctcgaattg aaattctaaa cgctaaagag gaagaggaca tggtgaattc gtaat          55

<210> SEQ ID NO 32
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 32
gctcgaattg aaattctaaa cgctaaagag gaagaggaca aattcgtaat                50

<210> SEQ ID NO 33
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33
gctcgaattg tactgctgta ttagcttggt tgttggtttg tggtgaattc gtaat          55

<210> SEQ ID NO 34
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 34
attacgaatt caccatgtcc tcttcctctt tagcgtttag aatttcaatt cgagc          55

<210> SEQ ID NO 35
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 35
attacgaatt tgtcctcttc ctctttagcg tttagaattt caattcgagc                50
```

-continued

<210> SEQ ID NO 36
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 36
attacgaatt caccacaaac caacaaccaa gctaatacag cagtacaatt cgagc        55

<210> SEQ ID NO 37
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 37
gctcgaattg aaattctaaa cgctaaagag gaagaggaca tggtgaattc gtaat        55

<210> SEQ ID NO 38
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38
gctcgaattg cgctaaagag gaagaggaca tggtgaattc gtaat                   45

<210> SEQ ID NO 39
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
gctcgaattg ccacccagca aaattcggtt ttctggctga tggtgaattc gtaat        55

<210> SEQ ID NO 40
<211> LENGTH: 41
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 40
taatacgact cactataggg tagaaaagat atcctacgag g                       41

<210> SEQ ID NO 41
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:

```
                          Synthetic primer"

<400> SEQUENCE: 41
caacaaccaa gctaatacag cag                                            23

<210> SEQ ID NO 42
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 42
aaaaacaccg aatcggtgcc ac                                             22

<210> SEQ ID NO 43
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 43
taatacgact cactataggg taataataat tgtggtttga aaccattc                 48

<210> SEQ ID NO 44
<211> LENGTH: 73
<212> TYPE: RNA
<213> ORGANISM: Streptococcus thermophilus

<400> SEQUENCE: 44
gggcgaaaca acacagcgag uuaaaauaag gcuuaguccg uacucaacuu gaaaaggugg    60
caccgauucg gug                                                       73

<210> SEQ ID NO 45
<211> LENGTH: 68
<212> TYPE: RNA
<213> ORGANISM: Streptococcus thermophilus

<400> SEQUENCE: 45
gggcgaaaca acacagcgag uuaaaauaag gcuuaguccg uacucaacuu gaaaaggugg    60
caccgauu                                                             68

<210> SEQ ID NO 46
<211> LENGTH: 63
<212> TYPE: RNA
<213> ORGANISM: Streptococcus thermophilus

<400> SEQUENCE: 46
gggcgaaaca acacagcgag uuaaaauaag gcuuaguccg uacucaacuu gaaaaggugg    60
cac                                                                  63

<210> SEQ ID NO 47
<211> LENGTH: 58
<212> TYPE: RNA
<213> ORGANISM: Streptococcus thermophilus

<400> SEQUENCE: 47
gggcgaaaca acacagcgag uuaaaauaag gcuuaguccg uacucaacuu gaaaaggu     58
```

<210> SEQ ID NO 48
<211> LENGTH: 53
<212> TYPE: RNA
<213> ORGANISM: Streptococcus thermophilus

<400> SEQUENCE: 48
gggcgaaaca acacagcgag uuaaaauaag gcuuaguccg uacucaacuu gaa    53

<210> SEQ ID NO 49
<211> LENGTH: 48
<212> TYPE: RNA
<213> ORGANISM: Streptococcus thermophilus

<400> SEQUENCE: 49
gggcgaaaca acacagcgag uuaaaauaag gcuuaguccg uacucaac    48

<210> SEQ ID NO 50
<211> LENGTH: 36
<212> TYPE: DNA
<213> ORGANISM: Streptococcus thermophilus

<400> SEQUENCE: 50
gttttagagc tgtgttgttt cgaatggttc caaaac    36

<210> SEQ ID NO 51
<211> LENGTH: 36
<212> TYPE: DNA
<213> ORGANISM: Streptococcus pyrogenes

<400> SEQUENCE: 51
gttttagagc tatgctgttt tgaatggtcc caaaac    36

<210> SEQ ID NO 52
<211> LENGTH: 36
<212> TYPE: DNA
<213> ORGANISM: Streptococcus thermophilus

<400> SEQUENCE: 52
tttaactcgc tgtgttgttt cgaatggttt caaacc    36

<210> SEQ ID NO 53
<211> LENGTH: 36
<212> TYPE: DNA
<213> ORGANISM: Streptococcus pyrogenes

<400> SEQUENCE: 53
tttaacttgc tatgctgttt tgaatggttc caacaa    36

<210> SEQ ID NO 54
<211> LENGTH: 42
<212> TYPE: RNA
<213> ORGANISM: Streptococcus pyrogenes

<400> SEQUENCE: 54
gauuucuucu ugcgcuuuuu guuuuagagc uaugcuguuu ug    42

<210> SEQ ID NO 55
<211> LENGTH: 42
<212> TYPE: RNA
<213> ORGANISM: Streptococcus thermophilus

<400> SEQUENCE: 55

```
guucacugua cgaguacuua guuuuagagc uguuguuu cg                              42

<210> SEQ ID NO 56
<211> LENGTH: 42
<212> TYPE: RNA
<213> ORGANISM: Streptococcus thermophilus

<400> SEQUENCE: 56
cgcuaaagag gaagaggaca guuuuagagc uguuguuu cg                              42

<210> SEQ ID NO 57
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 57
aaattctaaa cgctaaagag gaagaggaca tggtg                                   35

<210> SEQ ID NO 58
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 58
aggaagagga catggtga                                                      18

<210> SEQ ID NO 59
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59
aggaagagga                                                               10

<210> SEQ ID NO 60
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 60
tacatggtga                                                               10

<210> SEQ ID NO 61
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 61
```

```
caccatgtcc tcttcctctt tagcgtttag aattt                          35
```

<210> SEQ ID NO 62
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 62

```
caccatgtcc tcttcctctt tagcgtttag aa                             32
```

<210> SEQ ID NO 63
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 63

```
caccatgtcc tcttcctctt tagcgttt                                  28
```

<210> SEQ ID NO 64
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 64

```
caccatgtcc tcttcctctt tagc                                      24
```

<210> SEQ ID NO 65
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 65

```
caccatgtcc tcttcctctt                                           20
```

<210> SEQ ID NO 66
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 66

```
caccatgtcc tcttcc                                               16
```

<210> SEQ ID NO 67
<211> LENGTH: 55
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 67
attacgaatt ctccttgtcc tcttcctctt tagcgtttag aatttcaatt cgagc         55

<210> SEQ ID NO 68
<211> LENGTH: 55
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 68
attacgaatt gtggttgtcc tcttcctctt tagcgtttag aatttcaatt cgagc         55

<210> SEQ ID NO 69
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 69
gcuaaagagg aagaggacag uuuuagagcu guguuguuuc ga                      42
```